(12) United States Patent
Berry et al.

(10) Patent No.: US 11,370,771 B2
(45) Date of Patent: Jun. 28, 2022

(54) INHIBITORS OF TRPC6

(71) Applicant: Boehringer Ingelheim International GmbH, Ingelheim am Rhein (DE)

(72) Inventors: Angela Kay Berry, Gaylordsville, CT (US); Thierry Bouyssou, Warthausen (DE); Dirk Gottschling, Mittelbiberach (DE); Niklas Heine, Biberach an der Riss (DE); Matthew Russell Netherton, Danbury, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 16/969,599

(22) PCT Filed: Feb. 14, 2019

(86) PCT No.: PCT/US2019/017939
§ 371 (c)(1),
(2) Date: Aug. 13, 2020

(87) PCT Pub. No.: WO2019/161010
PCT Pub. Date: Aug. 22, 2019

(65) Prior Publication Data
US 2021/0053935 A1    Feb. 25, 2021

Related U.S. Application Data

(60) Provisional application No. 62/631,518, filed on Feb. 16, 2018.

(51) Int. Cl.
*C07D 401/04* (2006.01)
*C07D 405/14* (2006.01)

(52) U.S. Cl.
CPC ......... *C07D 401/04* (2013.01); *C07D 405/14* (2013.01)

(58) Field of Classification Search
CPC .. C07D 237/20; C07D 401/04; C07D 403/04; C07D 405/12; C07D 405/14
See application file for complete search history.

(56) References Cited

FOREIGN PATENT DOCUMENTS

| EP | 1396487 A1 | 3/2004 |
|---|---|---|
| WO | 2005011653 A2 | 2/2005 |
| WO | 2009139576 | 11/2009 |

OTHER PUBLICATIONS

Wu et al. Kidney International , p. 1-12. (Year: 2016).*
Lin et al. PNAS, vol. 116, p. 1-6. (Year: 2019).*
International Report on Patentability, PCT/US2019/017939 dated Aug. 20, 2020.
International Search Report and Written Opinion for PCT/US2019/017939 dated May 18, 2020.
Abstract for WO2009139576 cited herein, (2009).

* cited by examiner

*Primary Examiner* — Paul V Ward
(74) *Attorney, Agent, or Firm* — David L. Kershner

(57) ABSTRACT

The present invention relates to polycyclic compounds of formula (I) and pharmaceutically acceptable salts thereof, wherein $R^1$ to $R^4$, $R^7$ to $R^{10}$, Y and A are as defined herein. The invention also relates to pharmaceutical compositions comprising these compounds, methods of using these compounds in the treatment of various diseases and disorders, processes for preparing these compounds and intermediates useful in these processes.

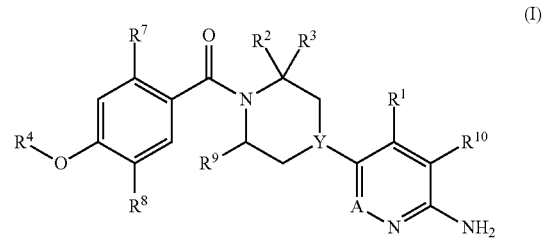

(I)

10 Claims, No Drawings

INHIBITORS OF TRPC6

FIELD OF THE INVENTION

The present invention relates to pharmaceutical compounds, compositions, and methods for the treatment of cardiac and respiratory conditions, renal disease, liver disease, muscular dystrophy, fibrotic disorders, pain, ischemia or ischemic reperfusion injury, and cancer, as well as inhibiting the Transient Receptor Potential C6 ion channel (TRPC6).

BACKGROUND

A variety of ion channel proteins exist to mediate ion flux across cellular membranes. The proper expression and function of ion channel proteins is essential for the maintenance of cell function, intracellular communication, and the like. An important aspect of achieving cellular homeostasis is the maintenance of appropriate ion concentrations in various cell types during development and in response to numerous stimuli. Large numbers of diverse types of ion channels act to maintain cellular homeostasis by moving ions into and out of cells across the plasma membrane, and within cells by moving ions across membranes of intracellular organelles including, for example, the endoplasmic reticulum, sarcoplasmic reticulum, mitochondria and endocytic organelles including endosomes and lysosomes. Numerous diseases are the result of dysregulation of membrane potential or aberrant calcium handling. Given the central importance of ion channels in modulating membrane potential and ion flux in cells, identification of agents that can promote or inhibit particular ion channels is of great interest as research tools and as possible therapeutic agents.

One such channel is the Transient Receptor Potential C6 (TRPC6) channel. TRPC6 belongs to the larger family of TRP ion channels (see, Desai et al., 2005 Eur J Physiol 451:11-18; Clapham et al., 2001 Nat Neurosci 2:387-396; Clapham, 2003 Nature 426: 517-524; Clapham et al., 2002 IUPHAR Compendium). TRPC6 is a calcium permeable channel, specifically a non-selective calcium permeable cation channel. In addition to calcium ions, TRPC6 channels are permeable to other cations, for example sodium. Thus, TRPC6 channels modulate not only intracellular calcium concentration, but also membrane potential by modulating the flux of cations including calcium and sodium ions. Although non-selective cation channels such as TRPC6 modulate, among other things, calcium ion flux, they are mechanistically distinct from voltage-gated calcium channels. Generally, voltage-gated calcium channels respond to depolarization of the potential difference across the membrane and can open to permit an influx of calcium from the extracellular medium and a rapid increase in intracellular calcium levels or concentrations. In contrast, non-selective cation channels such as TRPC6 are generally signal transduction gated, long lasting, and produce less rapid changes in ion concentration. In addition, TRPC6 can respond to changes in pressure. These mechanistic differences are accompanied by structural differences among voltage-gated and cation permeable channels. Thus, although many diverse channels act to regulate ion flux and membrane potential in various cell types and in response to numerous stimuli, it is important to recognize the significant structural, functional, and mechanistic differences among different classes of ion channels.

TRPC6 function has been implicated in, among other things, the modulation of myogenic tone. TRPC6 is highly expressed in smooth muscle cells, vascular smooth muscle cells, endothelial cells, cardiomyocytes, pulmonary arteries, the aorta, heart, liver, brain, and kidney. The expression of TRPC6, along with experiments conducted in knock-out mice and cells in culture, suggest that TRPC6 may provide a useful target for the treatment of hypertension and other cardiac and vascular conditions, preeclampsia, focal segmental glomerulsclerosis (FSGS), nephrotic syndrome, minimal change disease, diabetic nephropathy, or other kidney conditions, respiratory conditions, restenosis, liver disease, muscular dystrophy, fibrotic disorders, pain, ischemia and ischemic reperfusion injury, and certain forms of cancer.

Yue et al. studied TRPC6 channels for a role in mediating the pulmonary artery smooth muscle cell proliferation that can lead to idiopathic pulmonary arterial hypertension (IPAH). Pulmonary vascular medial hypertrophy caused by excessive pulmonary artery smooth muscle cell (PASMC) proliferation is a major cause for the elevated pulmonary vascular resistance in patients with IPAH. The authors found that TRPC6 was highly expressed and TRPC3 was minimally expressed in PASMC from healthy lung tissue. However, in lung tissue from IPAH patients, mRNA and protein expression of TRPC3 and TRPC6 were significantly elevated in comparison to that in normotensive patients. Furthermore, proliferation of PASMC cells derived from IPAH patients was markedly reduced following incubation with TRPC6 siRNA. Based on these results, the authors concluded that TRPC6 may be important in mediating proper PASMC proliferation, and that dysregulation of TRPC6 may lead to increased PASMC proliferation and pulmonary vascular medial hypertrophy observed in IPAH patients (Yu et al., 2004 Proc Natl Acad Sci 101(38):13861-6). Further support is provided by the observation that in IPAH patients the frequency of a single-nucleotide polymorphism in the promoter of TRPC6 which increases expression was significantly higher when compared to normal subjects (Yue, et al., 2009 Circulation 119: 2313-22).

Additional evidence implicating TRPC6 dysregulation in IPAH comes from studies of bosentan, a dual endothelin receptor blocker, that has been used clinically to treat IPAH. This inhibitor decreases proliferation of PASMCs, but the mechanism by which this occurs is unclear. Interestingly, bosentan both decreases proliferation of PASMC and also decreases expression of TRPC6 in lung tissue of IPAH patients (Kunichika et al., 2004 Am J Respir Crit Care Med 170(10):1101-7).

Chronic exposure of cigarette smoke (CS) to rats resulted in an increase in TRPC6 mRNA and protein expression in distal pulmonary arteries and similar effects were observed using PASMCs in vitro. Nicotine treatment of cultured rat PASMCs upregulated TRPC6 expression and increased intracellular calcium levels, both of which were reduced by TRPC6 siRNA silencing (Wang et al., 2014 Am J Physiol Cell Physiol 306:C364-73). These results suggest a role for TRPC6 in CS-induced lung injury.

Evidence supports a role of TRPC6 in additional pulmonary disorders. In alveolar macrophages from patients with chronic obstructive pulmonary disease (COPD), TRPC6 expression was found to be elevated when compared with controls (Finney-Hayward et al., 2010 Am J Respir Cell Mol Biol 43:296-304). In human cystic fibrosis epithelial cells, the TRPC6-mediated calcium influx is abnormally increased and may contribute to the hypersecretion of mucus. siRNA-TRPC6 was able to reduce this abnormal calcium influx (Antigny et al. 2011 Am J Resp Cell Mol Biol, 44:83-90). In mouse lung fibroblasts, the pro-fibrotic activity of PDGF is dependent on the activation of TRPC6, suggesting that TRPC6 inhibition would reduce lung fibrosis (Lei et al., 2014 Biomaterials 35:2868-77). A role of TRPC6 in pulmonary endothelial cell function was demonstrated in mouse lung models of ischemia-reperfusion induced-edema and lipopolysaccharide-induced inflammation in which TRPC6 deficiency was able to reduce acute lung injury by preserving endothelial barrier function (Weissmann et al., 2011 Nat Comm, 3:649-58 and Tauseef et al., 2012 J Exp Med 209:1953-68).

Recent studies also implicate the role of TRPC6 in other cardiac conditions, including cardiac hypertrophy. The hearts of patients with dilated cardiomyopathy have elevated TRPC6 mRNA expression when compared with normal hearts (Kuwahara et al., 2006 J Clin Invest 116:3114-26). In mouse models of cardiac hypertrophy, TRPC6 cardiac mRNA levels are elevated by pressure overload (Kuwahara et al., 2006 J Clin Invest 116:3114-26), chronic isoproterenol treatment (Xie et al., 2012 Nat Commun 3:1238), and uremic cardiomyopathy induced by partial nephrectomy (Xie et al., 2015 J Am Soc Nephrol 26:1150-60). Furthermore, cardiac-specific overexpression of TRPC6 in the cardiomyoctes of transgenic mice induced cardiac hypertrophy and premature death (Kuwahara et al., 2006 J Clin Invest 116:3114-26).

Wu and colleagues found that transgenic mice expressing dominant-negative TRPC6 in a cardiac-specific fashion had an attenuated cardiac hypertrophic response following either neuroendocrine agonist infusion or pressure-overload simulation, indicating that TRPC6 is a component of channel complexes that are essential mediators of hypertrophy (Wu et al., 2010 Proc Natl Acad Sci. 107:7000-05). Small molecule drugs targeting TRPC6 have also recently begun to show promise in treating cardiac conditions. For example, Seo and coworkers demonstrated that TRPC6 and TRPC3 antagonists (GSK2332255B and GSK833503A) exhibited dose-dependent inhibition of cell hypertrophy signaling in neonatal and adult cardiac myocytes (Seo et al., 2014 Proc Natl Acad Sci 111:1551-1556). Similarly, mice deficient for TRPC6 were protected from isoproterenol-induced cardiac hypertrophy (Xie et al., 2012 Nat Commun 3:1238).

Reducing TRPC6 activity may be beneficial for the treatment of cardiovascular disease. In vitro, atheroprone shear stress-induces increased TRPC6 mRNA levels in human vascular endothelial cells (EC) when compared to atheroprotective flow conditions (Thilo, et al., 2012 Hypertension 59:1232-40). EC migration is important for healing after arterial injury, and lysophosphatidylcholine-mediated inhibition of EC migration was prevented in vitro in cells from TRPC6 deficient mice. Furthermore, high cholesterol diet combined with carotid injury did not impair healing in TRPC6 deficient mice when compared with wild-type controls (Rosembaum et al., 2015 J Vasc Surg 62:1040-47 and Chaudhuri et al., 2008 Mol Biol Cell 19: 3203-11). Similarly, balloon dilatation-induced injury of human internal mammary arteries ex vivo resulted in increased TRPC6 mRNA levels when compared with undilated arteries (Bergdahl et al., 2005 Am J Physiol Cell Physiol 288:C872-80). Apoptosis of endothelial cells is involved in the initiation and progression of atherosclerotic lesions, and oxidized low-density lipoprotein-induced apoptosis of human aortic ECs was demonstrated to be dependent on TRPC6 (Zhang et al., 2015 Sci Rep 5:9401-10). In a rat model of forebrain ischaemia, TRPC6 mRNA levels were increased in vascular SMCs and correlated with reduced cerebral blood flow (Johannson et al., 2015 Acta Physiol 214:376-89). Additionally, TRPC6 genetic deficiency or treatment with a TRPC6 antagonist improved endothelial function in mice after mild traumatic brain injuries (Chen et al., 2019, J. Neuroinflamm. 16: 21).

Studies by Reiser, Winn, and Schlöndorff identified mutations in TRPC6 in patients with FSGS (Reiser et al., 2005 Nature Genet 37:739-744; Winn et al., 2005 Science 308: 1801-1804; Schlöndorff et al., 2009 Am J Physiol Cell Physiol 296:C558-69). Subsequent studies identified additional TRPC6 mutations associated with steroid-resistant nephrotic syndrome (C. Sadowski et al., 2014 J Am Soc Nephrol 26:1279-89). Further studies demonstrated that TRPC6 is important in normal podocyte function by controlling calcium influx and nuclear factor of activated T cell activation in which elevated current through the channel is associated with renal injury and the induction of proteinuria (Moller et al., 2007 J Am Soc Nephrol 18:29-36 and Schlöndorff et al., 2009 Am J Physiol Cell Physiol 296: C558-69). In addition to Gain of Function mutations, it has been shown that expression of TRPC6 is elevated in human chronic kidney diseases including FSGS, minimal change disease, membraneous glomerulonephritis, and diabetic nephropathy (Moller et al., 2007 J Am Soc Nephrol 18:29-36 and Thilo et al., 2011 Nephrol. Dial. Transplant 27:921-9) as well as in mouse models of podocyte injury (Moller et al., 2007 J Am Soc Nephrol 18:29-36). TRPC6 deficient mice have been demonstrated to have reduced angiotensin II (Ang II)-induced albuminuria (Eckel et al., 2011 J Am Soc Nephrol 22:526-35) whereas transgenic podocyte-specific expression of human GoF mutations in mice induces albuminuria and glomerular lesions (Krall et al., 2010 PLoS ONE e12859 and Canales et al., 2015 Brit J Medicine Med Res 5:1198-1212). Consequently, inhibition of TRPC6 may be useful in the treatment of chronic kidney diseases. These findings not only suggest that TRPC6 normally functions to maintain proper kidney function, but also implicates TRPC6 as a specific cause of at least certain cases of FSGS. Based on the likely role of TRPC6 in kidney function, TRPC6 inhibitor compounds can be used in treating or ameliorating chronic kidney diseases or conditions caused (in whole or in part) by TRPC6 dysfunction. Additionally, TRPC6 inhibitor compounds can be used in treating or ameliorating symptoms of kidney diseases (e.g., hypertension, proteinuria, etc), regardless of the cause of the disease.

TRPC6 is expressed in the myometrium and placenta during pregnancy (Ku et al., 2006 J Soc Gynecol Investig 13:217-225; Clarson et al., 2003 J Physiol 550:515-528). As such TRPC6 may contribute to maintaining proper myogenic tone in the placenta and/or in maintaining proper fetal and maternal blood pressure during pregnancy.

Recent evidence has emerged implicating TRPC6 in certain forms of cancer. Several groups have established that TRPC6 expression is elevated in cells taken from patients with gliobastoma multiforme, the most frequent and incurable type of brain cancer (Chigurupati, et al., 2010 Cancer Res, 70:418-427; Ding et al., 2010 J Natl Cancer Inst. 102:1052-1068). Similarly, Ding et al. found elevated levels of TRPC6 in human glioma cells, and inhibition of TRPC6 pharmacologically or with a dominant-negative mutant suppressed cell growth in vitro. In two xenograft models of human gliomas, lentiviral-mediated expression of dominant-negative TRPC6 in the tumor cells prior subcutaneous or intracranial implantation reduced tumor volume when compared to controls (Ding et al., J. Natl. Cancer Inst. 2010, 102, 1052-1068). Increased levels of TRPC6 was also found to be associated with cervical cancer (Wan et al, 2012 Onco Targets Ther 5:171-176), breast cancer (Dhennin-Duthille et al., 2011 Cell Physiol Biochem 28:813-822), renal cell carcinoma (Song et al, 2013 Mol Biol Rep 40:5115-5122), head and neck squamous cell carcinoma (de Quiros, et al. 2013 BMC Cancer 13:116-127), and esophageal squamous cell carcinoma (Zhang et al., 2013 Med Oncol 30:607), among others. In hepatocellular carcinoma cells, it was demonstrated that doxorubicin, hypoxia, and ionizing radiation increased TRPC6 mRNA expression, and that TRPC6 is found at higher levels in tumor tissues than in the non-involved tissues. Elevated TRPC6 was associated with drug resistance which was diminished by TRPC6 RNA silencing in vitro. Lentiviral delivery of TRPC6 specific short hairpin RNA into Huh7 tumor cells prior to implantation in a mouse subcutaneous xenograft model reduced tumor growth and sensitized the tumors to doxorubicin (Wen et al., 2016 Sci Rep 6:23269). These findings suggest that TRPC6 may be a promising therapeutic target for cancer treatment.

Liver diseases including non-alcoholic steatohepatitis may be treated by reducing TRPC6 activity. Hypoxia increased TRPC6 expression in an human hepatic stellate cell line when compared to normoxic conditions. Using these cells, TRPC6 RNA silencing down-regulated transcripts for alpha smooth muscle actin and collagen 1A1, both of which are associated with fibrosis, in response to hypoxia (Iyer et al, 2015 Exp Cell Res 336:66-75).

Inhibition of TRPC6 may provide benefit to patients with Duchenne muscular dystrophy (DMD). In the mdx/utrn$^{+/-}$ model of DMD using isolated cardiomyoctes, TRPC6 deficiency restored the stress-stimulated contractility force and calcium transient response to normal when compared with mice possessing the wild-type TRPC6 gene, suggesting that TRPC6 inhibition will preserve cardiac function in DMD patients (Seo et al., 2014 Circ Res 114:823-32).

Fibrotic disorders may be treated with TRPC6 inhibitors. Overexpression of TRPC6 induced myofibroblast activation while deletion of TRPC6 reduced transforming growth factor beta-induced myofibroblast transformation. Furthermore, TRPC6 deficient mice demonstrated reduced dermal and cardiac wound healing (Davis et al., 2012 Dev Cell 23:705-15). TRPC6 deficient mice were also protected against bleomycin-induced lung fibrosis (Hofmann et al., 2017 Biochim Biophys Acta 1863:560-568).

TRPC6 inhibitors may be useful to reduce the rate of mortality in ARDS, sepsis, severe sepsis and septic shock since the survival rate in the mouse model of systemic sepsis (cecal ligation puncture, CLP) was significantly improved (80% vs 10% in the vehicle group) in TRPC6 deficient mice (Tauseef et al., 2012 J Exp Med 209: 1953-1968)

TRPC6 inhibitors may be useful for the treatment of pain. Spinal delivery of TRPC6 antisense oligonucleotides reduced hyperalgesia induced by mechanical, hypotonic, and thermal stimuli in preclinical pain models (Alexssandri-Haber et al., 2009 J Neurosci 29:6217-28).

Modulating a function of TRPC6 provides a means for modulating calcium homeostasis, sodium homeostasis, intracellular calcium levels, membrane polarization (resting membrane potential), and/or cation levels in a cell. Compounds that can modulate one or more TRPC6 functions are useful in many aspects including, but not limited to, maintaining calcium homeostasis; maintaining sodium homeostasis; modulating intracellular calcium levels; modulating membrane polarization (membrane potential); modulating cation levels; and/or treating or preventing diseases, disorders, or conditions associated with calcium homeostasis, sodium homeostasis, calcium or sodium dyshomeostasis, or membrane polarization/hyperpolarization (including hypo and hyperexcitability), and/or treating or preventing diseases, disorders, or conditions associated with regulation or dysregulation of TRPC6 expression or function.

BRIEF SUMMARY OF THE INVENTION

The present invention provides novel compounds that modulate TRPC6 and thus are useful for treating a variety of diseases and disorders that can be alleviated by modulating TRPC6 including hypertension, preeclampsia, restenosis, a cardiac or respiratory condition, renal disease, liver disease, muscular dystrophy, fibrotic disorders, pain, ischemia or ischemic reperfusion injury, and cancer. This invention also relates to pharmaceutical compositions comprising these compounds, methods of using these compounds in the treatment of various diseases and disorders, processes for preparing these compounds and intermediates useful in these processes.

In its broadest embodiment (embodiment one), the invention relates to a compound of formula (I)

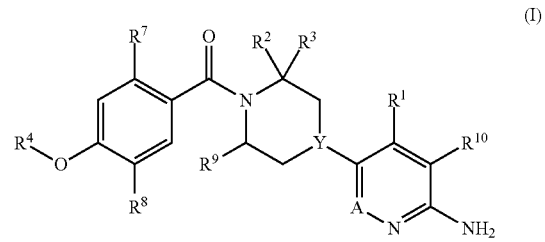

(I)

wherein
Y is CH or N;
A is CH or N;
$R^1$ is H, $C_{1-3}$alkyl, or $OC_{1-3}$alkyl;
$R^2$ is H, $C_{1-3}$alkyl or $C_{3-6}$cycloalkyl wherein each of the $C_{1-3}$alkyl or $C_{3-6}$cycloalkyl of the $R^2$ group may optionally be substituted with OH, halo or $OC_{1-3}$ alkyl;
$R^3$ is H or $C_{1-3}$ alkyl;
$R^2$ and $R^3$ together with the carbon atom to which they are attached may optionally join to form a 3- to 6-membered carbocyclic ring;
$R^4$ represents
 $C_{1-6}$ alkyl which may optionally be substituted with one to three groups independently selected from the group consisting of halo,
 $C_{3-6}$ cycloalkylmethyl and $C_{3-6}$ cycloalkylethyl, where the $C_{3-6}$ cycloalkyl of the $C_{3-6}$cycloalkylmethyl and $C_{3-6}$ cycloalkylethyl may optionally be substituted with one to three groups independently selected from the group consisting of halo and methyl,
 1,2,3-thiadiazolymethyl, thiazoylmethyl, isoxazolylmethyl or
 a group of formula:

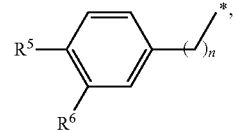

wherein n is 0 or 1;
$R^5$ is selected from the group consisting of H, halo, $CF_3$, $OCF_3$, CN, $C_{1-3}$ alkyl, $OC_{1-3}$ alkyl, $C_{3-6}$cycloalkyl; wherein each of the $C_{1-3}$ alkyl and $OC_{1-3}$ alkyl of the $R^5$ groups may optionally be substituted with one to three groups each independently selected from the group consisting of halo, oxo, $NH_2$, $NH(C_{1-3}$ alkyl), and $N(C_{1-3}$alkyl$)_2$;
$R^6$ is selected from the group consisting of H, halo, $C_{1-3}$ alkyl and $OC_{1-3}$ alkyl;
wherein
$R^5$ and $R^6$ may join to form a 5- or 6-membered carbocyclic ring wherein one or two carbon atoms of the 5- or 6-membered carbocyclic ring may optionally be replaced by one or two oxygen atoms;

$R^7$ is selected from the group consisting of H, halo, $C_{1-3}$ alkyl and $OC_{1-3}$ alkyl, wherein the $C_{1-3}$ alkyl of the $R^7$ group may optionally be substituted with one to three substituents selected from the group consisting of halo;

$R^8$ is selected from the group consisting of H and halo;

$R^9$ is H or $C_{1-3}$ alkyl; wherein $R^2$ and $R^9$ may join to form a bicyclic ring;

$R^{10}$ is H or $C_{1-3}$ alkyl;

or a pharmaceutically acceptable salt thereof.

In a second embodiment (embodiment two), the invention relates to a compound according to embodiment one, wherein Y is CH and A is N;

or a pharmaceutically acceptable salt thereof.

In a third embodiment (embodiment three), the invention relates to a compound according to embodiment one, wherein Y is CH and A is CH;

or a pharmaceutically acceptable salt thereof.

In a fourth embodiment (embodiment four), the invention relates to a compound according to embodiment one, wherein Y is N and A is CH;

or a pharmaceutically acceptable salt thereof.

In a fifth embodiment (embodiment five), the invention relates to a compound according to embodiment one, wherein Y is N and A is N;

or a pharmaceutically acceptable salt thereof.

In a sixth embodiment (embodiment six), the invention relates to a compound according to any one of embodiments one to five, wherein $R^4$ represents is group of formula:

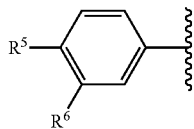

or a pharmaceutically acceptable salt thereof.

In a seventh embodiment (embodiment seven), the invention relates to a compound according to any one of embodiments one to six, wherein $R^5$ is selected from the group consisting of H, F, Cl, $CF_3$, $OCF_3$, CN, methyl, ethyl, isopropyl, methoxy, cyclopropyl, acetyl, and $(CH_3)_2NC(O)$—;

$R^6$ is selected from the group consisting of H, F, and methoxy;

wherein $R^5$ and $R^6$ may join to form a 5- or 6-membered carbocyclic ring two carbon atoms of the carbocyclic are replaced by two oxygen atoms;

or a pharmaceutically acceptable salt thereof.

In an eighth embodiment (embodiment eight), the invention relates to a compound according to embodiment one, wherein $R^4$, $R^5$ and $R^6$ collectively represent a group selected from the group selected from the group consisting of phenyl, 4-methylphenyl, 4-ethylphenyl, isopropylphenyl, 4-methoxyphenyl, 4-fluorophenyl, 4-chlorophenyl, 4-trifluoromethylphenyl, 4-trifluoromethoxyphenyl, 4-cyclopropylphenyl, benzonitrile, 4-N,N-dimethylbenzamide, and 4-acetylphenyl;

or a pharmaceutically acceptable salt thereof.

In a ninth embodiment (embodiment nine), the invention relates to a compound according to embodiment one, wherein $R^4$, $R^5$ and $R^6$ collectively represent phenyl;

or a pharmaceutically acceptable salt thereof.

In a tenth embodiment (embodiment ten), the invention relates to a compound according to any one of embodiments one, eight or nine, wherein $R^1$ to $R^3$ and $R^7$ to $R^{10}$ are each H;

or a pharmaceutically acceptable salt thereof.

In an eleventh embodiment (embodiment eleven), the invention relates to a compound according to any one of the embodiments one to five, wherein $R^4$ is $C_{1-6}$ alkyl;

or a pharmaceutically acceptable salt thereof.

In a twelfth embodiment (embodiment twelve), the invention relates to a compound according to any one of the embodiments one to five and eleven, wherein $R^4$ is selected from the group consisting of n-propyl and isopropyl;

or a pharmaceutically acceptable salt thereof.

In a thirteenth embodiment (embodiment thirteen), the invention relates to a compound according to any one of the embodiments one to five, wherein $R^4$ is $C_{3-6}$ cycloalkylmethyl or $C_{3-6}$cycloalkylethyl, wherein the $C_{3-6}$ cycloalkyl of the $C_{3-6}$ cycloalkylmethyl and $C_{3-6}$ cycloalkylethyl may optionally be substituted with one to three groups independently selected from the group consisting of halo, and methyl;

or a pharmaceutically acceptable salt thereof.

In a fourteenth embodiment (embodiment fourteen), the invention relates to a compound according to any one of the embodiments one to five and thirteen, wherein $R^4$ is selected from the group consisting of cyclopropylmethyl, cyclopropylethyl, 2-methylcyclopropylmethyl, cyclobutylmethyl, 3-methylcyclobutylmethyl, 3,3-difluorocyclobutylmethyl, and cyclohexylmethyl;

or a pharmaceutically acceptable salt thereof.

DETAILED DESCRIPTION OF THE INVENTION

Table 1 shows the compounds of the invention which can be made by the synthetic schemes and the examples shown in the Synthetic Examples section below, and known methods in the art.

| Cpd No. | Structure | Structure Name |
|---|---|---|
| 2 | 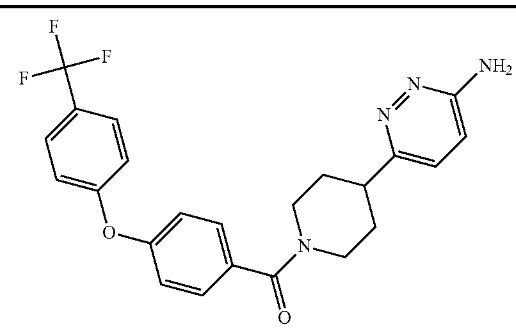 | 6-(1-{4-[4-(trifluoromethyl)phenoxy]benzoyl}piperidin-4-yl)pyridazin-3-amine |

-continued

| Cpd No. | Structure | Structure Name |
|---|---|---|
| 3 | 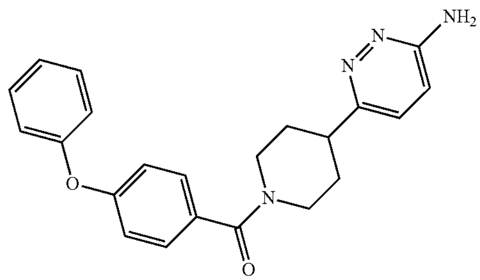 [SMILES: Nc1ccc(C2CCN(C(=O)c3ccc(Oc4ccccc4)cc3)CC2)nn1] | 6-[1-(4-phenoxybenzoyl)piperidin-4-yl]pyridazin-3-amine |
| 4 | 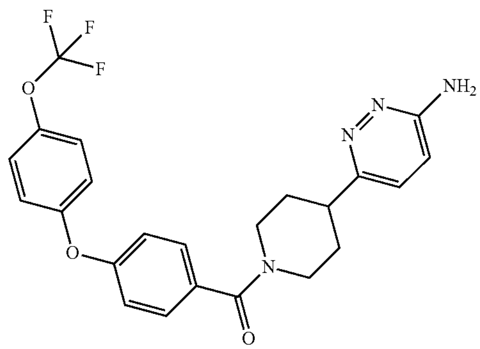 [SMILES: Nc1ccc(C2CCN(C(=O)c3ccc(Oc4ccc(OC(F)(F)F)cc4)cc3)CC2)nn1] | 6-(1-{4-[4-(trifluoromethoxy)phenoxy]benzoyl}piperidin-4-yl)pyridazin-3-amine |
| 5 | 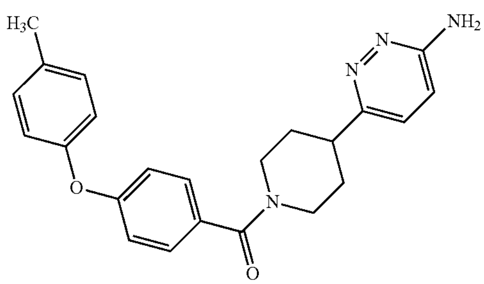 [SMILES: Cc1ccc(Oc2ccc(C(=O)N3CCC(c4ccc(N)nn4)CC3)cc2)cc1] | 6-{1-[4-(4-methylphenoxy)benzoyl]piperidin-4-yl}pyridazin-3-amine |
| 6 | 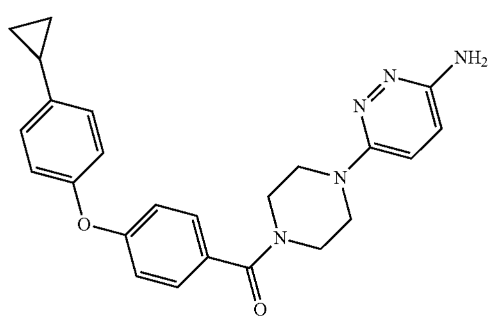 [SMILES: Nc1ccc(N2CCN(C(=O)c3ccc(Oc4ccc(C5CC5)cc4)cc3)CC2)nn1] | 6-{4-[4-(4-cyclopropylphenoxy)benzoyl]piperazin-1-yl}pyridazin-3-amine |
| 7 | 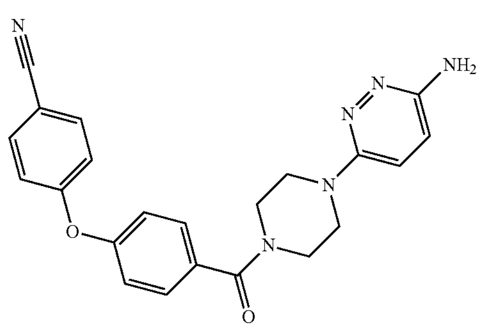 [SMILES: N#Cc1ccc(Oc2ccc(C(=O)N3CCN(c4ccc(N)nn4)CC3)cc2)cc1] | 4-{4-[4-(6-aminopyridazin-3-yl)piperazine-1-carbonyl]phenoxy}benzonitrile |

-continued

| Cpd No. | Structure | Structure Name |
|---|---|---|
| 8 | 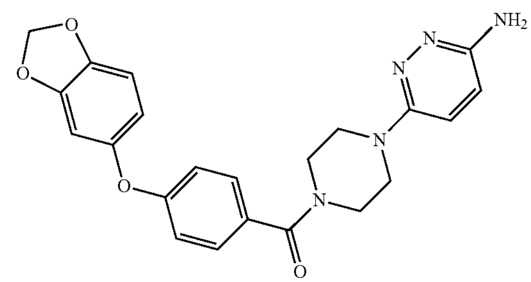 [SMILES: Nc1ccc(N2CCN(C(=O)c3ccc(Oc4ccc5c(c4)OCO5)cc3)CC2)nn1] | 6-{4-[4-(2H-1,3-benzodioxol-5-yloxy)benzoyl]piperazin-1-yl}pyridazin-3-amine |
| 9 | 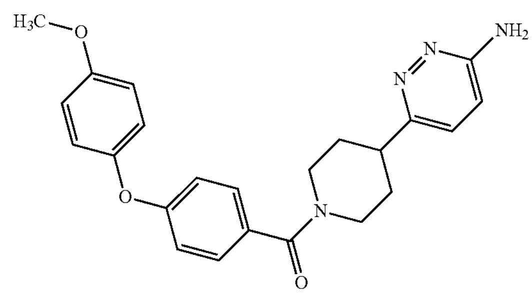 [SMILES: COc1ccc(Oc2ccc(C(=O)N3CCC(c4ccc(N)nn4)CC3)cc2)cc1] | 6-{1-[4-(4-methoxyphenoxy)benzoyl]piperidin-4-yl}pyridazin-3-amine |
| 10 | 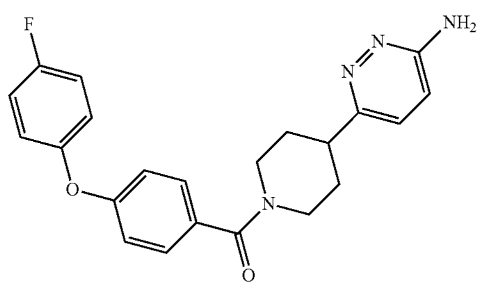 [SMILES: Nc1ccc(C2CCN(C(=O)c3ccc(Oc4ccc(F)cc4)cc3)CC2)nn1] | 6-{1-[4-(4-fluorophenoxy)benzoyl]piperidin-4-yl}pyridazin-3-amine |
| 11 | 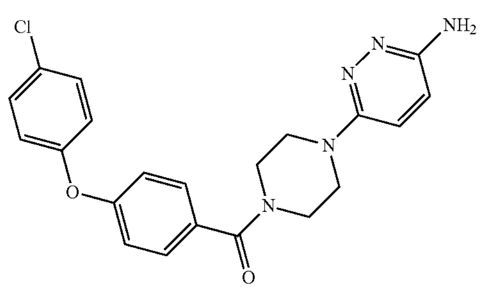 [SMILES: Nc1ccc(N2CCN(C(=O)c3ccc(Oc4ccc(Cl)cc4)cc3)CC2)nn1] | 6-{4-[4-(4-chlorophenoxy)benzoyl]piperazin-1-yl}pyridazin-3-amine |
| 12 | 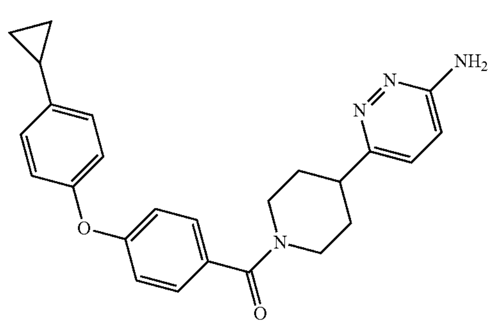 [SMILES: Nc1ccc(C2CCN(C(=O)c3ccc(Oc4ccc(C5CC5)cc4)cc3)CC2)nn1] | 6-{1-[4-(4-cyclopropylphenoxy)benzoyl]piperidin-4-yl}pyridazin-3-amine |

-continued

| Cpd No. | Structure | Structure Name |
|---|---|---|
| 13 | 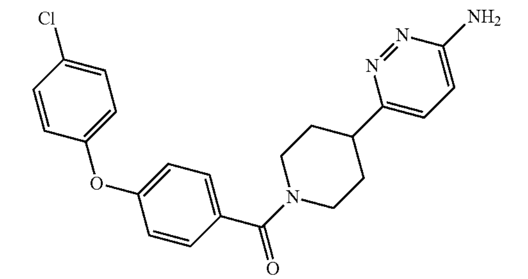 [SMILES: Nc1ccc(C2CCN(C(=O)c3ccc(Oc4ccc(Cl)cc4)cc3)CC2)nn1] | 6-{1-[4-(4-chlorophenoxy)benzoyl]piperidin-4-yl}pyridazin-3-amine |
| 14 | 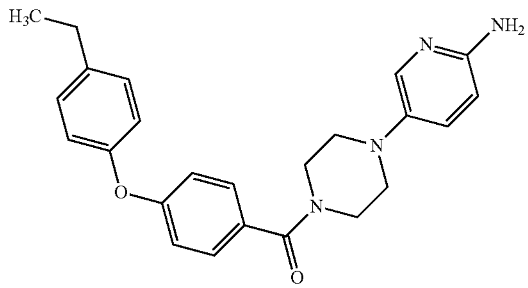 [SMILES: CCc1ccc(Oc2ccc(C(=O)N3CCN(c4ccc(N)nc4)CC3)cc2)cc1] | 5-{4-[4-(4-ethylphenoxy)benzoyl]piperazin-1-yl}pyridin-2-amine |
| 15 | 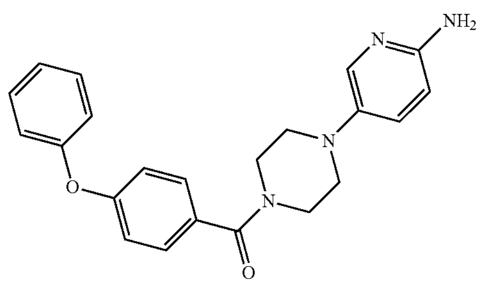 [SMILES: Nc1ccc(N2CCN(C(=O)c3ccc(Oc4ccccc4)cc3)CC2)cn1] | 5-[4-(4-phenoxybenzoyl)piperazin-1-yl]pyridin-2-amine |
| 16 | 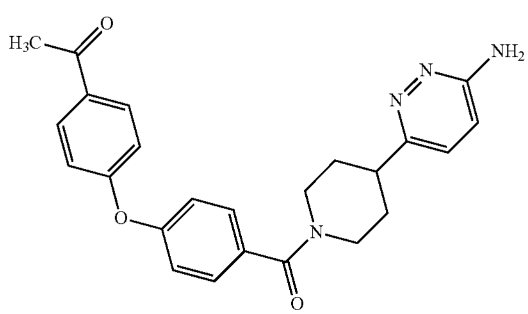 [SMILES: CC(=O)c1ccc(Oc2ccc(C(=O)N3CCC(c4ccc(N)nn4)CC3)cc2)cc1] | 1-(4-{4-[4-(6-aminopyridazin-3-yl)piperidine-1-carbonyl]phenoxy}phenyl)ethan-1-one |
| 17 | 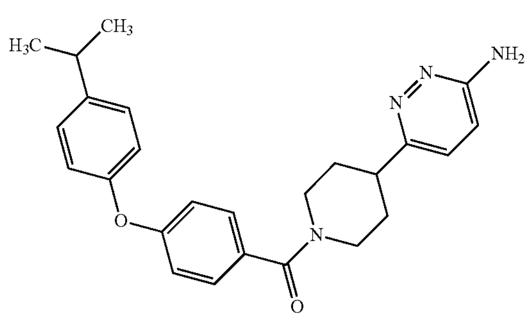 [SMILES: CC(C)c1ccc(Oc2ccc(C(=O)N3CCC(c4ccc(N)nn4)CC3)cc2)cc1] | 6-(1-{4-[4-(propan-2-yl)phenoxy]benzoyl}piperidin-4-yl)pyridazin-3-amine |

-continued

| Cpd No. | Structure | Structure Name |
|---|---|---|
| 18 | 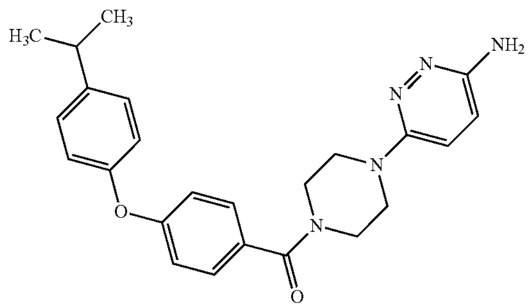 [SMILES: CC(C)c1ccc(Oc2ccc(C(=O)N3CCN(c4ccc(N)nn4)CC3)cc2)cc1] | 6-(4-{4-[4-(propan-2-yl)phenoxy]benzoyl}piperazin-1-yl)pyridazin-3-amine |
| 19 | 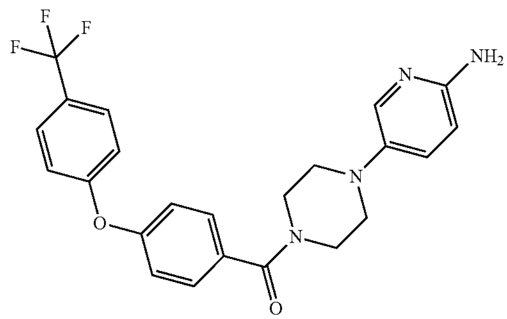 [SMILES: Nc1ccc(N2CCN(C(=O)c3ccc(Oc4ccc(C(F)(F)F)cc4)cc3)CC2)cn1] | 5-(4-{4-[4-(trifluoromethyl)phenoxy]benzoyl}piperazin-1-yl)pyridin-2-amine |
| 20 | 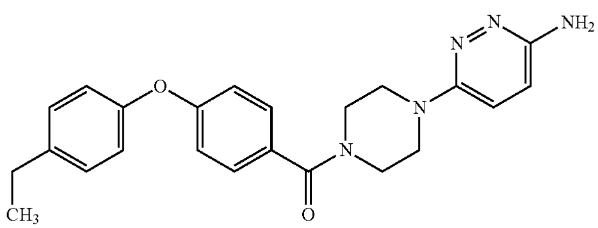 [SMILES: CCc1ccc(Oc2ccc(C(=O)N3CCN(c4ccc(N)nn4)CC3)cc2)cc1] | 6-{4-[4-(4-ethylphenoxy)benzoyl]piperazin-1-yl}pyridazin-3-amine |
| 21 | 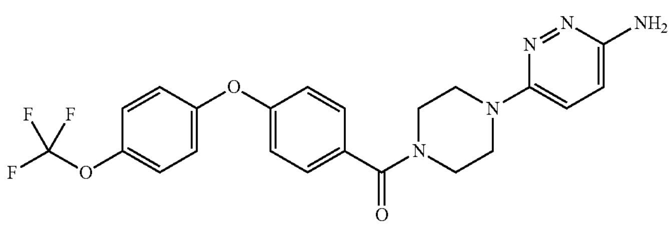 [SMILES: Nc1ccc(N2CCN(C(=O)c3ccc(Oc4ccc(OC(F)(F)F)cc4)cc3)CC2)nn1] | 6-(4-{4-[4-(trifluoromethoxy)phenoxy]benzoyl}piperazin-1-yl)pyridazin-3-amine |
| 22 | 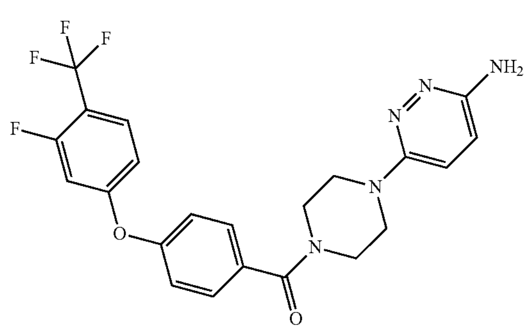 [SMILES: Nc1ccc(N2CCN(C(=O)c3ccc(Oc4ccc(C(F)(F)F)c(F)c4)cc3)CC2)nn1] | 6-(4-{4-[3-fluoro-4-(trifluoromethyl)phenoxy]benzoyl}piperazin-1-yl)pyridazin-3-amine |

-continued

| Cpd No. | Structure | Structure Name |
|---|---|---|
| 23 | 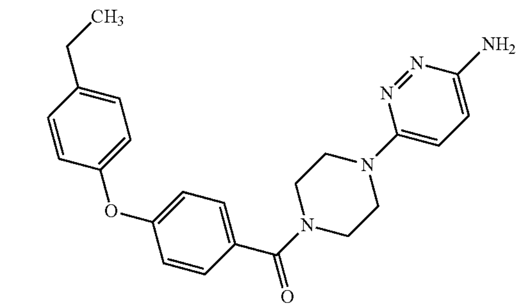 [SMILES: CCc1ccc(Oc2ccc(C(=O)N3CCN(c4ccc(N)nn4)CC3)cc2)cc1] | 6-{1-[4-(4-ethylphenoxy)benzoyl]piperidin-4-yl}pyridazin-3-amine |
| 24 | 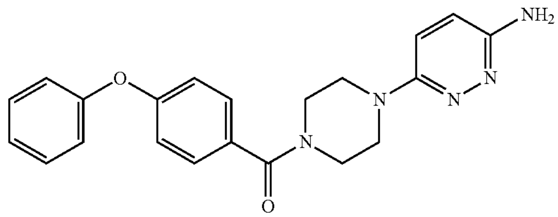 [SMILES: Nc1ccc(N2CCN(C(=O)c3ccc(Oc4ccccc4)cc3)CC2)nn1] | 6-[4-(4-phenoxybenzoyl)piperazin-1-yl]pyridazin-3-amine |
| 25 | 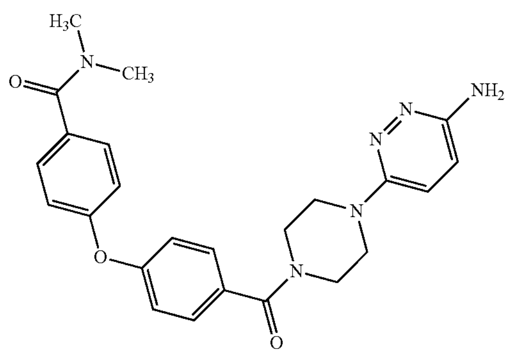 [SMILES: CN(C)C(=O)c1ccc(Oc2ccc(C(=O)N3CCN(c4ccc(N)nn4)CC3)cc2)cc1] | 4-{4-[4-(6-aminopyridazin-3-yl)piperazine-1-carbonyl]phenoxy}-N,N-dimethylbenzamide |
| 26 | 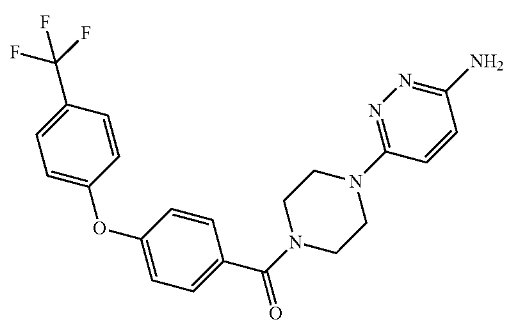 [SMILES: Nc1ccc(N2CCN(C(=O)c3ccc(Oc4ccc(C(F)(F)F)cc4)cc3)CC2)nn1] | 6-(4-{4-[4-(trifluoromethyl)phenoxy]benzoyl}piperazin-1-yl)pyridazin-3-amine |
| 27 | 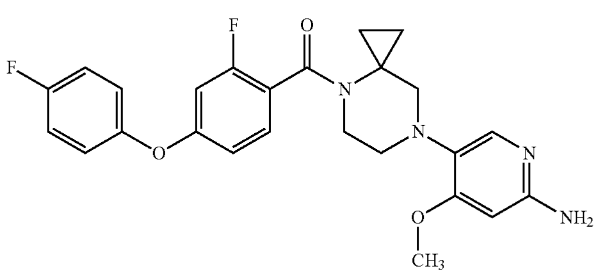 [SMILES: COc1cc(N)ncc1N1CCN(C(=O)c2ccc(Oc3ccc(F)cc3)cc2F)C2(CC2)C1] | 5-{4-[2-Fluoro-4-(4-fluorophenoxy)benzoyl]-4,7-diazaspiro[2.5]octan-7-yl}-4-methoxypyridin-2-amine |

-continued

| Cpd No. | Structure | Structure Name |
|---|---|---|
| 28 | 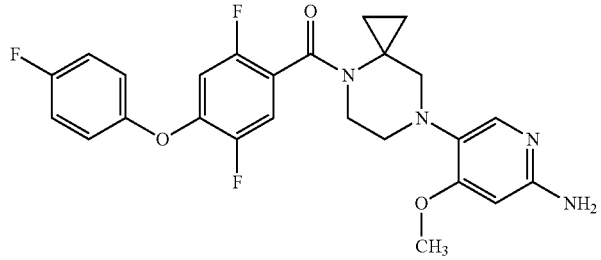 [SMILES: COc1cc(N)ncc1N1CCN(C(=O)c2cc(F)c(Oc3ccc(F)cc3)cc2F)C2(CC2)C1] | 5-{4-[2,5-Difluoro-4-(4-fluorophenoxy)benzoyl]-4,7-diazaspiro[2.5]octan-7-yl}-4-methoxypyridin-2-amine |
| 29 | 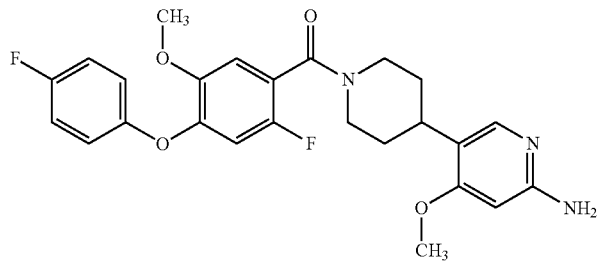 [SMILES: COc1cc(C(=O)N2CCC(c3cnc(N)cc3OC)CC2)c(F)cc1Oc1ccc(F)cc1] | 5-{1-[2-Fluoro-4-(4-fluorophenoxy)-5-methoxybenzoyl]piperidin-4-yl}-4-methoxypyridin-2-amine |
| 30 | 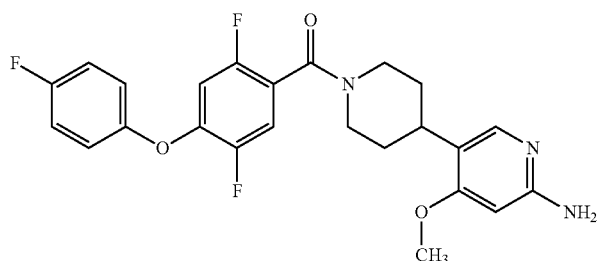 | 5-{1-[2,5-difluoro-4-(4-fluorophenoxy)benzoyl]piperidin-4-yl}-4-methoxypyridin-2-amine |
| 31 | 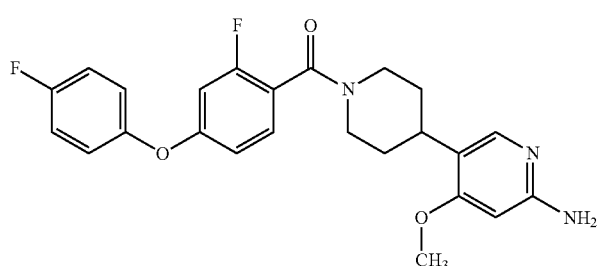 | 5-{1-[2-Fluoro-4-(4-fluorophenoxy)benzoyl]piperidin-4-yl}-4-methoxypyridin-2-amine |
| 32 | 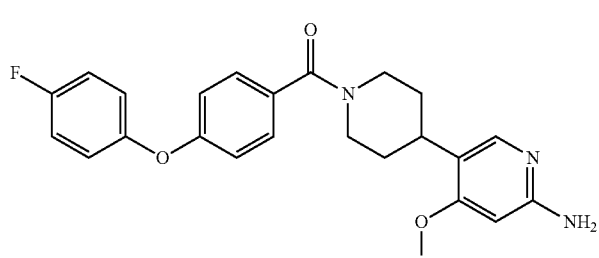 | 5-{1-[4-(4-Fluorophenoxy)benzoyl]piperidin-4-yl}-4-methoxypyridin-2-amine |
| 33 | 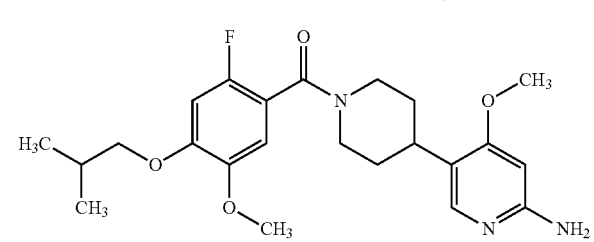 [SMILES: COc1cc(C(=O)N2CCC(c3cnc(N)cc3OC)CC2)c(F)cc1OCC(C)C] | 5-{1-[2-Fluoro-5-methoxy-4-(2-methylpropoxy)benzoyl]-piperidin-4-yl}-4-methoxypyridin-2-amine |

| Cpd No. | Structure Name |
|---|---|
| 34 | 5-(1-{2-Fluoro-5-methoxy-4-[(3-methylcyclobutyl)methoxy]benzoyl}piperidin-4-yl)-4-methoxypyridin-2-amine |
| 35 | 5-{1-[4-(Cyclopropylmethoxy)-2-fluoro-5-methoxybenzoyl]piperidin-4-yl}-4-methoxypyridin-2-amine |
| 36 | 5-{1-[4-(Cyclobutylmethoxy)-2-fluoro-5-methoxybenzoyl]piperidin-4-yl}-4-methoxypyridin-2-amine |
| 37 | 5-(1-{4-[(3,3-Difluorocyclobutyl)methoxy]-2-fluoro-5-methoxybenzoyl}piperidin-4-yl)-4-methoxypyridin-2-amine |
| 38 | 5-[1-(2-Fluoro-4-{[trans-2-methylcyclopropyl]methoxy}benzoyl)piperidin-4-yl]-4-methoxypyridin-2-amine |
| 39 | 5-[1-(2-Fluoro-4-propoxybenzoyl)piperidin-4-yl]-4-methoxypyridin-2-amine |

-continued

| Cpd No. | Structure | Structure Name |
|---|---|---|
| 40 | 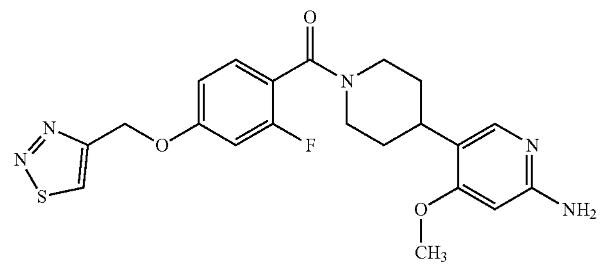 [SMILES: COc1cc(N)ncc1C1CCN(C(=O)c2ccc(OCc3csnn3)cc2F)CC1] | 5-(1-{2-Fluoro-4-[(1,2,3-thiadiazol-4-yl)methoxy]benzoyl}piperidin-4-yl)-4-methoxypyridin-2-amine |
| 41 | 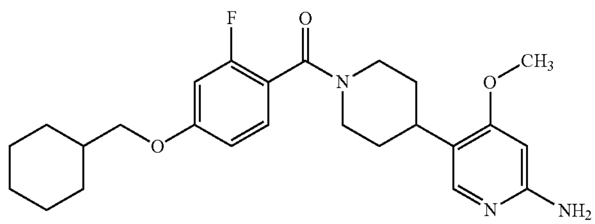 [SMILES: COc1cc(N)ncc1C1CCN(C(=O)c2ccc(OCC3CCCCC3)cc2F)CC1] | 5-{1-[4-(Cyclohexylmethoxy)-2-fluorobenzoyl]piperidin-4-yl}-4-methoxypyridin-2-amine |
| 42 | 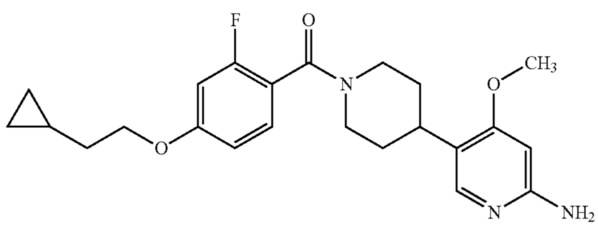 [SMILES: COc1cc(N)ncc1C1CCN(C(=O)c2ccc(OCCC3CC3)cc2F)CC1] | 5-{1-[4-(2-Cyclopropylethoxy)-2-fluorobenzoyl]piperidin-4-yl}-4-methoxypyridin-2-amine |
| 43 | 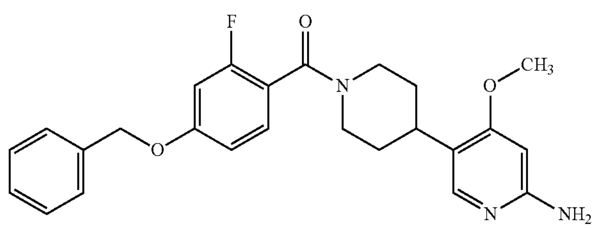 [SMILES: COc1cc(N)ncc1C1CCN(C(=O)c2ccc(OCc3ccccc3)cc2F)CC1] | 5-{1-[4-(Benzyloxy)-2-fluorobenzoyl]piperidin-4-yl}-4-methoxypyridin-2-amine |
| 44 | 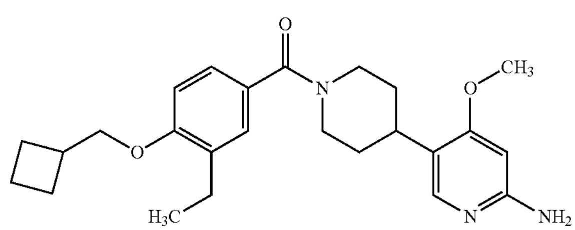 [SMILES: CCc1cc(C(=O)N2CCC(c3cnc(N)cc3OC)CC2)ccc1OCC1CCC1] | 5-{1-[4-(Cyclobutylmethoxy)-3-methoxybenzoyl]piperidin-4-yl}-4-methoxypyridin-2-amine |
| 45 | 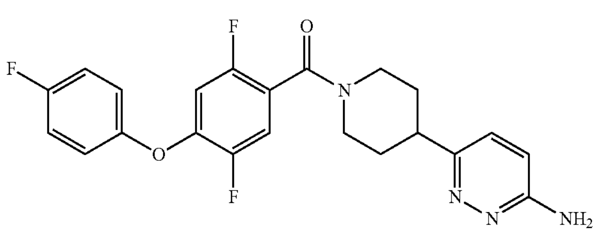 [SMILES: Nc1ccc(C2CCN(C(=O)c3cc(F)c(Oc4ccc(F)cc4)cc3F)CC2)nn1] | 6-{1-[2,5-Difluoro-4-(4-fluorophenoxy)benzoyl]piperidin-4-yl}pyridazin-3-amine |

| Cpd No. | Structure | Structure Name |
|---|---|---|
| 46 | 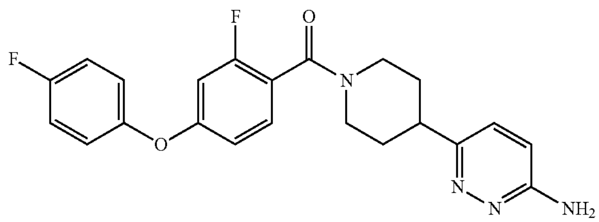 [SMILES: Nc1ccc(C2CCN(C(=O)c3ccc(Oc4ccc(F)cc4)cc3F)CC2)nn1] | 6-{1-[2-Fluoro-4-(4-fluorophenoxy)benzoyl]piperidin-4-yl}pyridazin-3-amine |
| 47 | 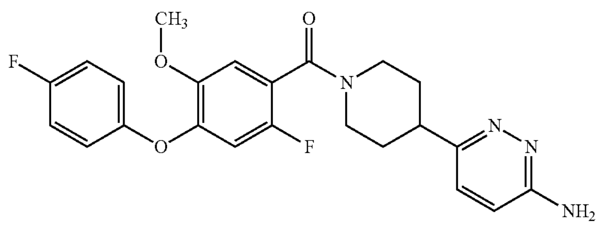 [SMILES: COc1cc(C(=O)N2CCC(c3ccc(N)nn3)CC2)c(F)cc1Oc1ccc(F)cc1] | 6-{1-[2-Fluoro-4-(4-fluorophenoxy)-5-methoxybenzoyl]piperidin-4-yl}pyridazin-3-amine |
| 48 | 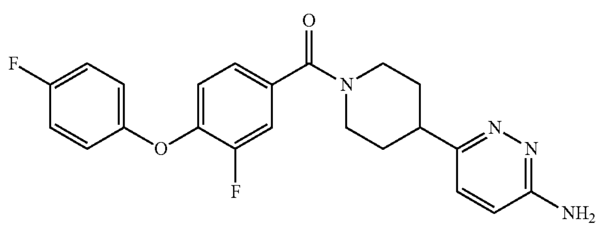 [SMILES: Nc1ccc(C2CCN(C(=O)c3ccc(Oc4ccc(F)cc4)c(F)c3)CC2)nn1] | 6-{1-[3-Fluoro-4-(4-fluorophenoxy)benzoyl]piperidin-4-yl}pyridazin-3-amine |
| 49 | 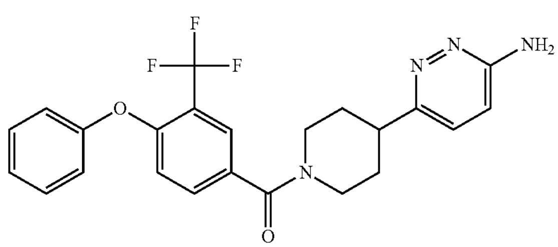 [SMILES: Nc1ccc(C2CCN(C(=O)c3ccc(Oc4ccccc4)c(C(F)(F)F)c3)CC2)nn1] | 6-{1-[4-Phenoxy-3-(trifluoromethyl)benzoyl]piperidin-4-yl}pyridazin-3-amine |
| 50 | 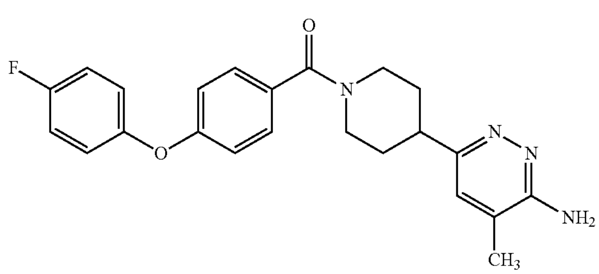 [SMILES: Cc1cc(C2CCN(C(=O)c3ccc(Oc4ccc(F)cc4)cc3)CC2)nnc1N] | 6-{1-[4-(4-Fluorophenoxy)benzoyl]piperidin-4-yl}-4-methylpyridazin-3-amine |
| 51 | 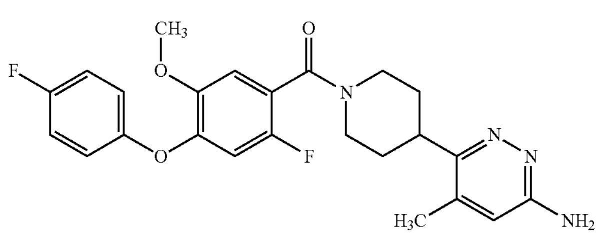 [SMILES: COc1cc(C(=O)N2CCC(c3nnc(N)cc3C)CC2)c(F)cc1Oc1ccc(F)cc1] | 6-{1-[2-Fluoro-4-(4-fluorophenoxy)-5-methoxybenzoyl]piperidin-4-yl}-5-methylpyridazin-3-amine |

| Cpd No. | Structure | Structure Name |
|---|---|---|
| 52 | 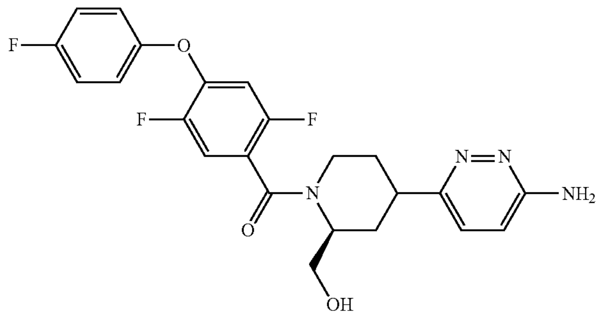 [SMILES: Nc1ccc(C2CCN(C(=O)c3cc(F)c(Oc4ccc(F)cc4)cc3F)[C@H](CO)C2)nn1] | [(2S)-4-(6-Aminopyridazin-3-yl)-1-[2,5-difluoro-4-(4-fluorophenoxy)benzoyl]piperidin-2-yl]methanol |
| 53 | 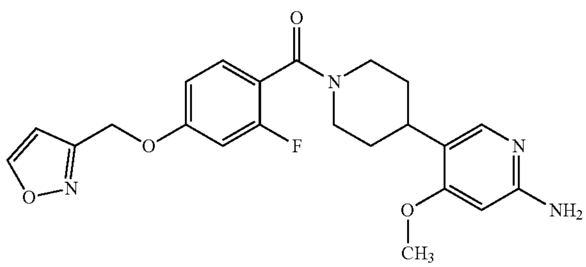 [SMILES: COc1cc(N)ncc1C1CCN(C(=O)c2ccc(OCc3ccon3)cc2F)CC1] | 5-(1-{2-Fluoro-4-[(1,2-oxazol-3-yl)methoxy]benzoyl}piperidin-4-yl)-4-methoxypyridin-2-amine |
| 54 | 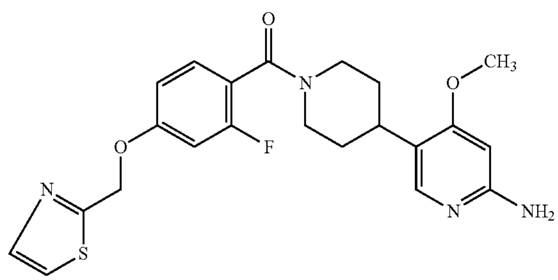 [SMILES: COc1cc(N)ncc1C1CCN(C(=O)c2ccc(OCc3nccs3)cc2F)CC1] | 5-(1-{2-Fluoro-4-[(1,3-thiazol-2-yl)methoxy]benzoyl}piperidin-4-yl)-4-methoxypyridin-2-amine |

In an embodiment, the invention relates to any of the compounds 1 to 54 depicted in Table 1 above and the pharmaceutically acceptable salts thereof.

Unless specifically indicated, throughout the specification and the appended claims, a given chemical formula or name shall encompass tautomers and all stereo, optical and geometrical isomers (e.g. enantiomers, diastereomers, E/Z isomers, etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

In the groups, radicals, or moieties defined below, the number of carbon atoms is often specified preceding the group, for example, $C_{1-6}$-alkyl means an alkyl group or radical having 1 to 6 carbon atoms. In general in groups like HO, $H_2N$, (O)S, (O)$_2$S, NC (cyano), HOOC, $F_3C$ or the like, the skilled artisan can see the radical attachment point(s) to the molecule from the free valences of the group itself. For combined groups comprising two or more subgroups, the last named subgroup is the radical attachment point, for example, the substituent "aryl-$C_{1-3}$-alkyl" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail.

The symbol

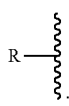

may be used in sub-formulas to indicate the bond which is connected to the core molecule as defined, for example,

R—⟨

The term "substituted" as used herein, means that any one or more hydrogens on the designated atom is replaced with a selection from the indicated group, provided that the designated atom's normal valence is not exceeded, and that the substitution results in a stable compound.

Enantiomerically pure compounds of this invention or intermediates may be prepared via asymmetric synthesis, for example by preparation and subsequent separation of appropriate diasteromeric compounds or intermediates which can be separated by known methods (e.g. by chromatographic separation or crystallization) and/or by using chiral reagents, such as chiral starting materials, chiral catalysts or chiral auxiliaries.

Further, it is known to the person skilled in the art how to prepare enantiomerically pure compounds from the corresponding racemic mixtures, such as by chromatographic separation of the corresponding racemic mixtures on chiral stationary phases; or by resolution of a racemic mixture using an appropriate resolving agent, e.g. by means of diastereomeric salt formation of the racemic compound with optically active acids or bases, subsequent resolution of the salts and release of the desired compound from the salt; or by derivatization of the corresponding racemic compounds with optically active chiral auxiliary reagents, subsequent diastereomer separation and removal of the chiral auxiliary group; or by kinetic resolution of a racemate (e.g. by enzymatic resolution); by enantioselective crystallization from a conglomerate of enantiomorphous crystals under suitable conditions; or by (fractional) crystallization from a suitable solvent in the presence of an optically active chiral auxiliary.

The invention includes pharmaceutically acceptable derivatives of compounds of the invention. A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the invention.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include acetates, ascorbates, benzenesulfonates, benzoates, besylates, bicarbonates, bitartrates, bromides/hydrobromides, edetates, camsylates, carbonates, chlorides/hydrochlorides, citrates, edisylates, ethane disulfonates, estolates esylates, fumarates, gluceptates, gluconates, glutamates, glycolates, glycollylarsnilates, hexylresorcinates, hydrabamines, hydroxymaleates, hydroxynaphthoates, iodides, isothionates, lactates, lactobionates, malates, maleates, mandelates, methanesulfonates, methylbromides, methylnitrates, methylsulfates, mucates, napsylates, nitrates, oxalates, pamoates, pantothenates, phenylacetates, phosphates/diphosphates, polygalacturonates, propionates, salicylates, stearates, subacetates, succinates, sulfamides, sulfates, tannates, tartrates, teoclates, toluenesulfonates, triethiodides, ammonium, benzathines, chloroprocaines, cholines, diethanolamines, ethylenediamines, meglumines and procaines. Further pharmaceutically acceptable salts can be formed with cations from metals like aluminium, calcium, lithium, magnesium, potassium, sodium, zinc and the like. (See also Pharmaceutical salts, Birge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts) also comprise a part of the invention.

In addition, within the scope of the invention is use of prodrugs of compounds of the invention. Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

Compounds of the invention also include their isotopically-labelled forms. An isotopically-labelled form of an active agent of a combination of the present invention is identical to said active agent but for the fact that one or more atoms of said active agent have been replaced by an atom or atoms having an atomic mass or mass number different from the atomic mass or mass number of said atom which is usually found in nature. Examples of isotopes which are readily available commercially and which can be incorporated into an active agent of a combination of the present invention in accordance with well established procedures, include isotopes of hydrogen, carbon, nitrogen, oxygen, phosphorous, fluorine and chlorine, e.g., $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. An active agent of a combination of the present invention, a prodrug thereof, or a pharmaceutically acceptable salt of either which contains one or more of the above-mentioned isotopes and/or other isotopes of other atoms is contemplated to be within the scope of the present invention.

The term halogen generally denotes fluorine, chlorine, bromine and iodine

The term "$C_{1-n}$-alkyl", wherein n is an integer selected from 2, 3, 4, 5 or 6, preferably 4 or 6, either alone or in combination with another radical denotes an acyclic, saturated, branched or linear hydrocarbon radical with 1 to n C atoms. For example the term $C_{1-5}$-alkyl embraces the radicals $H_3C-$, $H_3C-CH_2-$, $H_3C-CH_2-CH_2-$, $H_3C-CH(CH_3)-$, $H_3C-CH_2-CH_2-CH_2-$, $H_3C-CH_2-CH(CH_3)-$, $H_3C-CH(CH_3)-CH_2-$, $H_3C-C(CH_3)_2-$, $H_3C-CH_2-CH_2-CH_2-CH_2-$, $H_3C-CH_2-CH_2-CH(CH_3)-$, $H_3C-CH_2-CH(CH_3)-CH_2-$, $H_3C-CH(CH_3)-CH_2-CH_2-$, $H_3C-CH_2-C(CH_3)_2-$, $H_3C-C(CH_3)_2-CH_2-$, $H_3C-CH(CH_3)-CH(CH_3)-$ and $H_3C-CH_2-CH(CH_2CH_3)-$.

The term "$C_{3-n}$-cycloalkyl", wherein n is an integer from 4 to n, either alone or in combination with another radical denotes a cyclic, saturated, unbranched hydrocarbon radical with 3 to n C atoms. For example, the term $C_{3-6}$-cycloalkyl includes cyclopropyl, cyclobutyl, cyclopentyl, and cyclohexyl.

By the term "halo" added to an "alkyl", "alkylene" or "cycloalkyl" group (saturated or unsaturated) is such a alkyl or cycloalkyl group wherein one or more hydrogen atoms are replaced by a halogen atom selected from among fluorine, chlorine or bromine, preferably fluorine and chlorine, particularly preferred is fluorine. Examples include: $H_2FC-$, $HF_2C-$, $F_3C-$.

The term "carbocyclyl" as used either alone or in combination with another radical, means a mono- bi- or tricyclic ring structure consisting of 3 to 9 carbon atoms and optionally a heteroatom selected from the group consisting of N, O, and S. The term "carbocyclyl" refers to fully saturated ring systems and encompasses fused, bridged and spirocyclic systems.

Many of the terms given above may be used repeatedly in the definition of a formula or group and in each case have one of the meanings given above, independently of one another.

The compounds of the invention are only those which are contemplated to be 'chemically stable' as will be appreciated by those skilled in the art. For example, a compound which would have a 'dangling valency', or a 'carbanion' are not compounds contemplated by the inventive methods disclosed herein.

For all compounds disclosed herein above in this application, in the event the nomenclature is in conflict with the structure, it shall be understood that the compound is defined by the structure.

The present application provides compounds that can modulate TRPC6 function. Methods employing these compounds are also provided. Certain embodiments provide a method of modulating a TRPC6 function in a cell or animal comprising administering an effective amount of a compound that inhibits a TRPC6 function, wherein the compound inhibits a TRPC6-mediated ion flux. Certain embodiments provide a method of modulating a TRPC6 function in a cell or animal comprising administering an effective amount of a compound that inhibits a TRPC6 function, wherein the compound inhibits a TRPC6-mediated calcium influx. Certain embodiments provide a method of modulating a TRPC6 function in a cell or animal comprising administering an effective amount of a compound that inhibits a TRPC6 function, wherein the compound inhibits a TRPC6-mediated cytoskeletal reorganization or alteration in cell morphology. Certain embodiments provide a method of modulating a TRPC6 function in a cell comprising administering to the cell an effective amount of a compound that inhibits TRPC6 function, wherein the compound inhibits outward current mediated by TRPC6. Certain embodiments provide a method of modulating a TRPC6 function in a cell comprising administering to the cell an effective amount of a compound that inhibits TRPC6 function, wherein the compound inhibits inward current mediated by TRPC6. Certain embodiments provide a method of modulating a TRPC6 function in a cell comprising administering to the cell an effective amount of a compound that inhibits TRPC6 function, wherein the compound inhibits both the inward and outward currents mediated by TRPC6. Certain embodiments provide a method of modulating a TRPC6 function in a cell comprising administering to the cell an effective amount of a compound that inhibits TRPC6 function, wherein the compound inhibits TRPC6 mediated increases in intracellular calcium concentration. Certain embodiments provide a method of modulating a TRPC6 function in a cell comprising administering to the cell an effective amount of a compound that inhibits TRPC6 function, wherein the compound inhibits alterations in cell morphology. Certain embodiments also provide a method of preventing or treating a disease or condition related to TRPC6 function in a subject comprising administering to the subject a therapeutically effective amount of a compound that inhibits TRPC6 function, wherein the compound inhibits the inward current mediated by TRPC6. Certain embodiments provide a method of preventing or treating a disease or condition related to TRPC6 function in a subject comprising administering to the subject a therapeutically effective amount of a compound that inhibits TRPC6 function, wherein the compound inhibits the outward current mediated by TRPC6. Certain embodiments also provide a method of preventing or treating a disease or condition related to TRPC6 function in a subject comprising administering to the subject a therapeutically effective amount of a compound that inhibits TRPC6 function, wherein the compound inhibits both the inward and outward current mediated by TRPC6. Certain embodiments provide a method of preventing or treating a disease or condition related to TRPC6 function in a subject comprising administering to the subject a therapeutically effective amount of a compound that inhibits TRPC6 function, wherein the compound inhibits the ion flux mediated by TRPC6. Note that inhibition of a particular current refers to the ability of a compound to inhibit that current (e.g., inward and/or outward) in either an in vitro or an in vivo assay. Inhibition of a particular current in either an in vivo or an in vitro assay serves as a proxy for the particular functional activity of the particular compound.

The present invention provides methods of treating a TRPC6 mediated disorder in a subject, the method comprising administering an effective amount of a compound of the invention wherein each of the variables above are described herein, for example, in the detailed description below.

The present invention further provides a method for treating a TRPC6 mediated disorder in a subject, wherein the method comprises administering a composition comprising a compound of the invention and a pharmaceutically acceptable excipient, diluent or carrier.

The present invention further provides a method for treating a TRPC6 mediated disorder in a subject, wherein the method comprises administering a composition comprising a compound of the invention and a pharmaceutically acceptable excipient, diluent or carrier, and the TRPC6 mediated disorder is selected from cardiac hypertrophy, ischemia, ischemic reperfusion injury, hypertension, pulmonary arterial hypertension, idiopathic pulmonary arterial hypertension, restenosis, chronic obstructive pulmonary disease, cystic fibrosis, Alzheimer's disease, Parkinson's disease, Huntington's disease, amyotrophic lateral sclerosis (ALS), trauma induced brain disorders, asthma, rheumatoid arthritis, osteoarthritis, inflammatory bowel disease, multiple sclerosis, muscular dystrophy, Duchenne muscular dystrophy (Duchenne syndrome), preeclampsia and pregnancy-induced hypertension, non-alcoholic steatohepatitis, nephrotic syndrome including minimal change disease, focal segmental glomerulosclerosis (FSGS), and membranous glomerulonephritis, rapidly progressive glomerulonephritis, diabetic nephropathy or diabetic kidney disease (DKD), chronic kidney disease, hypertensive nephropathy, systemic lupus erythematosus (SLE), renal insufficiency, end stage renal disease, ischemia or an ischemic reperfusion injury, cancer, diabetes, idiopathic pulmonary fibrosis (IPF), emphysema and acute respiratory disease syndrome (ARDS), sepsis, severe sepsis and septic shock.

LIST OF ABBREVIATIONS

The following table shows abbreviations used and their definitions.

| | |
|---|---|
| ACN or MeCN | Acetonitrile |
| aq. | Aqueous |
| BEH | Ethylene Bridged Hybrid phase |
| Boc | tert-Butyloxycarbonyl |
| ° C. | Degree Celsius |
| CPhos-Pd-3G | Methanesulfonato(2-dicyclohexylphosphino-2',6'-bis(dimethylamino)-1,1'-biphenyl)(2'-amino-1,1'-biphenyl-2-yl)palladium(II) |
| DCM | Dichloromethane |
| DIPEA | N,N-diisopropylethylamine |
| DMA | N,N-dimethylacetamide |
| DMF | N,N-dimethylformamide |
| DMSO | Dimethylsulfoxide |
| DTAD | Di-tert-butyl azodicarboxylate |
| EDCI*HCl | 1-Ethyl-3-(3-dimethylaminopropyl)carbodiimide hydrochloride |
| Et | Ethyl |
| $Et_2O$ | Diethyl ether |
| EtOAc or EE | Ethyl acetate |
| EtOH | Ethanol |
| Grubbs catalyst $2^{nd}$ Gen. | (1,3-Bis(2,4,6-trimethylphenyl)-2-imidazolidinylidene)dichloro-(phenylmethylene)-(tricyclohexylphosphine)ruthenium |
| h | hour |
| $H_2$ | Hydrogen |
| HATU | O-(7-azabenzotriazol-1-yl)-N,N,N',N'-tetramethyl-uronium hexafluorophosphate |
| HCl | Hydrogen chloride |
| HPLC | High performance liquid chromatography |
| IPA | Isopropyl alcohol |
| LiHMDS | Lithium bis(trimethylsilyl)amine |
| LiOH | Lithium hydroxide |
| Me | Methyl |
| MeOH | Methanol |
| min | Minutes |
| MS | Mass spectrometry |
| MTBE | Methyl-tert.-butyl ether |
| m/z | Mass-to-charge ratio |
| NaOH | Sodium hydroxide |
| $NH_4OH$ | Solution of $NH_3$ in water |
| NMP | N-Methyl-2-pyrrolidinone |
| $Pd_2(dba)_3$ | Tris(dibenzylideneacetone)dipalladium(0) |
| Pd/C | Palladium on carbon |
| PE | Petroleum ether |
| psi | pound per square inch |
| RP | Reversed phase |
| $R_t$ | retention time (HPLC) |
| RT or rt | Room temperature |
| Ruphos Pd G3 | (2-Dicyclohexylphosphino-2',6'-diisopropoxy-1,1'-biphenyl)[2-(2'-amino-1,1'-biphenyl)palladium(II) methanesulfonate |
| $scCO_2$ | Supercritical carbon dioxide |
| SFC | Supercritical fluid chromatography |
| TBTU | Benzotriazolyl tetramethyluronium tetrafluoroborate |
| TEA | triethylamine |
| Tetrakis | Tetrakis(triphenylphosphine) palladium(0) |
| TFA | trifluoroacetic acid |
| THF | tetrahydrofuran |
| TLC | thin layer chromatography |
| TPP | Triphenylphosphine |
| Xantphos | 4,5-Bis(diphenylphosphino)-9,9-dimethylxanthene |
| Xphos | 2-Dicyclohexylphosphino-2',4',6'-triisopropyl-1,1'-biphenyl |
| Xphos $2^{nd}$ generation catalyst | Chloro(2-dicyclohexylphosphino-2',4',6'-triisopropyl-1,1'-biphenyl)[2-(2'-amino-1,1'-biphenyl)]palladium(II) |

SYNTHETIC EXAMPLES

The examples which follow are illustrative and, as recognized by one skilled in the art, particular reagents or conditions could be modified as needed for individual compounds without undue experimentation.

The following are examples of intermediates that are commercially available. These Examples are for the purpose of supporting the embodiments of this invention, and are not to be construed as limiting the scope of the invention in any way.

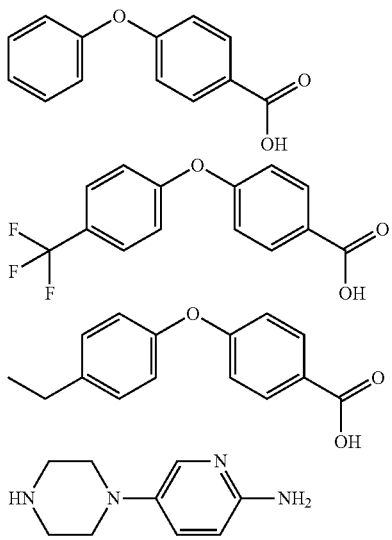

Other intermediates can be prepared according to methods described below:

The compounds of the invention may be prepared by the general methods and examples presented below and methods known to those of ordinary skill in the art. Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Intermediates used in the syntheses below are either commercially available or easily prepared by methods known to those skilled in the art. Reaction progress may be monitored by conventional methods such as thin layer chromatography (TLC) or high pressure liquid chromatography-mass spec (HPLC-MS). Intermediates and products may be purified by methods known in the art, including column chromatography, HPLC, preparative TLC or recrystallization.

The methods described below and in the Synthetic Examples section may be used to prepare the compounds of invention.

Intermediates and examples reported in the following bearing a basic or acidic group may be obtained as a corresponding salt or neutral compound depending on the purification method and conditions employed. Salts can be transformed into their neutral counterparts by standard procedures known to the one skilled in the art.

General Methods: Unless noted otherwise, all reactions are run at room temperature (about 25° C.), under inert atmosphere (e.g., Argon, $N_2$), and under anhydrous conditions. All compounds are characterized by at least one of the following methods: $^1$H NMR, HPLC, HPLC-MS, or melting point.

Typically, reaction progress is monitored by thin layer chromatography (TLC) or HPLC-MS. Intermediates and products are purified using at least one of the following methods:

Flash chromatography on silica gel, Recrystallization, Super Critical Fluid (SFC) Chiral HPLC using a 3.0× 25.0 cm RegisPack column, eluting with an isocratic mixture of MeOH, isopropylamine, and super critical carbon dioxide at 125 bar; 80 mL/min, and/or Super Critical Fluid (SCF) Chiral HPLC using a 10×250 mm or a 20×250 mm column, eluting with an isocratic mixture of MeOH with 20 mM $NH_3$, EtOH with 20 mM $NH_3$ or isopropylalcohol with 20 mM $NH_3$, and super critical carbon dioxide at 150 bar; 60 up to 80 mL/min, and/or Reversed phase HPLC using a C18 semi-preparative column eluting with a gradient of:
ACN+0.1% TFA and $H_2O$+0.1% TFA,
ACN+0.1% formic acid and $H_2O$+0.1% formic acid, or
ACN and $H_2O$ containing 2.5 mM $NH_4HCO_3$.
ACN and $H_2O$ and 0.1% TFA,
ACN and $H_2O$ and 0.1% solution of $NH_3$ in water
ACN and $H_2O$+0.1% TFA
ACN and $H_2O$+0.1% solution of $NH_3$ in water
MeOH and $H_2O$+0.1% TFA
MeOH and $H_2O$+0.1% solution $NH_3$ in water General Synthetic Procedure Preparation The compounds according to the invention and their intermediates may be obtained using methods of synthesis which are known to one skilled in the art and described in the literature of organic synthesis. Preferably the compounds are obtained analogously to the methods of preparation explained in more detail hereinafter, in particular as described in the experimental section. In some cases the sequences adopted in carrying out the reaction schemes may be varied. Variants of these reactions, that are known to a person skilled in the art, but are not described in detail here may also be used. The general processes for preparing the compounds according to the invention will become apparent to a person skilled in the art by studying the schemes that follow. Starting compounds are commercially available or may be prepared by methods that are described in the literature or herein, or may be prepared in an analogous or similar manner. Before the reaction is carried out, any functional groups in the starting compounds may be protected using conventional protecting groups. These protecting groups may be cleaved again at a suitable stage within the reaction sequence using methods familiar to the skilled person and described in the literature for example in "Protecting Groups", 3$^{rd}$ Edition, Philip J. Kocienski, Thieme, 2005 and "Protective Groups in Organic Synthesis", 4$^{th}$ Edition, Peter G. M. Wuts, Theodora W. Greene, John Wiley & Sons, 2006.

As depicted in Scheme 1 the compounds of the general formula (I) of the invention may be prepared by the reaction of a suitable carboxylic acid of formula INT-1 (either as a free acid or as a salt with a suitable metal cation such as Li$^+$, Na$^+$, K$^+$, etc.) and a suitable amine intermediate of the general formula INT-2 (either as a free amine or as a salt such as hydrochloride, hydrobromide, etc.) in a suitable solvent (e.g. N,N-dimethylformamide, N,N-dimethylacetamide, 1-methyl-2-pyrrolidinone, dichloromethane, tetrahydrofuran, 1,4-dioxane, etc.) in the presence of a suitable coupling agent (e.g. O-(7-azabenzotriazol-1-yl)-N,N,N',N'- tetramethyluronium hexafluorophosphate (HATU), O-(benzotriazol-1-yl)-N,N—N',N'-tetramethyl-uronium tetrafluoroborate (TBTU), (benzotriazol-1-yloxy)tripyrrolidinophosphonium hexafluorophosphate (PyBOP), carbodiimide reagents, etc.) and a base (e.g. trimethylamine, N,N-diisopropyl-ethylamine, pyridine, etc.) to form an amide bond. The groups/terms $R^1$ to $R^4$, $R^7$ to $R^{10}$, A, and Y in Scheme 1 have the meanings as defined hereinbefore and hereinafter.

The carboxylic acid INT-1 may alternatively be transformed into a carboxylic chloride (using e.g. thionyl chloride or oxalyl chloride in dichloromethane) and coupled as such with amine INT-2 in the presence of a suited base (e.g. trimethylamine, N,N-diisopropyl-ethylamine, pyridine, etc.) in an appropriate solvent. The groups/terms $R^1$ to $R^4$, $R^7$ to $R^{10}$, A, and Y in Scheme 1 have the meanings as defined hereinbefore and hereinafter. Alternatively the carboxylic acid INT-1 can be activated with di(imidazole-1-yl)methanone (CDI) and coupled as such with an amine INT-2 in the presence of a suited base (e.g. trimethylamine, N,N-diisopropyl-ethylamine, etc.) in an appropriate solvent (e.g. N,N-dimethylformamide, N,N-dimethylacetamide, etc.).

Intermediates INT-1 and INT-2 are known in the art or can be prepared by the methods described below or in the literature of organic chemistry.

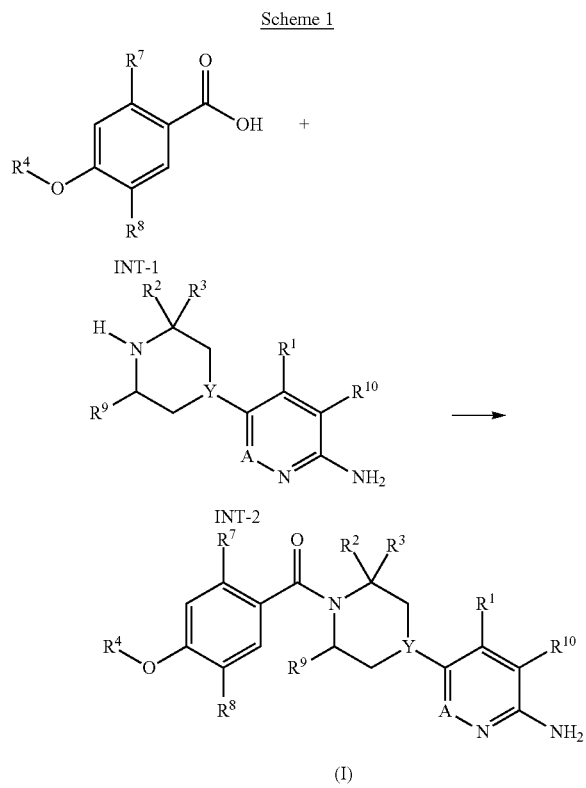

The intermediates of the general formula INT-2 shown in Scheme 1 may be prepared according to Scheme 2 in case Y=CH. The groups/terms $R^1$ to $R^3$ and $R^9$ to $R^{10}$, A and Y=CH in Scheme 2 have the meanings as defined hereinbefore and hereinafter.

Intermediate INT-5 may be prepared from boronic acid derivative INT-3 and a halogen containing heteroaromatic derivative INT-4. The reaction is performed with a palladium catalyst (e.g. 1,1'-bis(diphenylphosphino)-ferrocene]-dichloropalladium(II)-CH$_2$Cl$_2$-complex (PdCl$_2$(dppf) *CH$_2$Cl$_2$), or chloro(2-dicyclohexylphosphino-2',4',6'-triisopropyl-1,1'-biphenyl)[2-(2'-amino-1,1'-biphenyl)] palladium(II) (XPhos Pd 2$^{nd}$ generation catalyst), or tris (dibenzylideneacetone)-dipalladium Pd$_2$(dba)$_3$ with additional XPhos as ligand, etc.) in the presence of a base (e.g. potassium phosphate, sodium carbonate, etc.) in an appropriate solvent (water/tetrahydrofuran, water/1,4-dioxane, water/n-butanol, 1,4-dioxane or N,N-dimethylformamide, etc.) at elevated temperature e.g. 80° C. to 150° C. The reaction may optionally be performed in a microwave.

In case a heteroaromatic intermediate INT-4 is employed with a protected or masked amino group (NL$_2$ is not NH$_2$) this group can be transformed afterwards into the NH$_2$ group by cleaving off the protective group applying standard procedures reported in the literature of organic chemistry. A tert.-butyl carbonyl group (such as a Boc protecting group) is preferably cleaved under acidic conditions with e.g. trifluoroacetic acid or hydrochloric acid, in a solvent such as dichloromethane, 1,4-dioxane, isopropanol, HCl in 1,4-dioxane or ethyl acetate, etc. A benzyl group may be removed by using hydrogen in the presence of a transition metal such as palladium on carbon. Benzyl groups bearing electron donating groups such as methoxy on the aromatic ring may also be removed under acidic conditions (e.g. with trifluoroacetic acid or hydrochloric acid). The 2,5-dimethylpyrrol ring may be cleaved to release the amino-functionality by hydroxylamine hydrochloride and trimethylamine in an appropriate solvent like a mixture of ethanol and water at elevated temperature preferably 80 to 100° C.

The nitrogen-atom of the piperidine ring of the intermediate INT-3 may be protected with an appropriate protecting group PG1 (e.g. tert-butyl-oxycarbonyl (Boc), benzyl-oxycarbonyl (Cbz), benzyl (Bn), etc.). The protecting group PG1 can be introduced by methods known to a person skilled in the art. The removal of the protecting group PG1 from INT-6 yielding INT-2 with Y=N as shown in Scheme 2 can be performed by methods known to a person skilled in the art or as described hereinbefore and hereinafter. Preferably a tert.-butyl carbonyl group (such as a Boc protecting group) can be cleaved under acidic conditions with e.g. trifluoroacetic acid or hydrochloric acid, in a solvent such as dichloromethane, 1,4-dioxane, isopropanol, HCl in 1,4-dioxane or ethyl acetate, etc. The groups/terms $R^1$ to $R^3$, $R^9$ to $R^{10}$, A and Y=CH in Scheme 2 have the meanings as defined hereinbefore and hereinafter.

The position of the double bond in the piperidine-ring of intermediate the INT-3 may depend on the substituents $R^2$, $R^3$ and $R^9$. The groups/terms $R^2$, $R^3$, and $R^9$ have the meanings as defined hereinbefore and hereinafter. The substituent $R^2$ of the intermediates INT-3, INT-5 and INT-6 may contain functional groups which may also bear appropriate protecting groups. In particular, hydroxy groups can be protected with appropriate silyl-containing protecting groups (e.g. triethylsilyl, tert.-butyl-dimethylsilyl, etc.). Protecting groups for functional groups at $R^2$ can be selected in a way that the protecting groups can be removed without removing PG1 to allow further modifications at $R^2$. Silyl protecting groups may be cleaved e.g. with a fluoride source (e.g. tetra-n-butylammonium fluoride) in a suited solvent (e.g. tetrahydrofuran) at ambient temperature or under acidic conditions (e.g. hydrochloric acid in 1,4-dioxane, HCl in 1,4-dioxane, etc.) at elevated temperature.

Scheme 2

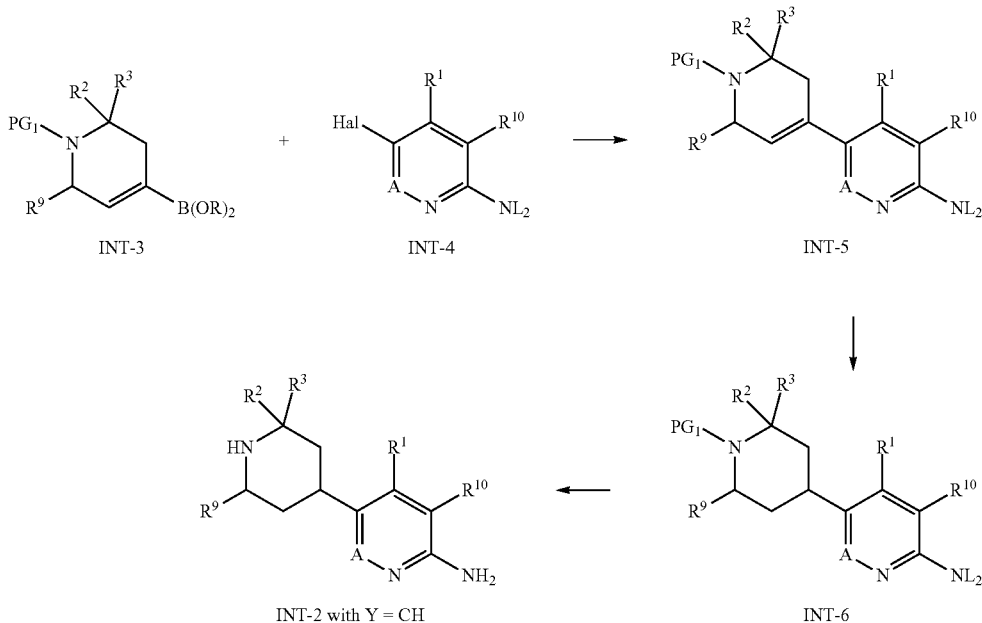

Hal=Cl, Br, I
B(OR)$_2$=B(OH)$_2$ or

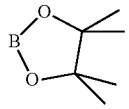

NL$_2$=NH$_2$ or protected or masked NH$_2$ such as NH-Bn or NH-DMB (DMB=2,4-dimethoxybenzyl) or

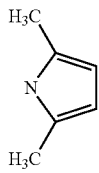

PG$_1$=Boc, Cbz or benzyl

The position of the resulting double bond in the piperidine-ring of intermediate INT-5 as shown in Scheme 2 may depend on the substituents R$^2$, R$^3$ and R$^9$. The groups/terms R$^1$ to R$^3$, R$^9$ to R$^{10}$ and A have the meanings as defined hereinbefore and hereinafter. The double bond in the piperidine-ring of intermediate INT-5 may be hydrogenated by using hydrogen in the presence of a transition metal, preferably palladium (or Pd(OH)$_2$, etc.) on carbon in a solvent such as methanol, ethanol, tetrahydrofuran, 1,4-dioxane, methanol/acetic acid, etc. to yield INT-6. Preferably, hydrogen is applied at 1 to 5 bar pressure and the reaction may be performed at room temperature up to 50° C.

Depending on the reaction conditions and the overall deprotection strategy (removal of the protecting group PG1 from INT-6 and conversion of NL$_2$ to NH$_2$) the intermediate INT-2 with Y=CH may be obtained either as a free base or as a salt such as hydrochloride, trifluoroacetate, hydrobromide, etc. The salt of the intermediate INT-2 may be transformed into their neutral counterparts by standard procedures known to the one skilled in the art.

The compounds of the general formula INT-2 shown in Scheme 1 can be prepared according to Scheme 3, if Y=N. The groups/terms R$^1$ to R$^3$, R$^9$ to R$^{10}$, A and Y=N in Scheme 3 have the meanings as defined hereinbefore and hereinafter. The substituent R$^2$ of the intermediates INT-2 and INT-8 in Scheme 3 may contain functional groups which may also bear appropriate protecting groups. In particular, hydroxy groups may be protected with appropriate silyl-containing protecting groups (e.g. triethylsilyl, tert.-butyl-dimethylsilyl, etc.). Protecting groups for functional groups at R$^2$ can be selected in a way that the protecting groups can be removed without removing PG1 to allow further modifications at R$^2$. Silyl protecting groups may be cleaved e.g. with a fluoride source (e.g. tetra-n-butylammonium fluoride) in a suited solvent (e.g. tetrahydrofuran) at ambient temperature or under acidic conditions (e.g. hydrochloric acid in 1,4-dioxane, HCl in 1,4-dioxane) at elevated temperature.

INT-4 in Scheme 3 may be coupled directly with the N-containing heterocycle INT-7 to form the carbon-nitrogen bond to provide intermediate INT-8. The groups/terms R$^1$ to R$^3$, R$^9$ to R$^{10}$, A and Y=N in Scheme 3 have the meanings as defined hereinbefore and hereinafter. The reaction is preferably conducted with a palladium derived catalyst (e.g. 2-(2'-di-tert-butylphosphine)-biphenyl palladium (II) acetate, or (2-dicyclohexyl-phosphino-2',6'-diisopropoxy-1,1'-biphenyl)[2-(2'-amino-1,1'-biphenyl)]-palladium(II) methanesulfonate (RuPhos Pd 3$^{rd}$ generation), or CPhos-3G-palladacycle methane sulfonate, etc.) in the presence of a base (e.g. sodium tert-butoxide, cesium carbonate, etc.) in a suited solvent (e.g. toluene, tetrahydrofuran, 1,4-dioxane, etc.) at 40 to 120° C.

In case the heteroaromatic intermediate INT-4 is employed with a protected or masked amino group (NL$_2$ is not NH$_2$) this group can be transformed afterwards into the NH$_2$ group by cleaving off the protective group applying standard procedures reported in the literature of organic chemistry or as described hereinbefore and hereinafter. This transformation into the NH$_2$-group may be performed at different stages (e.g. to provide intermediate INT-9 or intermediate INT-2 with Y=N) within the overall synthesis of intermediate INT2 with Y=N as shown in Scheme 3 depending on the overall synthesis strategy and overall protecting group strategy.

Removal of the protecting group PG1 of INT-8 or INT-9 may be performed as reported in the literature of organic chemistry or hereinbefore and hereinafter. A tert.-butyl carbonyl group (Boc) may be preferably cleaved under acidic conditions with e.g. trifluoroacetic acid or hydrochloric acid, in a solvent such as dichloromethane, 1,4-dioxane, isopropanol, or ethyl acetate. A benzyl (Bn) group or a benzyloxycarbonyl (Cbz) group may be removed by using hydrogen in the presence of a transition metal such as palladium on carbon. Benzyl groups bearing electron donating groups such as methoxy groups on the aromatic ring may also be removed under acidic conditions (e.g. with trifluoroacetic acid or hydrochloric acid).

Depending on the reaction conditions and the overall deprotection strategy the intermediate INT-2 with Y=N may be obtained either as a free base or as a salt such as hydrochloride, trifluoroacetate, hydrobromide, etc.). Salts may be transformed into their neutral counterparts by standard procedures known to the one skilled in the art. Removal of the protecting group PG1 may be performed at various steps during the overall synthesis of intermediate INT-2 with Y=N (e.g. removal of protecting group PG1 from intermediate INT-9 leading to INT-2 with Y=N or from intermediate INT-8 leading to INT-10 as shown in Scheme 3) depending on the overall synthesis strategy and deprotection strategy. The groups/terms R$^1$ to R$^3$, R$^9$ to R$^{10}$, A and Y=N in Scheme 3 have the meanings as defined hereinbefore and hereinafter.

Scheme 3

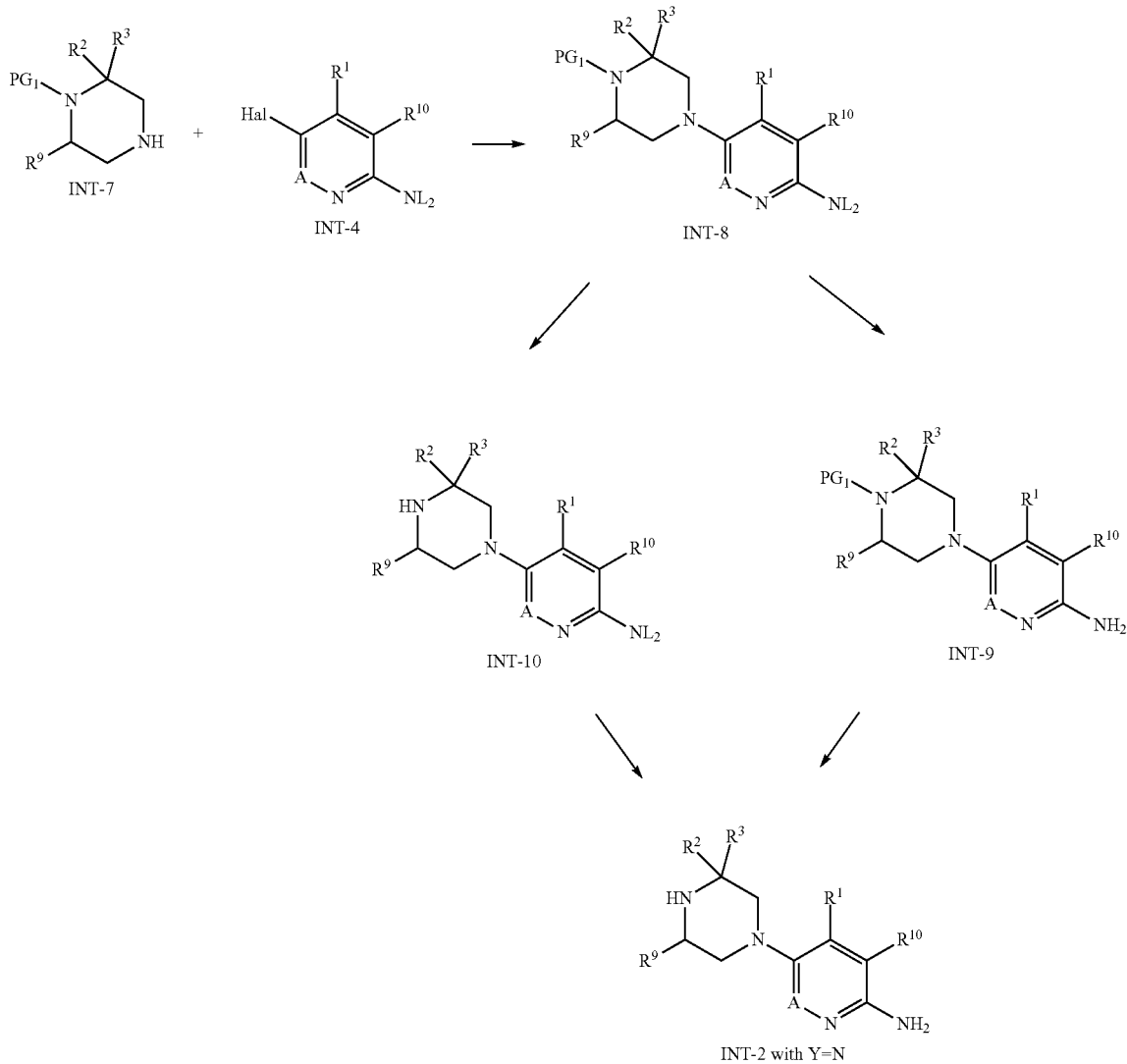

Hal=Cl, Br, I
NL$_2$=NH$_2$ or protected or masked NH$_2$ such as NH-Bn or NH-DMB (DMB=2,4-dimethoxybenzyl) or

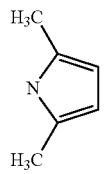

PG$_1$=Boc, Cbz or benzyl

The intermediates of the general formula INT-2 may alternatively be prepared according to Scheme 4. The groups/terms R$^1$ to R$^4$, R$^7$ to R$^{10}$, and A in Scheme 4 have the meanings as defined hereinbefore and hereinafter and Y=N.

In intermediate INT-12, NO$_n$ represents either a nitro-group (n=2) or a nitroso-group (n=1). Intermediates of the general formula INT-12 may be prepared via a nucleophilic substitution on an electron-poor heteroaromatic derivative bearing either a nitro or nitroso group of the general formula INT-11 and a suitable piperazine derivative of formula INT-7, which may be protected with a protecting group PG1, in a suitable solvent (e.g. ethanol) and in the presence of a suitable base (e.g. diisopropyl-ethyl-amine, etc.).

Alternatively, intermediate INT-12 with Y=N in Scheme 4 may be prepared by a transition metal catalyzed coupling reaction of a suitable piperazine derivative of formula INT-7 and a heteroaromatic derivative bearing a nitro group (n=2) of the general formula INT-11 in the presence of a catalyst preferably a palladium catalyst (e.g. tris(dibenzylideneacetone)-dipalladium Pd$_2$(dba)$_3$, etc.) and a suitable ligand preferably XantPhos (4,5-bis(diphenylphosphino)-9,9-dimethylxanthene) in a suitable solvent (e.g. 1,4-dioxane, etc.) and in the presence of a suitable base (e.g. cesium carbonate, etc.) at elevated temperature e.g. 80-120° C.

Intermediate INT-9 may also be synthesized according to Scheme 4. The groups/terms R$^1$ to R$^4$, R$^7$ to R$^{10}$, A, and Y=N in Scheme 4 have the meanings as defined hereinbefore and hereinafter and Y=N. The nitroso (n=1) or nitro (n=2) groups of INT-12 may be transformed into an amino group by methods known to a person skilled in the art. Preferably the reduction of the nitroso or nitro-group of INT-12 may be performed in a hydrogen atmosphere (e.g. at 1 to 5 bar) and in the presence of a transition metal, preferably palladium on carbon in a solvent such as methanol, ethanol, tetrahydrofuran, 1,4-dioxane, etc. In analogous manner compounds of the general formula (I) may be synthesized from INT-14 according to Scheme 4 via reduction of the nitroso or nitro group. The removal of the protecting group PG1 from intermediate INT-9 leading to intermediate INT-2 with Y=N may be performed using the same reaction conditions as described in Scheme 3. The reaction from intermediate INT-2 with Y=N to compound of the general formula (I) may be performed using the same reaction conditions as described in Scheme 1.

Intermediates of the formula INT-14 may be prepared from compound INT-13 and a carboxylic acid INT-1 in a similar manner as described for compounds of the general formula (I) in Scheme 1. Compounds of the general formula (I) may also be synthesized as shown in Scheme 4 from INT-14 via conversion of the nitroso (n=1) or nitro (n=2) group to the amino group in analogy to procedures reported in the literature of organic chemistry preferably in a hydrogen atmosphere in the presence of palladium on carbon in a suitable solvent (e.g. methanol, ethanol, etc.). The groups/terms R$^1$ to R$^4$, R$^7$ to R$^{10}$ and A, in Scheme 4 have the meanings as defined hereinbefore and hereinafter and Y=N.

Scheme 4

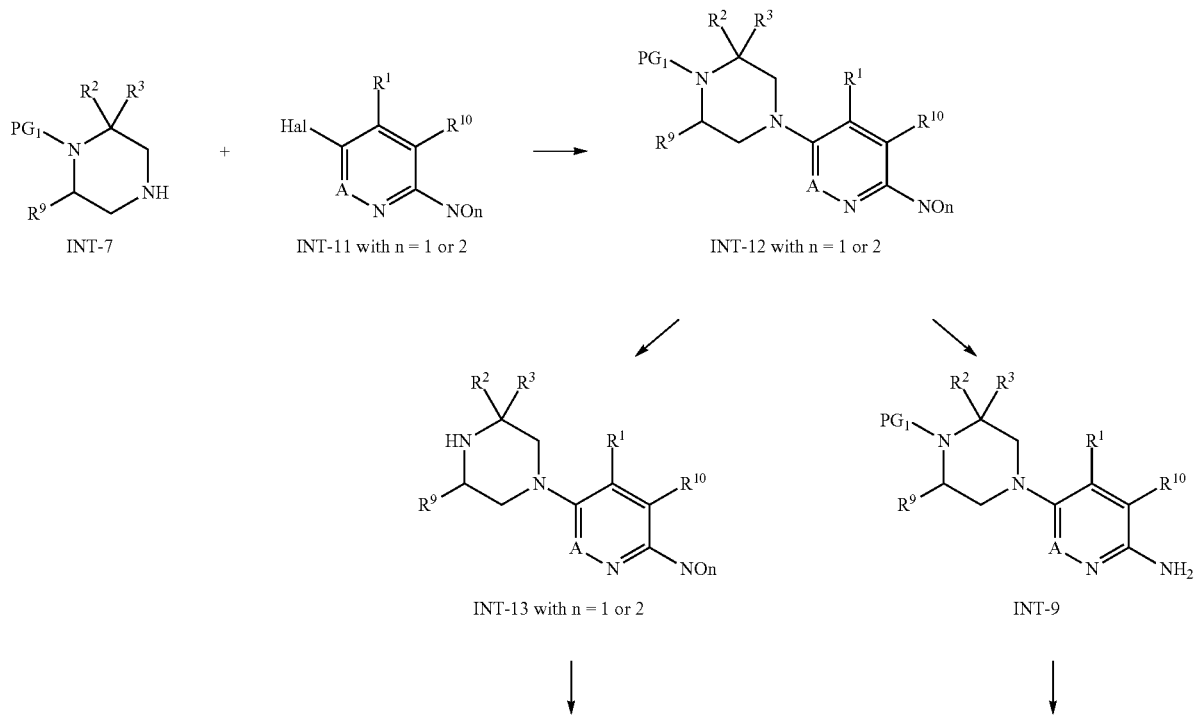

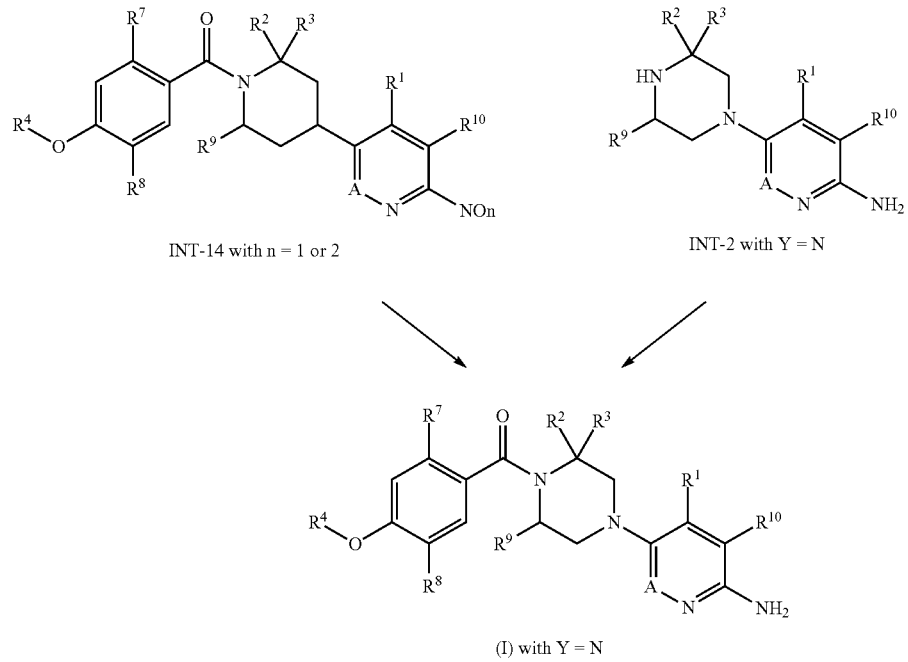

Hal = F, Cl, Br
PG₁ = Boc, Cbz or Benzyl
NOn = NO or NO₂

As shown in Scheme 5 the group $R^4$=aryl may be attached to the phenyl moiety of INT-16 via an oxygen starting from various precursors. $R^7$ to $R^8$ and $R^4$=aryl have the meanings as defined hereinbefore and hereinafter. The two parts ($R^4$ of INT-15 and the phenyl moiety of INT-16) may be linked using one of them decorated with a hydroxyl group (V or W denoted OH) and the other one with a boronic acid derivative (e.g. W or V denoted B(OH)₂, B(OCMe₂CMe₂O), etc.).

The two building blocks INT-15 and INT-16 accordingly equipped may be coupled employing copper(acetate) in the presence of a base (e.g. pyridine or trimethylamine), molecular sieves, optionally a co-oxidant (e.g. oxygen), in a solvent, e.g. dichloromethane, at 0 to 60° C.

Alternatively, the linkage between $R^4$ of INT-15 and the phenyl moiety of INT-16 via oxygen is formed upon coupling the aryl moiety $R^4$ bearing an OH group (V=OH) and the phenyl moiety of INT-16, bearing a leaving group (W=e.g. F, Cl). The oxygen of the OH group of INT-15 replaces the leaving group by nucleophilic substitution or a transition metal catalyzed reaction. This proceeding is particularly suited for electron deficient phenyl moieties of INT-16 which are coupled with the hydroxylated $R^4$-moiety in the presence of a base (e.g. Cs₂CO₃, K₂CO₃, KOH, trimethylamine or NaH) preferably in a solvent (e.g. toluene, tetrahydrofuran, 1,2-dimethoxyethane, 1,4-dioxane, N,N-dimethylformamide, N,N-dimethylacetamide, N-methylpyrrolidinone, alcohol, water or mixtures thereof), at 0 to 220° C.

As shown in Scheme 5 carboxylic acids of formula INT-1, wherein the groups/terms $R^4$, and $R^7$ to $R^8$ have the meanings as defined hereinbefore and hereinafter, are preferably prepared from the corresponding ester of the general formula INT-17 by hydrolysis or hydrogenolysis depending on the nature of the protecting group PG2. The ester group of INT-17 may be hydrolyzed in the presence of an acid such as hydrochloric acid or sulfuric acid, or an alkali metal hydroxide such as lithium hydroxide, sodium hydroxide or potassium hydroxide to yield the carboxylic acid. The hydrolysis is preferably conducted in aqueous solvents, such as water combined with tetrahydrofuran, 1,4-dioxane, alcohol (e.g. methanol, ethanol and isopropanol), or dimethyl sulfoxide at 0 to 120° C. If the protecting group PG2 of INT-17 represents lower alkyl group esters such as ethyl or methyl esters, those are preferably cleaved by hydrolysis with a hydroxide base such as NaOH, LiOH or KOH in a mixture of water and a suitable miscible solvent (e.g. tetrahydrofuran, methanol, ethanol, 1,4-dioxane, etc. or mixtures of these), with heating if necessary. The tert.-butyl ester is preferably cleaved by treatment under acidic conditions (e.g. hydrochloric acid or trifluoroacetic acid) in a suitable solvent (e.g. dichloromethane, 1,4-dioxane, methanol, ethanol, tetrahydrofuran, water or mixtures of these). A benzyl ester is preferably cleaved using hydrogen in the presence of a transition metal (preferably e.g. palladium on carbon, etc.) in a suitable solvent (e.g. ethanol, methanol, tetrahydrofuran, dichloromethane, ethyl acetate) under an atmosphere of hydrogen (preferably 1 to 5 bar). Benzyl esters bearing electron donating groups on the phenyl ring, such as methoxy, may also be removed under oxidative conditions, e.g. ceric ammonium nitrate (CAN) or 2,3-dichloro-5,6-dicyanoquinone (DDQ) are reagents commonly used for this approach. The acid INT-1 in Scheme 5 may be isolated either as a salt with the metal cation or as a free acid depending on the reaction conditions.

Scheme 5

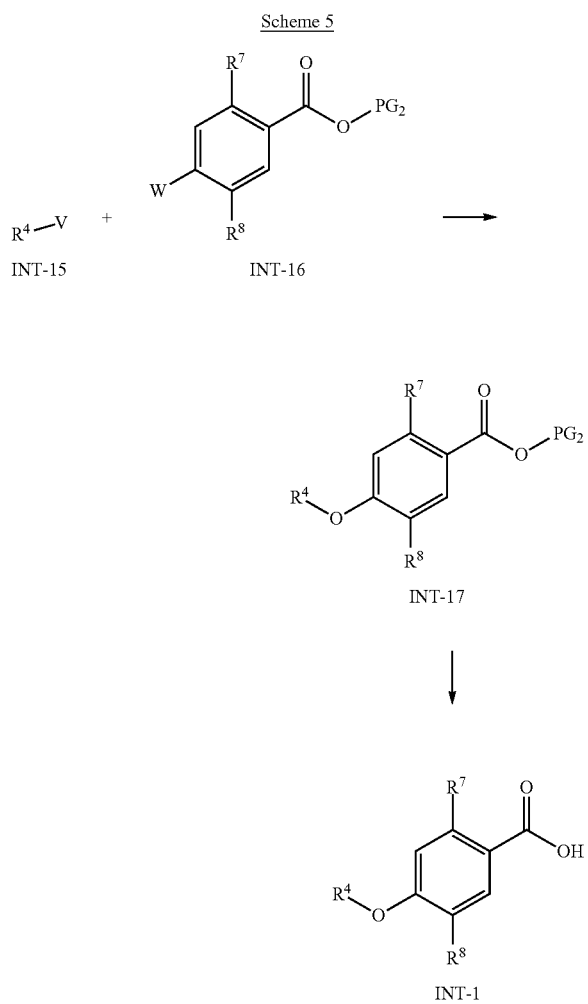

V = e.g., OH, B(OH)$_2$, B(OCMe$_2$CMe$_2$O), Cl, Br, I
W = e.g., OH, B(OH)$_2$, B(OCMe$_2$CMe$_2$O), F, Cl, Br, I
R4 = Aryl
PG$_2$ = Methyl, ethyl, tert.-butyl, benzyl As depicted in Scheme 6 compounds of the general formula INT-17 may be assembled by using building blocks INT-21 and INT-18 if R$^4$ does not denote aryl. R$^4$, and R$^7$ to R$^8$ have the meanings as defined hereinbefore and hereinafter and R$^4$ does not denote aryl. Building blocks of the general formula INT-21 and INT-18 may be combined in a stereoselective fashion employing the conditions of the Mitsunobu reaction or variants thereof (Scheme 6). The reaction is usually conducted with a phosphine and an azodicarboxylic ester or amide in tetrahydrofuran, 1,4-dioxane, diethyl ether, toluene, benzene, dichloromethane or mixtures thereof, at −30 to 100° C. Phosphines which are often used are triphenylphosphine and tributylphosphine. These are commonly combined with dimethyl azodicarboxylate, diethyl azodicarboxylate, diisopropyl azodicarboxylate, di-(4-chlorobenzyl) azodicarboxylate, dibenzyl azodicarboxylate, di-tert-butyl azodicarboxylate, azodicarboxylic acid bis-(dimethylamide), azodicarboxylic acid dipiperidine, or azodicarboxylic acid dimorpholide.

Scheme 6

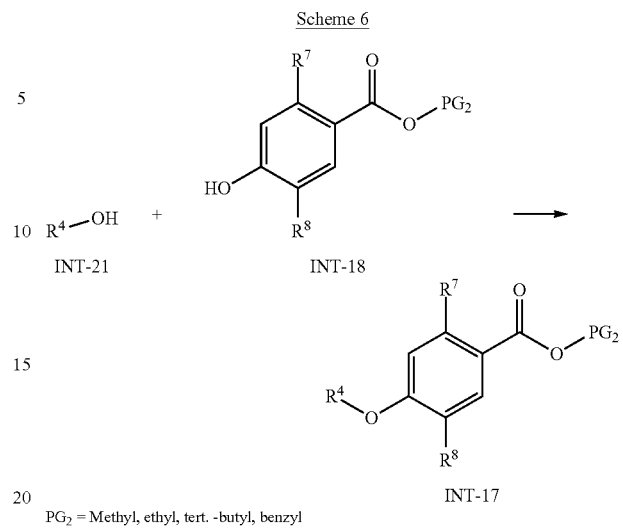

PG$_2$ = Methyl, ethyl, tert.-butyl, benzyl

As depicted in Scheme 7, compounds of the general formula INT-20 may be prepared by the reaction of a suitable carboxylic acid of the general formula INT-19 (either as a free acid or as a salt with a suitable metal cation such as Lit, Nat, etc.) and a suitable amine INT-2 (either as free amine or as salt such as hydrochloride, hydrobromide, etc.) via amide bond formation in an analogous manner as described for the synthesis of compounds of the general formula (I) in Scheme 1. The groups/terms R$^1$ to R$^3$, R$^7$ to R$^{10}$, A, and Y in Scheme 7 have the meanings as defined hereinbefore and hereinafter.

Scheme 7

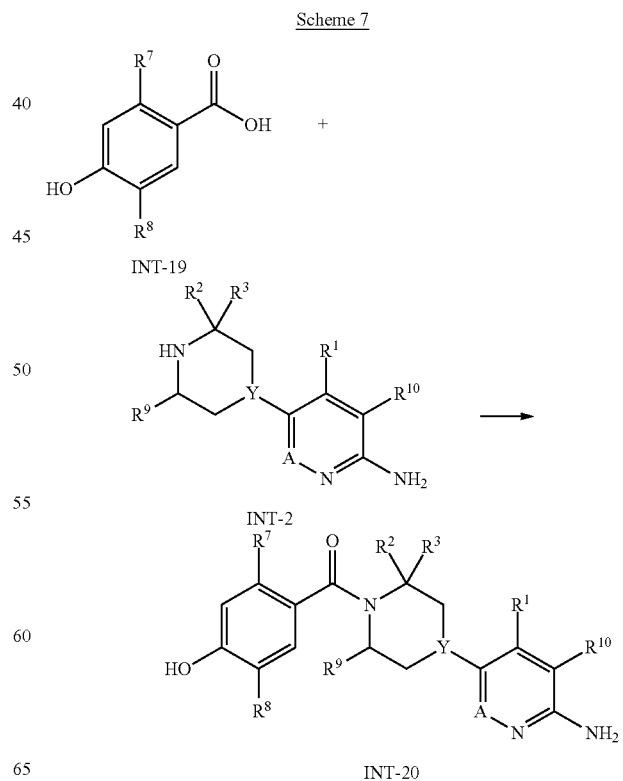

As depicted in scheme 8 compounds of the general formula (I) may be synthesized by combining building blocks INT-21 and INT-20 employing the conditions of the Mitsunobu reaction or variants thereof if $R^4$ denotes not aryl. The groups/terms $R^1$ to $R^4$, $R^7$ to $R^{10}$, A, and Y in Scheme 8 have the meanings as defined hereinbefore and hereinafter, and $R^4$ denotes not aryl. The general procedure for the Mitsunobu reaction is described for the synthesis of INT-17 in Scheme 6.

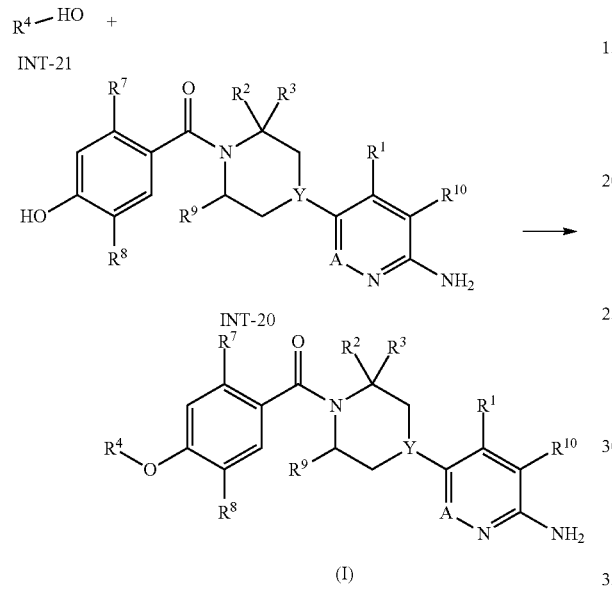

The synthetic routes presented may rely on the use of protecting groups. For example, potentially reactive groups present, such as hydroxyl, carbonyl, carboxyl, amino, alkylamino, or imino, may be protected during the reaction by conventional protecting groups which are cleaved again after the reaction. Suitable protecting groups for the respective functionalities and their removal are well known to the one skilled in the art and are described in the literature of organic synthesis.

The compounds of the general formula I may be resolved into their enantiomers and/or diastereomers as mentioned below. Thus, for example, cis/trans mixtures may be resolved into their cis and trans isomers and racemic compounds may be separated into their enantiomers.

The cis/trans mixtures may be resolved, for example, by chromatography into the cis and trans isomers thereof. The compounds of general formula I which occur as racemates may be separated by methods known per se into their optical antipodes and diastereomeric mixtures of compounds of general formula I may be resolved into their diastereomers by taking advantage of their different physico-chemical properties using methods known per se, e.g. chromatography and/or fractional crystallization; if the compounds obtained thereafter are racemates, they may be resolved into the enantiomers as mentioned below.

The racemates are preferably resolved by column chromatography on chiral phases or by crystallization from an optical active solvent or by reacting with an optically active substance which forms salts or derivatives such as esters or amides with the racemic compound. Salts may be formed with enantiomerically pure acids for basic compounds and with enantiomerically pure bases for acidic compounds.

Diastereomeric derivatives are formed with enantiomerically pure auxiliary compounds, e.g. acids, and their activated derivatives, or alcohols. Separation of the diastereomeric mixture of salts or derivatives thus obtained may be achieved by taking advantage of their different physico-chemical properties, e.g. differences in solubility; the free antipodes may be released from the pure diastereomeric salts or derivatives by the action of suitable agents. Optically active acids commonly used for such a purpose, as well as optically active alcohols applicable as auxiliary residues, are known to those skilled in the art.

SYNTHESIS OF INTERMEDIATES

Preparation of 4-(4-cyclopropyl-phenoxy)-benzoic Acid (A)

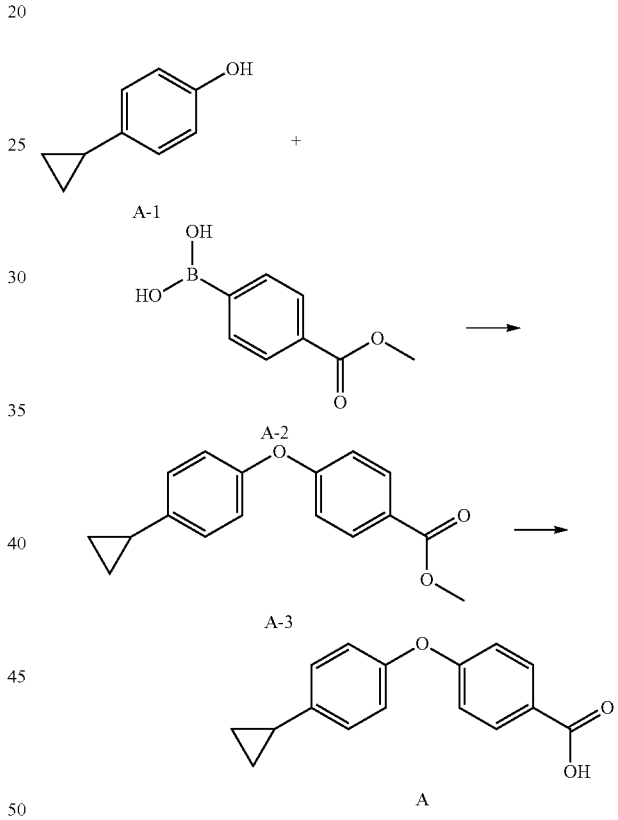

To a stirred suspension of A-1 (700 mg, 5.22 mmol) in DCM (25 mL) is added A-2 (1.88 g, 10.4 mmol), pyridine (843 µL, 10.43 mmol) and TEA (1.43 mL, 10.43 mmol). The resultant mixture is sparged with oxygen for 10 min. Copper (II) acetate (1.90 g, 10.43 mmol) is added and the reaction mixture is stirred at the ambient temperature under an oxygen atmosphere. After 3 days, the mixture is filtered and the filtrate is washed with water (10 mL), dried over $Na_2SO_4$, filtered and concentrated. The crude mixture is purified on $SiO_2$ eluting with 10% EtOAc in hexane to afford A-3.

To a stirred solution of A-3 (700 mg, 2.60 mmol) in a mixture of THF (6.5 mL) and water (5.0 mL) at 0° C. is added $LiOH \cdot H_2O$ (218 mg, 5.22 mmol). The mixture is warmed to the ambient temperature and stirred for 12 h. The reaction mixture is extracted with $Et_2O$ (10 mL). Phases are separated and the organic layer is extracted with water (2×1 mL). The combined aqueous layers are cooled to 0° C. and acidified to pH 4.0 with HCl (4 N). The resultant mixture is filtered and the solid is washed with water (3×1 mL) and Et₂O (3×3 mL), and dried under high vacuum afford the title product (A).

Preparation of 4-(3-fluoro-4-trifluoromethyl-phenoxy)-benzoic Acid (B)

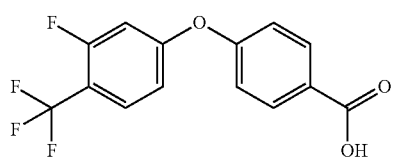

The title compound (B) is synthesized from 3-fluoro-4-trifluoromethyl-phenol (600 mg, 3.33 mmol) and A-2 (899 mg, 5.00 mmol) according to the procedure described for the synthesis of the intermediate (A).

Preparation of 4-(4-chloro-phenoxy)-benzoic Acid (C)

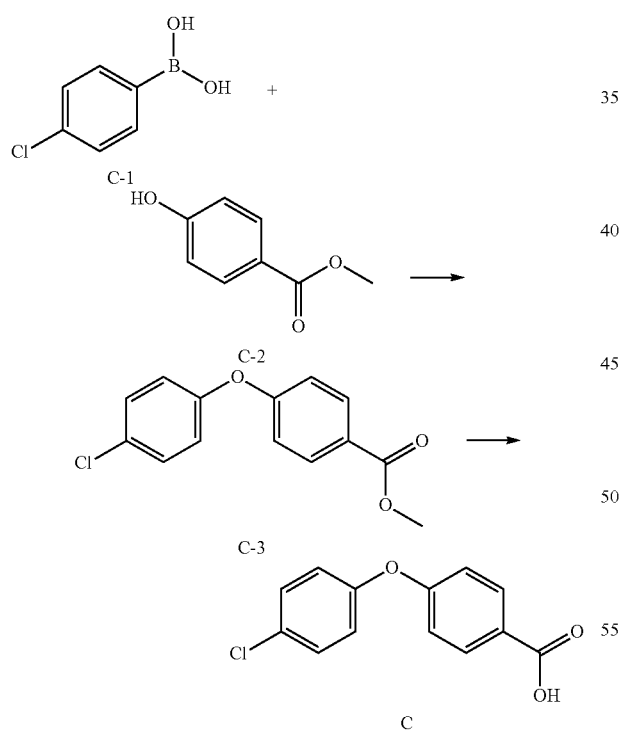

To a stirred suspension of C-2 (500 mg, 3.28 mmol) in DCM (20 mL) is added C-1 (2.06 g, 13.1 mmol), pyridine (530 µL, 6.57 mmol) and TEA (900 µL, 6.57 mmol). The resultant mixture is sparged with oxygen for 5 min. copper (II) acetate (1.20 g, 6.57 mmol) is added, and the reaction mixture is stirred at the ambient temperature. After 3 days, the mixture is diluted with water (20 mL) and extracted with EtOAc (50 mL). Phases are separated and the organic layer is washed with water (10 mL) and brine (10 mL), dried over Na₂SO₄, filtered and concentrated. The crude mixture is purified on SiO₂ eluting with 1% EtOAc in hexane to afford C-3.

To a stirred solution of C-3 (150 mg, 0.571 mmol) in a mixture of THF and water (1:1, 5 mL) at 0° C. is added LiOH.H₂O (109 mg, 2.60 mmol). The reaction mixture is stirred at the ambient temperature for 5 h and extracted with Et₂O (10 mL). Phases are separated and the organic layer is extracted with water (2×1 mL). The combined aqueous layers are acidified at 0° C. to pH 4.0 with HCl (1 N), and the resultant mixture is extracted with EtOAc (3×10 mL). The combined EtOAc layers are washed with brine (10 mL), dried over Na₂SO₄, filtered and concentrated to give the title product (C).

Preparation of 4-(4-ethyl-phenoxy)-benzoic Acid (D)

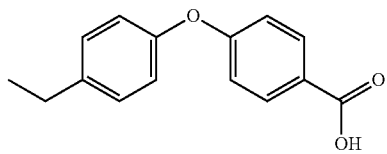

The title compound (D) is synthesized from 4-ethylphenylboronic acid (1.23 g, 8.22 mmol) and C-2 (500 mg, 3.28 mmol) according to the procedure described for the synthesis of the intermediate (C).

Preparation of 4-(4-cyano-phenoxy)-benzoic Acid (E)

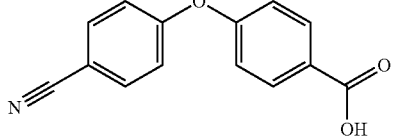

The title compound (E) is synthesized from 4-cyanophenylboronic acid (2.90 g, 19.7 mmol) and C-2 (1.00 g, 6.57 mmol) according to the procedure described for the synthesis of the intermediate (C).

Preparation of 4-(benzo[1,3]dioxol-5-yloxy)-benzoic Acid (F)

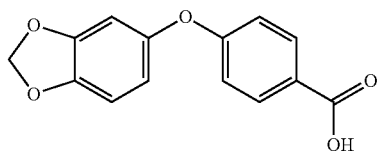

The title compound (F) is synthesized from (3,4-methylenedioxyphenyl)boronic acid (1.90 g, 11.5 mmol) and C-2 (700 mg, 4.60 mmol) according to the procedure described for the synthesis of the intermediate (C).

Preparation of 4-(4-dimethylcarbamoyl-phenoxy)-benzoic Acid (G)

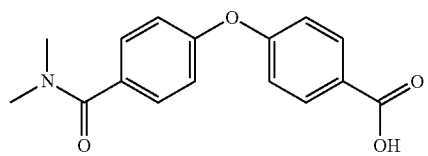

G

The title compound (G) is synthesized from 4-(N,N-dimethylaminocarbonyl)phenylboronic acid (3.80 g, 19.7 mmol) and C-2 (1.00 g, 6.57 mmol) according to the procedure described for the synthesis of the intermediate (C).

Preparation of 4-(4-acetyl-phenoxy)-benzoic Acid (H)

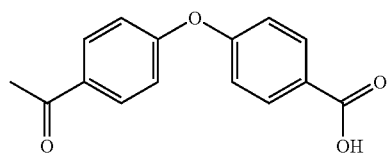

H

The title compound (H) is synthesized from 4-acetylphenylboronic acid (2.10 g, 12.8 mmol) and C-2 (1.30 g, 8.54 mmol) according to the procedure described for the synthesis of the intermediate (C).

Preparation of 4-(3,4-dichloro-phenoxy)-benzoic Acid (I)

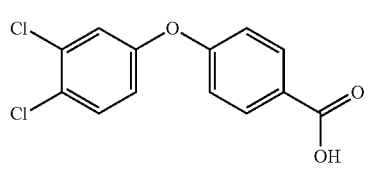

I

The title compound (I) is synthesized from 3,4-dichlorophenylboronic acid (3.76 g, 19.7 mmol) and C-2 (1.00 g, 6.57 mmol) according to the procedure described for the synthesis of the intermediate (C).

Preparation of 4-(4-methoxy-phenoxy)-benzoic Acid (J)

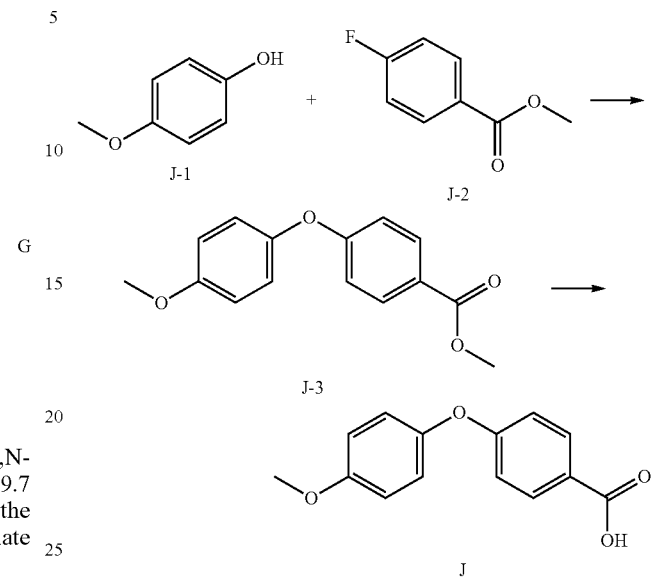

J

To a stirred solution of J-2 (1.50 g, 9.60 mmol) in DMSO (10 mL) are added J-1 (1.78 g, 14.4 mmol) and Cs$_2$CO$_3$ (9.18 g, 24.0 mmol). The resultant mixture is heated at 120° C. for 15 h. The mixture is filtered through a pad of diatomaceous earth, the filter pad is washed with EtOAc (3×30 mL) and the filtrate is extracted with water (30 mL). Phases are separated and the organic layer is dried over Na$_2$SO$_4$, filtered, and concentrated. The crude is purified on SiO$_2$ eluting with 10% EtOAc in hexane to afford J-3.

The title compound (J) is synthesized from J-3 (350 mg, 1.36 mmol) according to the procedure described for the synthesis of the intermediate (A) from A-3.

Preparation of 4-(4-fluoro-phenoxy)-benzoic Acid (K)

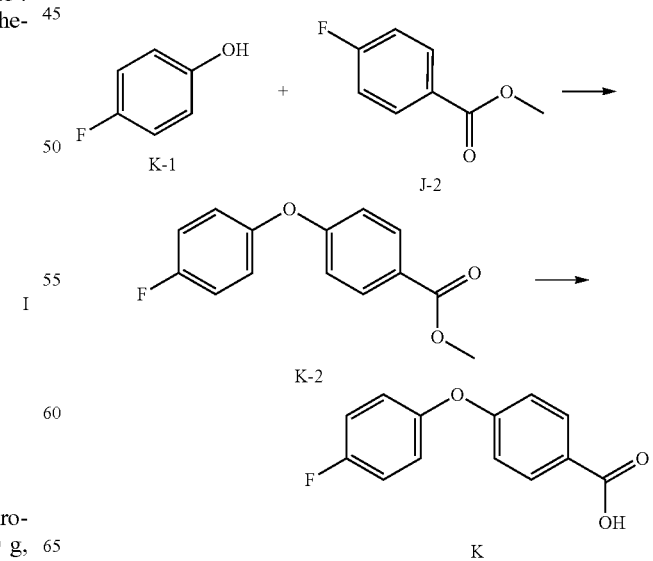

K

Intermediate K-2 is synthesized from K-1 (1.50 g, 13.4 mmol) and J-2 (3.09 g, 20.0 mmol) using K$_2$CO$_3$ (3.70 g, 26.8 mmol) in DMF (13 mL) at 80° C. according to the procedure described for the synthesis of the intermediate J-3 from J-1 and J-2.

The title compound (K) is synthesized from K-2 (1.00 g, 4.06 mmol) according to the procedure described for the synthesis of the intermediate (A) from A-3.

Preparation of 4-p-tolyloxy-benzoic Acid (L)

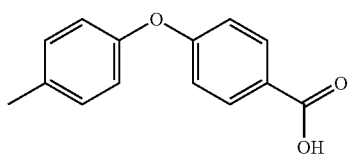

L

The title compound (L) is synthesized from 4-methylphenol (2.08 g, 19.2 mmol) and J-2 (1.50 g, 9.60 mmol) according to the procedure described for the synthesis of the intermediate (K).

Preparation of 4-(4-trifluoromethoxy-phenoxy)-benzoic Acid (M)

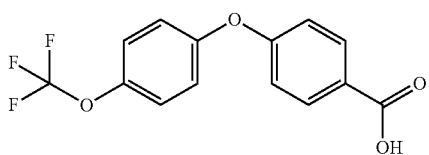

M

The title compound (M) is synthesized from 4-trifluoromethoxy-phenol (2.56 g, 14.4 mmol) and J-2 (1.50 g, 9.60 mmol) according to the procedure described for the synthesis of the intermediate (K).

Preparation of 4-(4-isopropyl-phenoxy)-benzoic Acid (N)

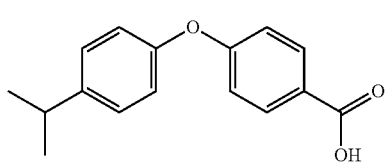

N

The title compound (N) is synthesized from 4-isopropyl-phenol (1.96 g, 14.4 mmol) and J-2 (1.50 g, 9.60 mmol) according to the procedure described for the synthesis of the intermediate (K).

Preparation of 6-piperidin-4-yl-pyridazin-3-ylamine dihydrochloride (O)

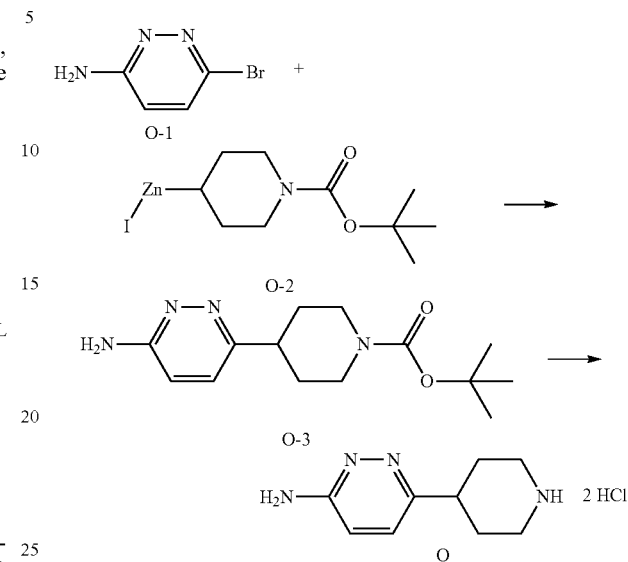

A solution of O-2 in THF (20.00 ml, 0.5 M, 10.00 mmol) is added portion-wise to a solution of O-1 (500 mg, 2.87 mmol), tris(dibenzylideneacetone)dipalladium (0) (263 mg, 0.290 mmol) and di-t-butylneopentylphosphonium tetrafluoroborate (174 mg, 0.570 mmol) in THF (25 mL), and the resultant mixture is stirred at the ambient temperature for 24 h. The reaction mixture is concentrated and re-dissolved in MeOH (10 mL) and filtered through a pad of diatomaceous earth. The filter pad is washed with MeOH (3×5 mL) and the filtrate is concentrated. The residue is purified using reverse phase HPLC chromatography (C-18 column eluting with 5% to 60% acetonitrile in water containing 0.1% formic acid). The product is further purified on SiO$_2$ eluting with a gradient of 1-10% MeOH in DCM to afford O-3.

To a solution of O-3 (486 mg, 1.74 mmol) in 1,2 dichloroethane (15 mL) is added a solution of HCl in dioxane (5.00 mL, 4M, 20.0 mmol). The resultant solution is stirred for 16 h and concentrated. The residue is triturated with DCM and dried under vacuum to afford the title product (O).

Preparation of 6-piperazin-1-yl-pyridazin-3-ylamine dihydrochloride (P)

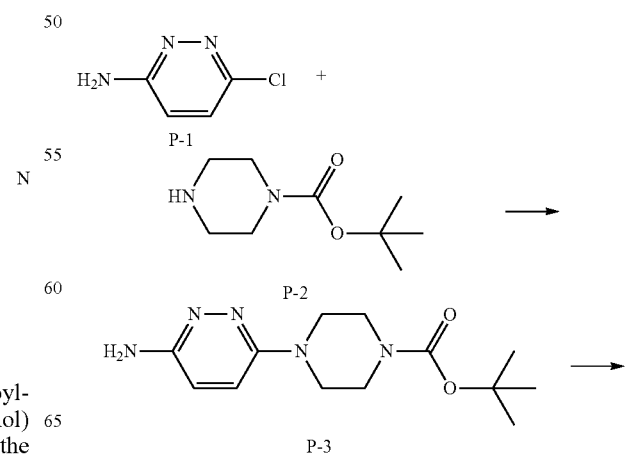

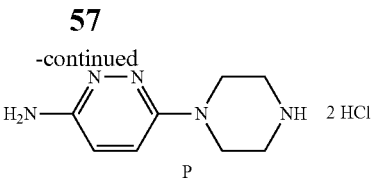

A stirred mixture of P-1 (10.0 g, 77.2 mmol) and P-2 (43.1 g, 232 mmol) in a sealed pressure vessel is heated at 150° C. for 15 h. The reaction mixture is cooled to the ambient temperature, diluted with water (50 mL) and extracted with EtOAc (100 mL). The organic layer is washed with water (3×20 mL), dried over $Na_2SO_4$, filtered and concentrated. The residue is triturated with diethyl ether to give P-3.

The title compound (P) is synthesized from P-3 (2.73 g, 6.86 mmol) according to the procedure described for the synthesis of the intermediate (O) from O-3.

Preparation of 1',2',3',4',5',6'-hexahydro-[3,4']bipyridinyl-6-ylamine dihydrochloride (Q)

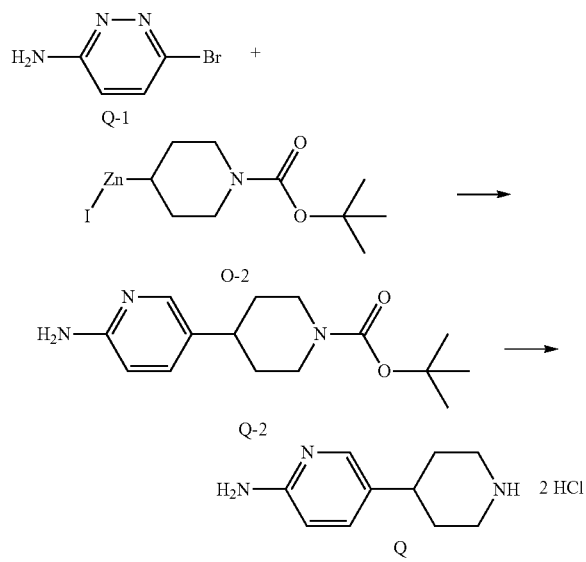

The title compound (Q) is synthesized from Q-1 (346 mg, 2.00 mmol) and O-2 (12.0 mL, 0.5 M in THF, 6.00 mmol) according to the procedure described for the synthesis of the intermediate (O).

Synthesis of Compounds of Formula I

Preparation of 5-[1-(4-phenoxybenzoyl)piperidin-4-yl]pyridin-2-amine (Compound 1)

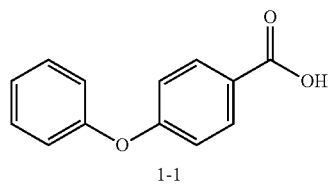

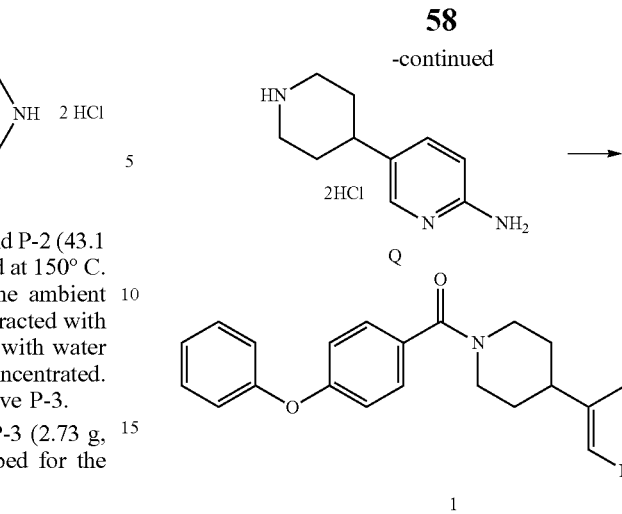

A mixture of 1-1 (40.0 mg, 0.187 mmol) and EDCI (53.6 mg, 0.280 mmol) in DMA (1 mL) is stirred for 15 min and added to a mixture of Q (60.7 mg, 0.242 mmol) and DIPEA (0.130 mL, 0.746 mmol) in DMA (0.5 mL). The resultant mixture is shaken at the ambient temperature for 16 h and stirred at 40° C. for 6 h. The crude reaction mixture is filtered and purified using a reverse phase HPLC (C-18 column, eluting with 5% to 95% acetonitrile in water containing 2.5 mM $NH_4HCO_3$) to give the title product (1).

Preparation of 6-(1-{4-[4-(trifluoromethyl)phenoxy]benzoyl}piperidin-4-yl)pyridazin-3-amine (Compound 2)

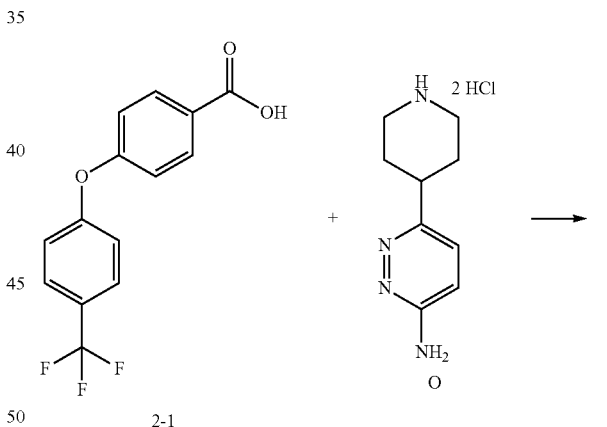

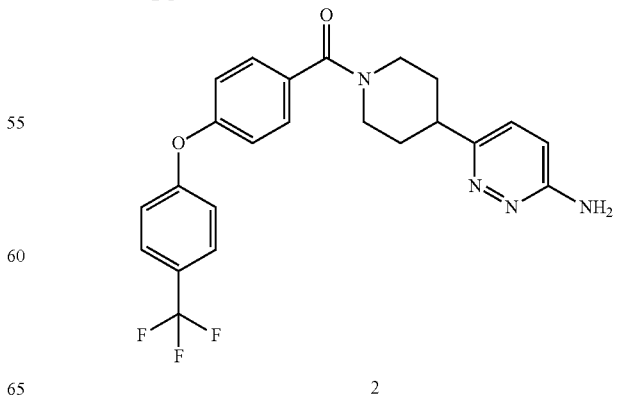

A solution of 2-1 (40.0 mg, 0.142 mmol) and HATU (70.0 mg, 0.184 mmol) in DMA (1 mL) is stirred for 15 min and added to a mixture of 0 (36.5 mg, 0.170 mmol) and DIPEA (0.086 mL, 0.496 mmol) in DMA (0.5 mL). The resultant mixture is shaken at 40° C. for 16 h. The crude reaction mixture is treated with water (0.1 mL) and purified using a reverse phase HPLC (C-18 column, eluting with 5% to 95% acetonitrile in water containing 0.1% TFA) to give the title product (2).

The following compounds are prepared according to the procedure described for the synthesis of compound 2 using the appropriate intermediates that are described in preceding sections:

6-[1-(4-phenoxybenzoyl)piperidin-4-yl]pyridazin-3-amine (Compound 3)
6-(1-{4-[4-(trifluoromethoxy)phenoxy]benzoyl}piperidin-4-yl)pyridazin-3-amine (Compound 4)
6-{1-[4-(4-methylphenoxy)benzoyl]piperidin-4-yl}pyridazin-3-amine (Compound 5)
6-{4-[4-(4-cyclopropylphenoxy)benzoyl]piperazin-1-yl}pyridazin-3-amine (Compound 6)
4-{4-[4-(6-aminopyridazin-3-yl)piperazine-1-carbonyl]phenoxy}benzonitrile (Compound 7)
6-{4-[4-(2H-1,3-benzodioxol-5-yloxy)benzoyl]piperazin-1-yl}pyridazin-3-amine (Compound 8)
6-{1-[4-(4-methoxyphenoxy)benzoyl]piperidin-4-yl}pyridazin-3-amine (Compound 9)
6-{1-[4-(4-fluorophenoxy)benzoyl]piperidin-4-yl}pyridazin-3-amine (Compound 10)
6-{4-[4-(4-chlorophenoxy)benzoyl]piperazin-1-yl}pyridazin-3-amine (Compound 11)
6-{1-[4-(4-cyclopropylphenoxy)benzoyl]piperidin-4-yl}pyridazin-3-amine (Compound 12)
6-{1-[4-(4-chlorophenoxy)benzoyl]piperidin-4-yl}pyridazin-3-amine (Compound 13)
5-{4-[4-(4-ethylphenoxy)benzoyl]piperazin-1-yl}pyridin-2-amine (Compound 14)
5-[4-(4-phenoxybenzoyl)piperazin-1-yl]pyridin-2-amine (Compound 15)
1-(4-{4-[4-(6-aminopyridazin-3-yl)piperidine-1-carbonyl]phenoxy}phenyl)ethan-1-one (Compound 16)
6-(1-{4-[4-(propan-2-yl)phenoxy]benzoyl}piperidin-4-yl)pyridazin-3-amine (Compound 17)
6-(4-{4-[4-(propan-2-yl)phenoxy]benzoyl}piperazin-1-yl)pyridazin-3-amine (Compound 18)
5-(4-{4-[4-(trifluoromethyl)phenoxy]benzoyl}piperazin-1-yl)pyridin-2-amine (Compound 19)
6-{4-[4-(4-ethylphenoxy)benzoyl]piperazin-1-yl}pyridazin-3-amine (Compound 20)
6-(4-{4-[4-(trifluoromethoxy)phenoxy]benzoyl}piperazin-1-yl)pyridazin-3-amine (Compound 21)
6-(4-{4-[3-fluoro-4-(trifluoromethyl)phenoxy]benzoyl}piperazin-1-yl)pyridazin-3-amine (Compound 22)
6-{1-[4-(4-ethylphenoxy)benzoyl]piperidin-4-yl}pyridazin-3-amine (Compound 23)
6-[4-(4-phenoxybenzoyl)piperazin-1-yl]pyridazin-3-amine (Compound 24)
4-{4-[4-(6-aminopyridazin-3-yl)piperazine-1-carbonyl]phenoxy}-N,N-dimethylbenzamide (Compound 25)
6-(4-{4-[4-(trifluoromethyl)phenoxy]benzoyl}piperazin-1-yl)pyridazin-3-amine (Compound 26)

Example 27

5-{4-[2-Fluoro-4-(4-fluorophenoxy)benzoyl]-4,7-diazaspiro[2.5]octan-7-yl}-4-methoxypyridin-2-amine Methyl 2-fluoro-4-(4-fluorophenoxy)benzoate

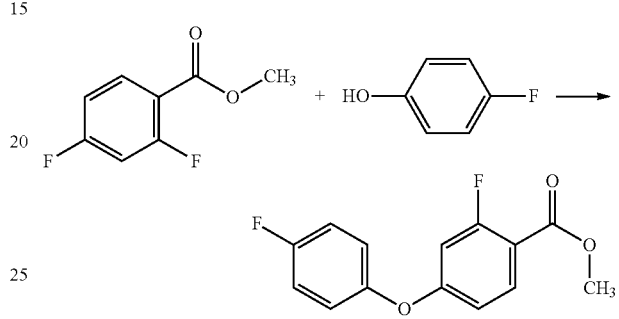

Methyl 2,4-difluorobenzoate (1.00 g; 5.81 mmol), 4-fluorophenol (0.72 g; 6.39 mmol) and potassium carbonate (1.61 g; 11.62 mmol) in DMF (20 mL) are stirred at 90° C. for 4 hours. The reaction mixture is diluted with water and extracted three times with DCM. The combined organic layers are dried over $MgSO_4$, filtered and concentrated under reduced pressure. The residue is purified by RP-HPLC (ACN/water+TFA).

Yield: 0.45 g (29%) ESI-MS: m/z=265 $[M+H]^+$
$R_t$(HPLC): 1.15 min (method 1)

2-Fluoro-4-(4-fluorophenoxy)benzoic Acid

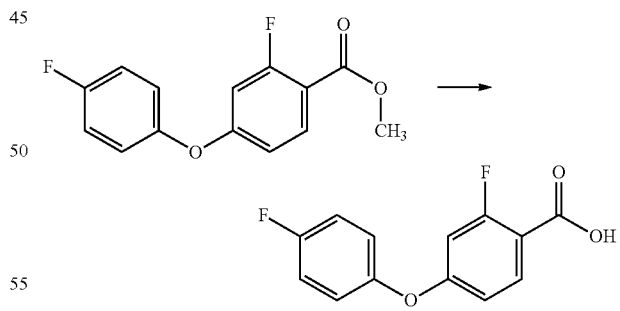

Methyl 2-fluoro-4-(4-fluorophenoxy)benzoate (0.45 g; 1.70 mmol) and NaOH (1 mol/L; aq. solution; 5.11 mL; 5.11 mmol) in MeOH (20 mL) are stirred at 50° C. for 2 hours. The organic solvent is evaporated and the remaining reaction mixture is acidified with HCl (1 mol/L; aq. solution). The resulting precipitate is filtered, washed with water and dried in a drying oven.

Yield: 0.40 g (94%) ESI-MS: m/z=251 $[M+H]^+$
$R_t$(HPLC): 1.02 min (method 1)

5-Bromo-2-(2,5-dimethyl-1H-pyrrol-1-yl)-4-methoxypyridine

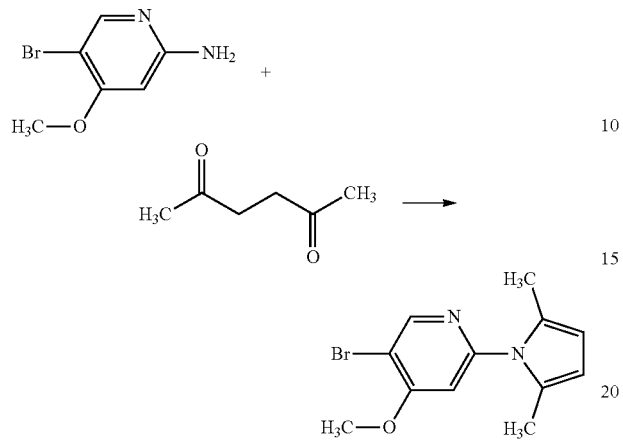

5-Bromo-4-methoxy-pyridin-2-ylamine (9.50 g, 46.79 mmol), hexane-2,5-dione (7.08 mL, 60.83 mmol) and p-toluenesulfonic acid (0.81 g, 4.68 mmol) in toluene (80 mL) are stirred over night at 120° C. using a Dean-Stark-apparatus. The reaction mixture is concentrated under reduced pressure, taken up in DCM and purified by silica gel chromatography (DCM).

Yield: 7.60 g (58%) ESI-MS: m/z=281 and 283 [M+H]$^+$ (Br-isotopic pattern) R$_f$(HPLC): 1.13 min (method 1)

tert-Butyl 7-[6-(2,5-dimethyl-1H-pyrrol-1-yl)-4-methoxypyridin-3-yl]-4,7-diazaspiro[2.5]octane-4-carboxylate

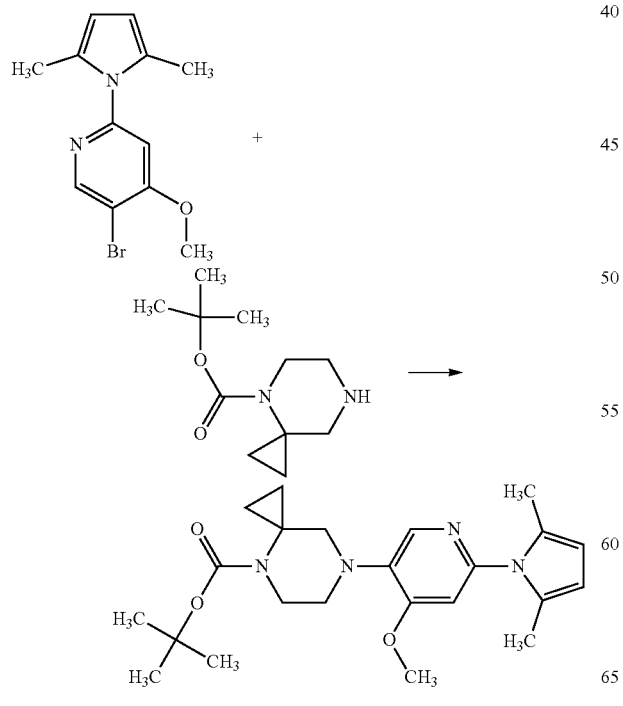

The reaction is performed under an argon-atmosphere. 5-Bromo-2-(2,5-dimethyl-1H-pyrrol-1-yl)-4-methoxypyridine (1.55 g; 5.50 mmol), tert-butyl 4,7-diazaspiro[2.5]octane-4-carboxylate (1.20 g; 5.65 mmol), CPhos-Pd-3G catalyst (0.44 g; 0.55 mmol) and cesium carbonate (5.38 g; 16.50 mmol) in 1,4-dioxane (40 mL) are stirred over night at 80° C. The reaction mixture is filtered and concentrated under reduced pressure. The residue is taken up in EtOAc and washed several times with water. The organic layer is separated, dried over Na$_2$SO$_4$, filtered and concentrated under reduced pressure.

Yield: quantitative ESI-MS: m/z=413 [M+H]$^+$ R$_f$(HPLC): 1.07 min (method 1)

7-[6-(2,5-Dimethyl-1H-pyrrol-1-yl)-4-methoxypyridin-3-yl]-4,7-diazaspiro[2.5]octane*trifluoroacetic Acid

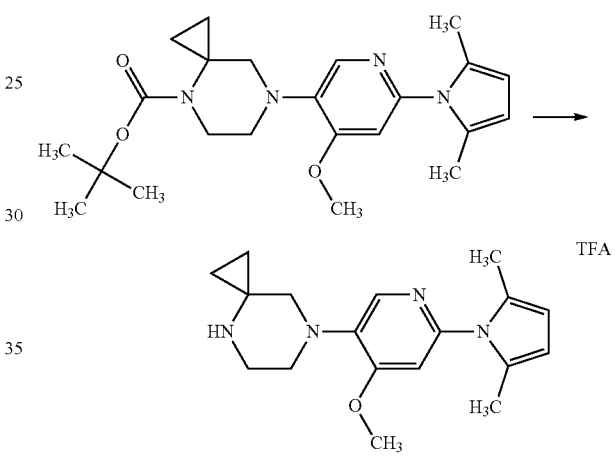

tert-Butyl 7-[6-(2,5-dimethyl-1H-pyrrol-1-yl)-4-methoxypyridin-3-yl]-4,7-diazaspiro[2.5]octane-4-carboxylate (2.30 g; 5.58 mmol) and TFA (2.00 mL; 25.92 mmol) in DCM (50 mL) are stirred at RT overnight. The same amount of TFA is added and the reaction mixture is stirred for 4 hours at 45° C. The reaction mixture is concentrated under reduced pressure and used without further purification.

Yield: quantitative ESI-MS: m/z=313 [M+H]$^+$ R$_f$(HPLC): 0.70 min (method 1)

5-{4,7-Diazaspiro[2.5]octan-7-yl}-4-methoxypyridin-2-amine

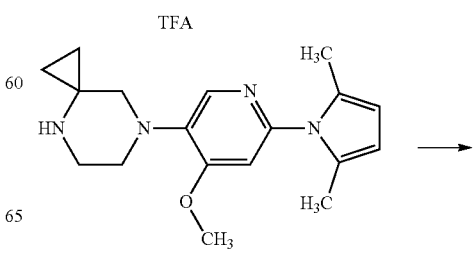

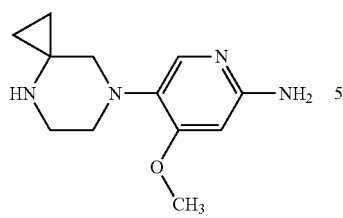

7-[6-(2,5-Dimethyl-1H-pyrrol-1-yl)-4-methoxypyridin-3-yl]-4,7-diazaspiro[2.5]octane*trifluoroacetic acid (2.00 g; 4.69 mmol), hydroxylamine hydrochloride (1.96 g; 28.14 mmol) and TEA (1.30 mL; 9.26 mmol) in EtOH/water (2/1; 100 mL) are stirred at 90° C. overnight. The organic solvent is evaporated and the remaining aqueous layer is washed several times with DCM. The aqueous layer is concentrated under reduced pressure and purified by RP-HPLC (ACN/water/NH$_4$OH). The product is triturated in PE and filtered. The desired product is used without further purification.

Yield: quantitative ESI-MS: m/z=235 [M+H]$^+$ R$_f$(HPLC): 0.60 min (method 3)

5-{4-[2-Fluoro-4-(4-fluorophenoxy)benzoyl]-4,7-diazaspiro[2.5]octan-7-yl}-4-methoxypyridin-2-amine

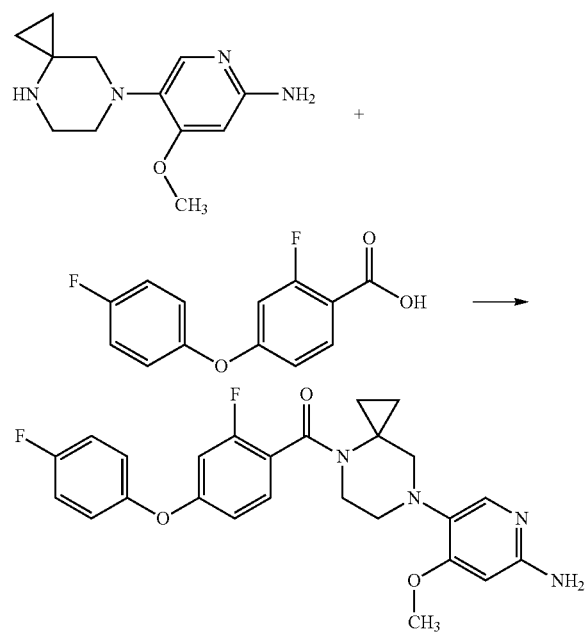

2-Fluoro-4-(4-fluorophenoxy)benzoic acid (30.0 mg; 0.12 mmol), HATU (45.6 mg; 0.12 mmol) and DIPEA (69.2 µL; 0.40 mmol) in DMF (2 mL) are stirred at RT for 5 minutes. 5-{4,7-Diazaspiro[2.5]octan-7-yl}-4-methoxypyridin-2-amine (23.4 mg; 0.10 mmol) is added. After stirring for 1 hour the reaction mixture is purified by RP-HPLC (ACN/water/NH$_4$OH).

Yield: 11.0 mg (24%) ESI-MS: m/z=467 [M+H]$^+$ R$_f$(HPLC): 0.99 min (method 3)

Example 28

5-{4-[2,5-Difluoro-4-(4-fluorophenoxy)benzoyl]-4,7-diazaspiro[2.5]octan-7-yl}-4-methoxypyridin-2-amine 2,5-Difluoro-4-(4-fluorophenoxy)benzoic Acid

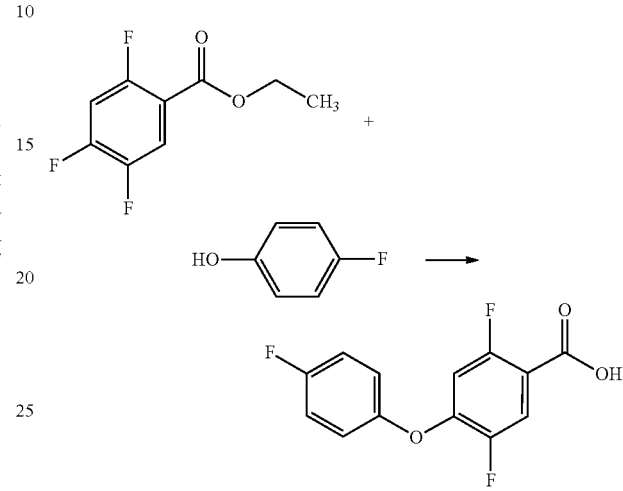

Ethyl 2,4,5-trifluorobenzoate (0.50 g; 2.45 mmol, commercially available CAS-Nr.: 351354-41-1), 4-fluorophenol (0.30 g; 2.69 mmol) and potassium carbonate (0.68 g; 4.90 mmol) in DMF (2 mL) are stirred at 80° C. for 2 hours. The reaction mixture is diluted with water and extracted three times with DCM. The combined organic layers are dried over MgSO$_4$, filtered and concentrated under reduced pressure. The residue is taken up in MeOH (20 mL) and NaOH (1 mol/L; aq. solution; 7.35 mL; 7.35 mmol) is added. After stirring at 50° C. for 2 hours the organic solvent is evaporated. The remaining aqueous layer is acidified with HCl (1 mol/L; aq. solution). The resulting precipitate is filtered, washed with water and dried in a drying oven.

Yield: 0.63 g (96%) ESI-MS: m/z=269 [M+H]$^+$ R$_f$(HPLC): 1.04 min (method 1)

5-{4-[2,5-Difluoro-4-(4-fluorophenoxy)benzoyl]-4,7-diazaspiro[2.5]octan-7-yl}-4-methoxypyridin-2-amine

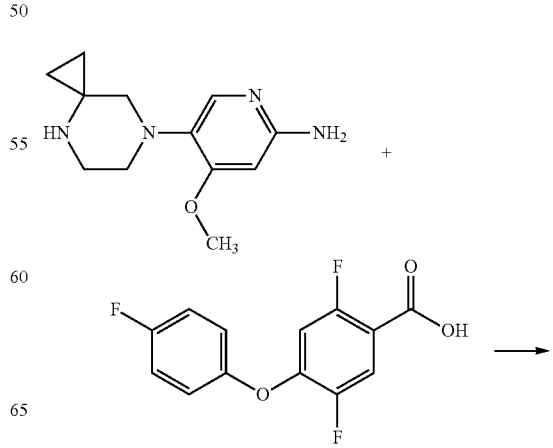

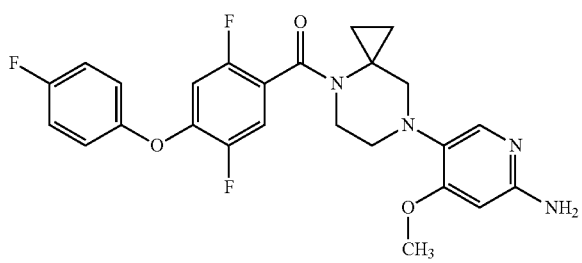

2,5-Difluoro-4-(4-fluorophenoxy)benzoic acid (32.2 mg; 0.12 mmol), HATU (45.6 mg; 0.12 mmol) and DIPEA (69.2 µL; 0.40 mmol) in DMF (2 mL) are stirred at RT for 5 minutes. 5-{4,7-Diazaspiro[2.5]octan-7-yl}-4-methoxypyridin-2-amine (23.4 mg; 0.10 mmol) is added. After stirring for 1 hour the reaction mixture is purified by RP-HPLC (ACN/water/NH$_4$OH).

Yield: 14.0 mg (29%) ESI-MS: m/z=485 [M+H]$^+$
R$_t$(HPLC): 1.00 min (method 3)

Example 29

5-{1-[2-Fluoro-4-(4-fluorophenoxy)-5-methoxybenzoyl]piperidin-4-yl}-4-methoxypyridin-2-amine 2-Fluoro-4-(4-fluorophenoxy)-5-methoxybenzoic Acid

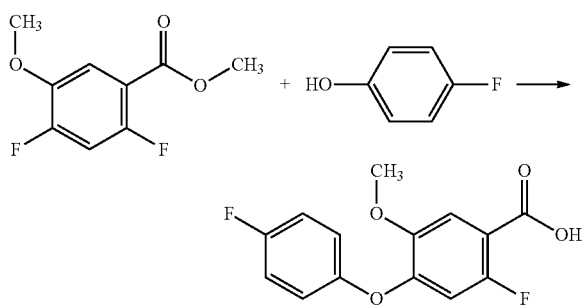

Methyl 2,4-difluoro-5-methoxybenzoate (0.70 g; 3.46 mmol, commercially available CAS-Nr. 1804416-21-4)), 4-fluorophenol (0.43 g; 3.81 mmol) and potassium carbonate (0.96 g; 6.93 mmol) in DMF (20 mL) are stirred at 90° C. for 2 hours. The reaction mixture is filtered and purified by RP-HPLC (ACN/water+TFA). The residue is taken up in MeOH (20 mL) and NaOH (1 mol/L; aq. solution; 6.93 mL; 6.93 mmol) is added. After stirring at 45° C. for 3 hours the reaction mixture is concentrated under reduced pressure. The residue is taken up in water and acidified to pH 5 using HCl (1 mol/L; aq. solution). The resulting precipitate is filtered and dried in a drying oven.

Yield: 0.65 g (67%) ESI-MS: m/z=281 [M+H]$^+$
R$_t$(HPLC): 1.01 min (method 1)

tert-Butyl 6-amino-4-methoxy-1',2',3',6'-tetrahydro-[3,4'-bipyridine]-1'-carboxylate

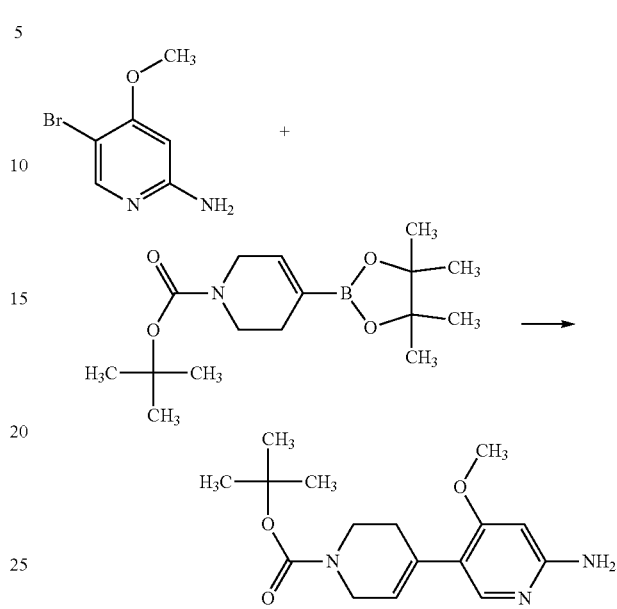

The reaction is performed under an argon-atmosphere. 5-Bromo-4-methoxypyridin-2-amine (7.40 g; 32.80 mmol), tert-butyl 4-(4,4,5,5-tetramethyl-1,3,2-dioxaborolan-2-yl)-1,2,3,6-tetrahydropyridine-1-carboxylate (11.16 g; 36.08 mmol) and sodium carbonate (2 mol/L; aq. solution; 65.60 mL; 131.21 mmol) in 1,4-dioxane (300 mL) is purged with argon. After 5 minutes Xphos 2$^{nd}$ generation catalyst (0.77 g; 0.98 mmol) is added and the reaction mixture is stirred over night in a sealed vial at 100° C. The reaction mixture is concentrated under reduced pressure. The residue is taken up in water and extracted several times with EtOAc. The combined organic layers are dried over Na$_2$SO$_4$, filtered and concentrated under reduced pressure. The residue is purified by silica gel chromatography (DCM/MeOH).

Yield: 9.69 g (97%) ESI-MS: m/z=306 [M+H]$^+$
R$_t$(HPLC): 0.83 min (method 2)

tert.-Butyl 4-(6-amino-4-methoxypyridin-3-yl)-piperidine-1-carboxylate

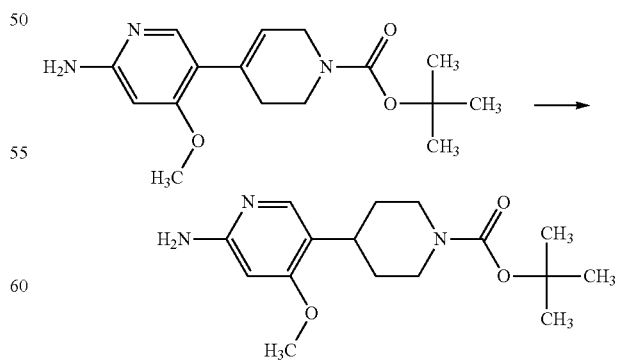

Under a hydrogen atmosphere (Parr-apparatus; 50 psi) tert-butyl 6-amino-4-methoxy-1',2',3',6'-tetrahydro-[3,4'-bipyridine]-1'-carboxylate (5.11 g; 16.73 mmol) and Pd/C (10%; 0.60 g) in MeOH (100 mL) are stirred at RT for 41.5 hours. During this time additional catalyst is added twice and the reaction mixture is further hydrogenated. After removal of the catalyst by filtration the mother liquid is concentrated under reduced pressure. The product is used without further purification.

Yield: 4.71 g (92%) ESI-MS: m/z=308 [M+H]+
R$_t$(HPLC): 0.82 min (method 2)

4-Methoxy-5-(piperidin-4-yl)pyridin-2-amine dihydrochloride

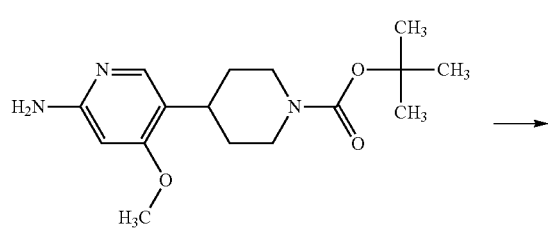

tert.-Butyl 4-(6-amino-4-methoxypyridin-3-yl)-piperidine-1-carboxylate (6.90 g; 22.45 mmol) and HCl (4 mol/L; solution in 1,4-dioxane; 69.00 mL; 276.0 mmol) in DCM (89.70 mL) are stirred at RT overnight. The reaction mixture is concentrated under reduced pressure. The residue is triturated in Et$_2$O and filtered. The desired product is used without further purification.

Yield: 5.30 g (84%) ESI-MS: m/z=208 [M+H]+
R$_t$(HPLC): 0.66 min (method 3)

5-{1-[2-Fluoro-4-(4-fluorophenoxy)-5-methoxybenzoyl]piperidin-4-yl}-4-methoxypyridin-2-amine

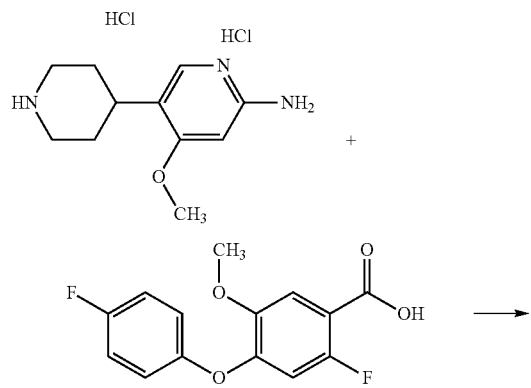

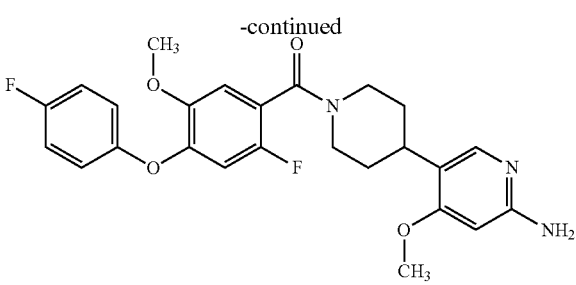

2-Fluoro-4-(4-fluorophenoxy)-5-methoxybenzoic acid (33.6 mg; 0.12 mmol), HATU (45.6 mg; 0.12 mmol) and DIPEA (69.2 μL; 0.40 mmol) in DMF (2 mL) are stirred at RT for 5 minutes. 4-Methoxy-5-(piperidin-4-yl)pyridin-2-amine dihydrochloride (28.0 mg; 0.10 mmol) is added. After stirring for 1 hour the reaction mixture is purified by RP-HPLC (ACN/water/NH$_4$OH).

Yield: 37.0 mg (79%) ESI-MS: m/z=470 [M+H]+
R$_t$(HPLC): 0.99 min (method 3)

Example 30

5-{1-[2,5-Difluoro-4-(4-fluorophenoxy)benzoyl]piperidin-4-yl}-4-methoxypyridin-2-amine

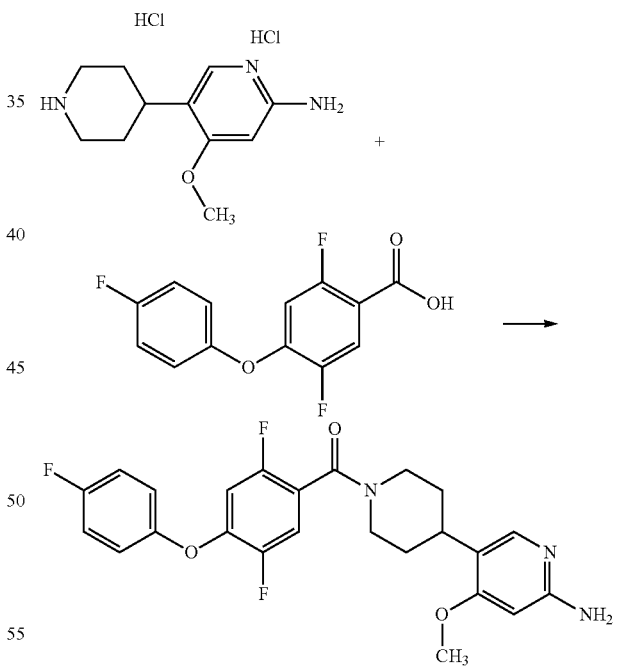

2,5-Difluoro-4-(4-fluorophenoxy)benzoic acid (32.2 mg; 0.12 mmol), HATU (45.6 mg; 0.12 mmol) and DIPEA (69.2 μL; 0.40 mmol) in DMF (2 mL) are stirred at RT for 5 minutes. 4-Methoxy-5-(piperidin-4-yl)pyridin-2-amine dihydrochloride (28.0 mg; 0.10 mmol) is added. After stirring for 1 hour the reaction mixture is purified by RP-HPLC (ACN/water/NH$_4$OH).

Yield: 29.1 mg (64%) ESI-MS: m/z=458 [M+H]+
R$_t$(HPLC): 0.81 min (method 6)

Example 31

5-{1-[2-Fluoro-4-(4-fluorophenoxy)benzoyl]piperidin-4-yl}-4-methoxypyridin-2-amine

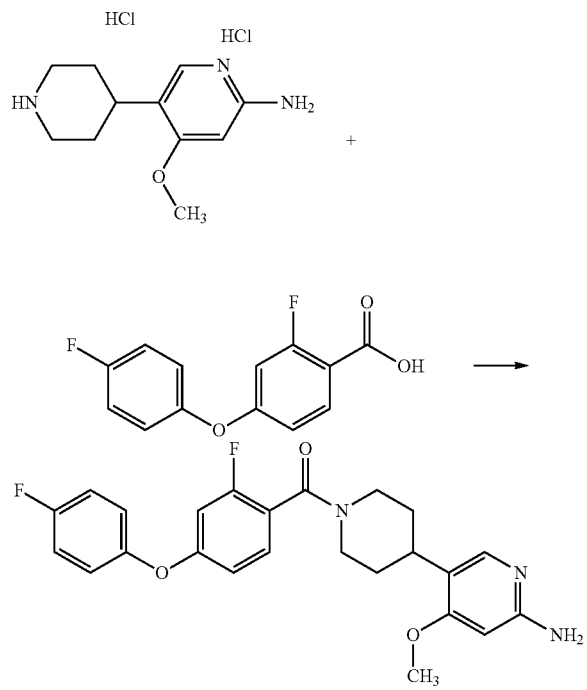

2-Fluoro-4-(4-fluorophenoxy)benzoic acid (30.0 mg; 0.12 mmol), HATU (45.6 mg; 0.12 mmol) and DIPEA (69.2 µL; 0.40 mmol) in DMF (2 mL) are stirred at RT for 5 minutes. 4-Methoxy-5-(piperidin-4-yl)pyridin-2-amine dihydrochloride (28.0 mg; 0.10 mmol) is added. After stirring for 1 hour the reaction mixture is purified by RP-HPLC (ACN/water/NH₄OH).

Yield: 28.2 mg (64%) ESI-MS: m/z=440 [M+H]⁺ R$_t$(HPLC): 0.80 min (method 6)

Example 32

5-{1-[4-(4-Fluorophenoxy)benzoyl]piperidin-4-yl}-4-methoxypyridin-2-amine

4-Methoxy-5-(piperidin-4-yl)pyridin-2-amine bis(trifluoroacetic Acid)

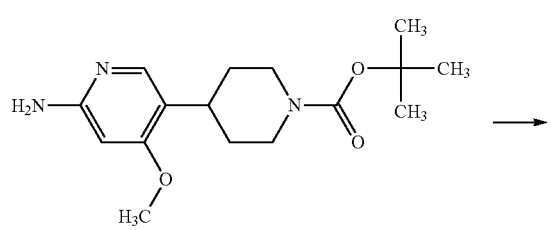

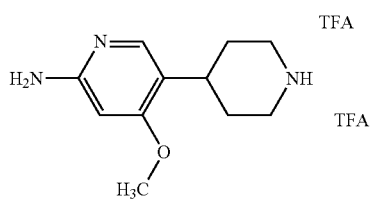

tert.-Butyl 4-(6-amino-4-methoxypyridin-3-yl)-piperidine-1-carboxylate (8.74 g; 28.43 mmol) and TFA (21.94 mL; 284.33 mmol) in DCM (200 mL) are stirred at RT overnight. The reaction mixture is concentrated under reduced pressure. The residue is triturated in diethyl ether, filtered and dried in a drying oven. The residue is used without further purification.

Yield: 10.60 g (86%) ESI-MS: m/z=208 [M+H]⁺ R$_t$(HPLC): 0.68 min (method 3)

5-{1-[4-(4-Fluorophenoxy)benzoyl]piperidin-4-yl}-4-methoxypyridin-2-amine*trifluoroacetic Acid

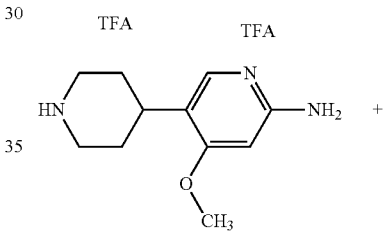

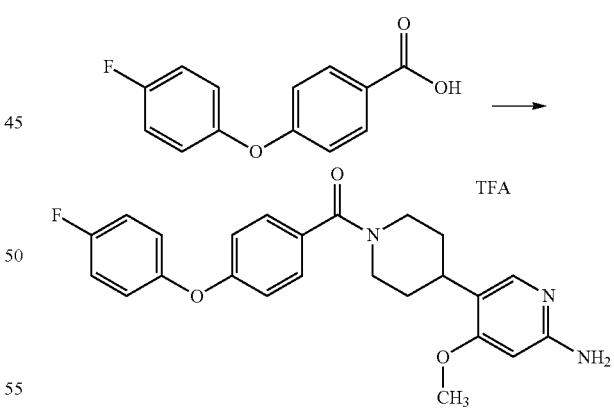

4-Methoxy-5-(piperidin-4-yl)pyridin-2-amine bis(trifluoroacetic acid) (46.9 mg; 0.11 mmol), 4-(4-fluorophenoxy)benzoic acid (25.0 mg; 0.11 mmol) and DIPEA (76.0 µL; 0.44 mmol) in DMF (2 mL) are stirred at RT. HATU (40.9 mg; 0.11 mmol) is added. After stirring over night the reaction mixture is purified by RP-HPLC (ACN/water+TFA).

Yield: 32.9 mg (57%) ESI-MS: m/z=422 [M+H]⁺ R$_t$(HPLC): 0.65 min (method 11)

Example 33

5-{1-[2-Fluoro-5-methoxy-4-(2-methylpropoxy)benzoyl]piperidin-4-yl}-4-methoxypyridin-2-amine Methyl 2-fluoro-4-hydroxy-5-methoxybenzoate

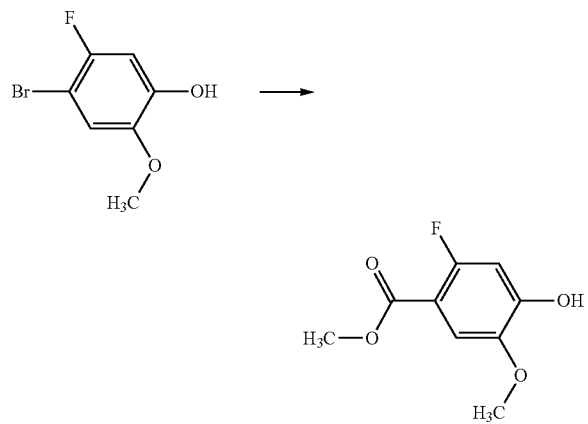

Under a carbon monoxide atmosphere (5 bar), 4-bromo-5-fluoro-2-methoxyphenol (0.31 g, 1.40 mmol), anhydrous sodium acetate (0.13 mg, 1.54 mmol), [1,1'-bis(diphenylphosphino)-ferrocene]-dichloropalladium-(II) complex with dichloromethane (1:1) (0.06 mg, 0.07 mmol) in methanol (25 mL) are stirred at 100° C. for 19 h. The solvent is removed under reduced pressure. The residue is dissolved in an appropriate volume of DMF and filtered over a PL-Thiol cartridge (volume 1 mL, pre-washed with MeOH). The cartridge is eluted with an appropriate volume of DMF/MeOH (ratio 9/1). The solvents are concentrated under reduced pressure and the residue is purified by RP-HPLC (ACN/water+TFA).

Yield: 0.18 g (64%) ESI-MS: m/z=201 [M+H]$^+$
R$_f$(HPLC): 0.84 min (method 1)

2-Fluoro-4-hydroxy-5-methoxybenzoic Acid

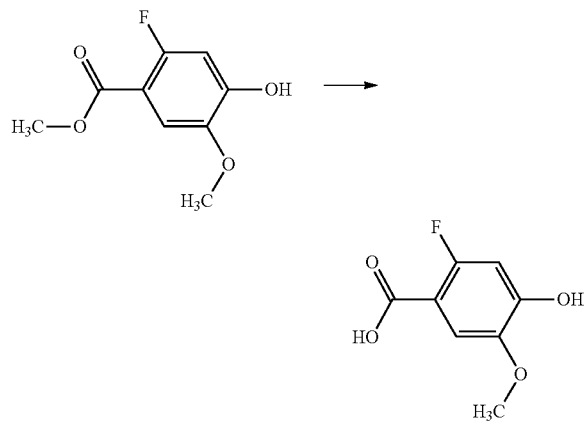

Methyl 2-fluoro-4-hydroxy-5-methoxybenzoate (0.70 g, 3.50 mmol, commercially available CAS-No. 1935364-074)) in 20 THF and 2 mL Methanol is stirred at RT and 8 mL of a 1 M aqueous LiOH solution (8.0 mmol) is added. The reaction mixture is stirred at 50° C. overnight. Additional 2 mL of a 1M aqueous LiOH solution (2.0 mmol) is added and stirred at 60° C. overnight. The organic solvents are removed under reduced pressure and the aqueous layer is acidified with aqueous 4 M HCL solution. The resulting precipitate is filtered and dried at 45° C. in a drying oven.

Yield: 0.63 g (96%) ESI-MS: m/z=187 [M+H]$^+$
R$_f$(HPLC): 0.59 min (method 2)

4-[4-(6-Amino-4-methoxypyridin-3-yl)piperidine-1-carbonyl]-5-fluoro-2-methoxyphenol

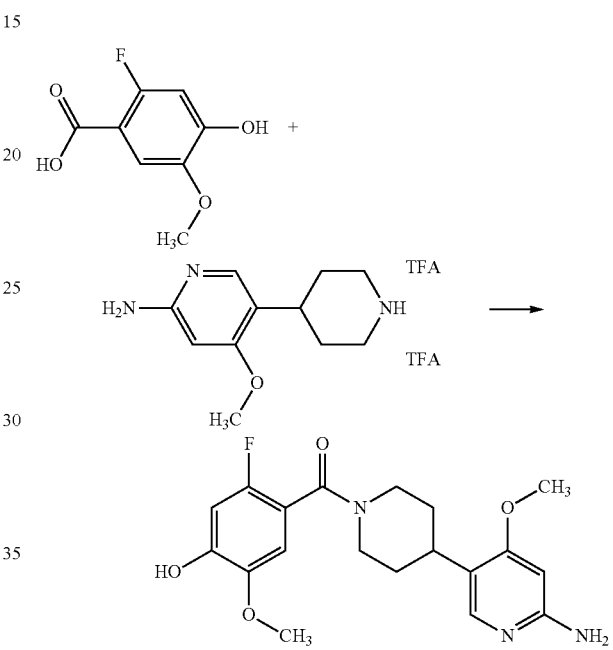

2-Fluoro-4-hydroxy-5-methoxybenzoic acid (0.20 g; 1.06 mmol), 4-methoxy-5-(piperidin-4-yl)pyridin-2-amine bis (trifluoroacetic acid) (0.46 g; 1.06 mmol) and DIPEA (0.75 mL; 4.34 mmol) in DMF (6 mL) are stirred at RT. HATU (0.40 g; 1.06 mmol) is added. After stirring over night the reaction mixture is diluted with water and extracted with DCM. The organic layer is separated and concentrated under reduced pressure. The residue is purified by silica gel chromatography (DCM/MeOH).

Yield: 0.12 g (30%) ESI-MS: m/z=376 [M+H]$^+$
R$_f$(HPLC): 0.71 min (method 2)

5-{1-[2-Fluoro-5-methoxy-4-(2-methylpropoxy)benzoyl]piperidin-4-yl}-4-methoxypyridin-2-amine trifluoroacetic Acid

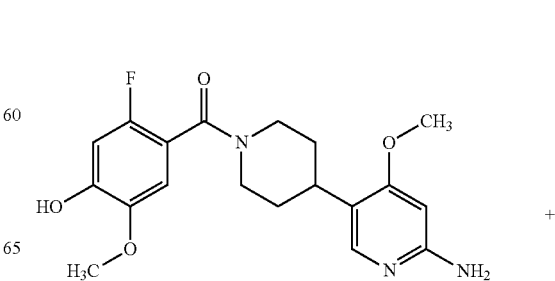

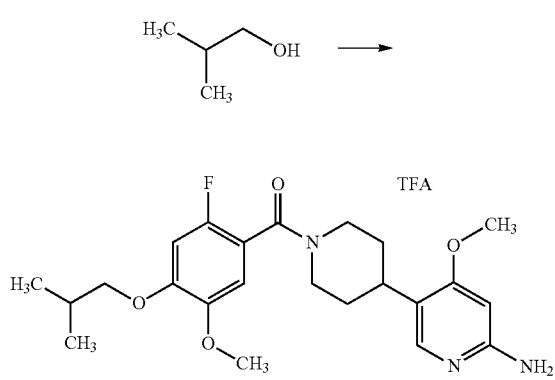

4-[4-(6-Amino-4-methoxypyridin-3-yl)piperidine-1-carbonyl]-5-fluoro-2-methoxyphenol (20.0 mg; 0.05 mmol), 2-methylpropan-1-ol (11.1 µL; 0.12 mmol), TPP (40.0 mg; 0.15 mmol) and DTAD (30.0 mg; 0.13 mmol) in 1,4-dioxane (3 mL) are stirred for 1 hour at 60° C. The reaction mixture is purified by RP-HPLC (ACN/water+TFA).

Yield: 11.6 mg (40%) ESI-MS: m/z=432 [M+H]$^+$
R$_t$(HPLC): 0.79 min (method 8)

Example 34

5-(1-{2-Fluoro-5-methoxy-4-[(3-methylcyclobutyl)methoxy]benzoyl}piperidin-4-yl)-4-methoxypyridin-2-amine trifluoroacetic Acid

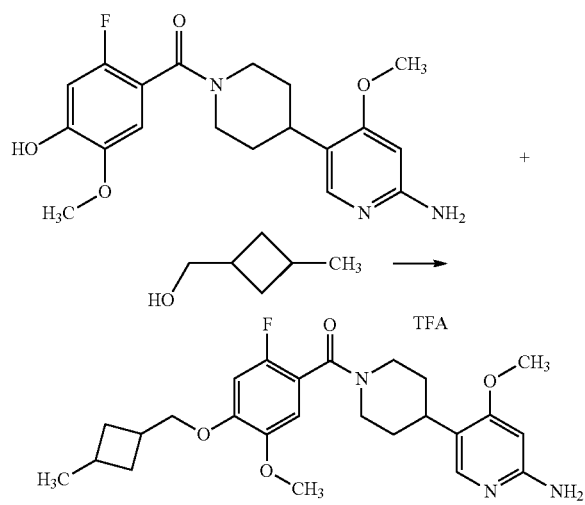

4-[4-(6-Amino-4-methoxypyridin-3-yl)piperidine-1-carbonyl]-5-fluoro-2-methoxyphenol (20.0 mg; 0.05 mmol), (3-methylcyclobutyl)methanol (12.0 mg; 0.12 mmol), TPP (40.0 mg; 0.15 mmol) and DTAD (30.0 mg; 0.13 mmol) in 1,4-dioxane (3 mL) are stirred for 1 hour at 60° C. The reaction mixture is purified by RP-HPLC (ACN/water+TFA).

Yield: 6.8 mg (22%) ESI-MS: m/z=458 [M+H]$^+$
R$_t$(HPLC): 0.87 min (method 8)

Example 35

5-{1-[4-(Cyclopropylmethoxy)-2-fluoro-5-methoxybenzoyl]piperidin-4-yl}-4-methoxypyridin-2-amine trifluoroacetic Acid

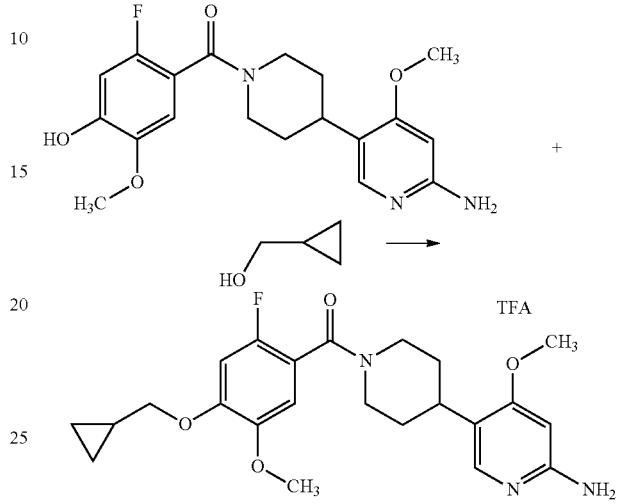

4-[4-(6-Amino-4-methoxypyridin-3-yl)piperidine-1-carbonyl]-5-fluoro-2-methoxyphenol (25.0 mg; 0.07 mmol), cyclopropylmethanol (16.2 µL; 0.20 mmol), TPP (34.9 mg; 0.13 mmol) and DTAD (30.7 mg; 0.13 mmol) in 1,4-dioxane (3 mL) are stirred for 2 hours at 60° C. The reaction mixture is purified by RP-HPLC (ACN/water+TFA).

Yield: 21.0 mg (36%) ESI-MS: m/z=430 [M+H]$^+$
R$_t$(HPLC): 0.86 min (method 3)

Example 36

5-{1-[4-(Cyclobutylmethoxy)-2-fluoro-5-methoxybenzoyl]piperidin-4-yl}-4-methoxypyridin-2-amine trifluoroacetic Acid

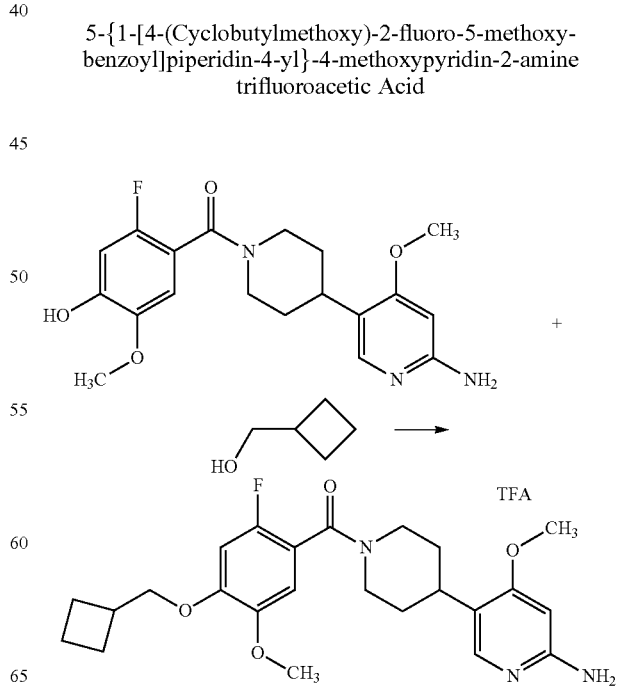

4-[4-(6-Amino-4-methoxypyridin-3-yl)piperidine-1-carbonyl]-5-fluoro-2-methoxyphenol (25.0 mg; 0.07 mmol), cyclobutylmethanol (19.3 µL; 0.20 mmol), TPP (34.9 mg; 0.13 mmol) and DTAD (30.7 mg; 0.13 mmol) in 1,4-dioxane (2 mL) are stirred for 2 hours at 60° C. The reaction mixture is purified by RP-HPLC (ACN/water+TFA).

Yield: 23.0 mg (62%) ESI-MS: m/z=444 [M+H]⁺ R_f(HPLC): 0.91 min (method 1)

Example 37

5-(1-{4-[(3,3-Difluorocyclobutyl)methoxy]-2-fluoro-5-methoxybenzoyl}piperidin-4-yl)-4-methoxypyridin-2-amine trifluoroacetic Acid

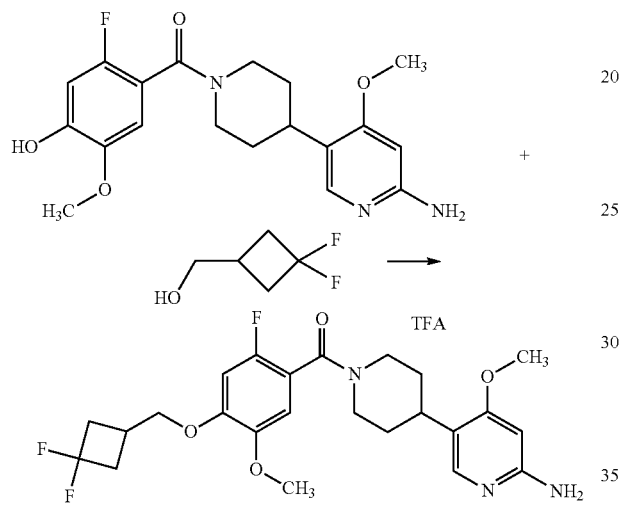

4-[4-(6-Amino-4-methoxypyridin-3-yl)piperidine-1-carbonyl]-5-fluoro-2-methoxyphenol (20.0 mg; 0.05 mmol), (3,3-difluorocyclobutyl)methanol (14.7 mg; 0.12 mmol), TPP (40.0 mg; 0.15 mmol) and DTAD (30.0 mg; 0.13 mmol) in 1,4-dioxane (3 mL) are stirred for 1 hour at 60° C. The reaction mixture is purified by RP-HPLC (ACN/water+TFA).

Yield: 11.5 mg (36%) ESI-MS: m/z=480 [M+H]⁺ R_f(HPLC): 0.74 min (method 8)

Example 38

5-[1-(2-Fluoro-4-{[trans-2-methylcyclopropyl]methoxy}benzoyl)piperidin-4-yl]-4-methoxypyridin-2-amine 4-[4-(6-Amino-4-methoxypyridin-3-yl)piperidine-1-carbonyl]-3-fluorophenol

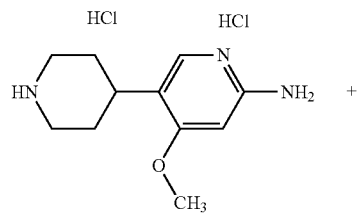

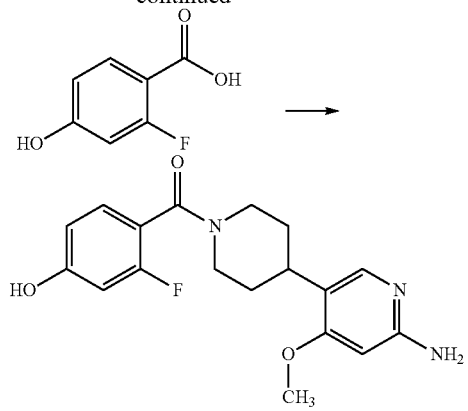

2-Fluoro-4-hydroxybenzoic acid (1.25 g; 8.01 mmol), TBTU (2.57 g; 8.01 mmol) and DIPEA (7.00 mL; 40.69 mmol) in DMF (40 mL) are stirred at RT for 5 minutes. 4-Methoxy-5-(piperidin-4-yl)pyridin-2-amine dihydrochloride (2.33 g; 8.33 mmol) is added. After stirring at 50° C. for 2 hours additional 2-fluoro-4-hydroxybenzoic acid and TBTU is added and stirred at 50° C. overnight. The reaction mixture is purified by RP-HPLC (ACN/water/NH₄OH) and additional purification (ACN/water+TFA) and subsequently once again (ACN/water/NH₄OH).

Yield: 1.80 g (65%) ESI-MS: m/z=346 [M+H]⁺ R_f(HPLC): 0.72 min (method 1)

5-[1-(2-Fluoro-4-{[trans-2-methylcyclopropyl]methoxy}benzoyl)piperidin-4-yl]-4-methoxypyridin-2-amine

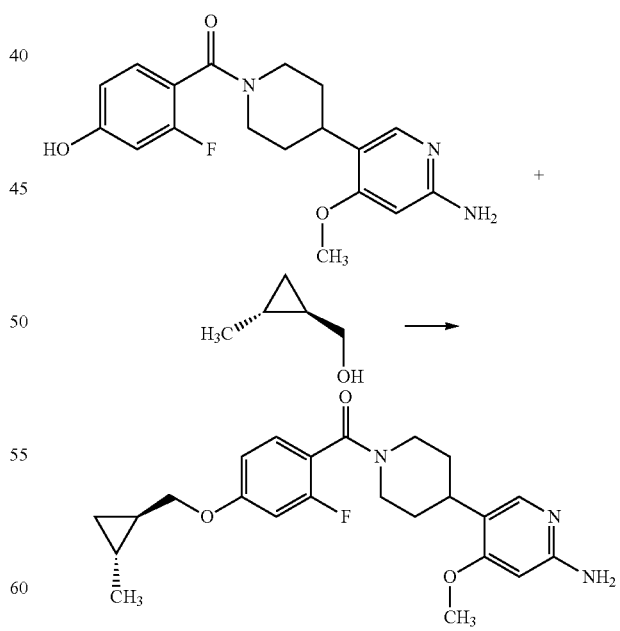

4-[4-(6-Amino-4-methoxypyridin-3-yl)piperidine-1-carbonyl]-3-fluorophenol (25.0 mg; 0.07 mmol), [trans-2-methylcyclopropyl]methanol (14.6 µL; 0.17 mmol), TPP (50.0 mg; 0.19 mmol) and DTAD (40.0 mg; 0.17 mmol) in 1,4-dioxane (3 mL) are stirred for 1 hour at 60° C. The reaction mixture is purified by RP-HPLC (ACN/water/NH₄OH).

Yield: 16.3 mg (36%) ESI-MS: m/z=414 [M+H]⁺ R_f(HPLC): 0.67 min (method 6)

Example 39

5-[1-(2-Fluoro-4-propoxybenzoyl)piperidin-4-yl]-4-methoxypyridin-2-amine trifluoroacetic Acid

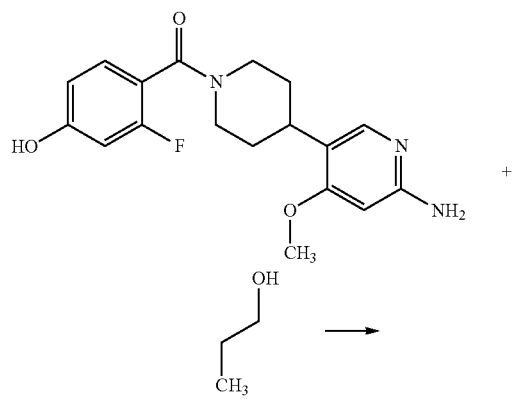

4-[4-(6-Amino-4-methoxypyridin-3-yl)piperidine-1-carbonyl]-3-fluorophenol (25.0 mg; 0.07 mmol), propan-1-ol (12.2 µL; 0.17 mmol), TPP (50.0 mg; 0.19 mmol) and DTAD (40.0 mg; 0.17 mmol) in 1,4-dioxane (3 mL) are stirred for 1 hour at 60° C. The reaction mixture is purified by RP-HPLC (ACN/water+TFA).

Yield: 25.7 mg (71%) ESI-MS: m/z=388 [M+H]⁺ R_f(HPLC): 0.62 min (method 11)

Example 40

5-(1-{2-Fluoro-4-[(1,2,3-thiadiazol-4-yl)methoxy]benzoyl}piperidin-4-yl)-4-methoxypyridin-2-amine trifluoroacetic Acid

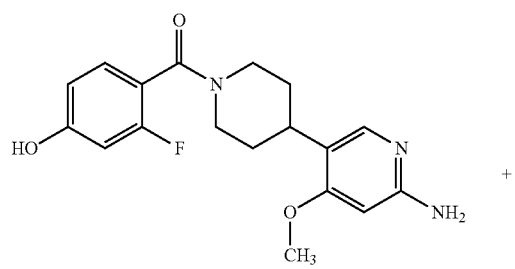

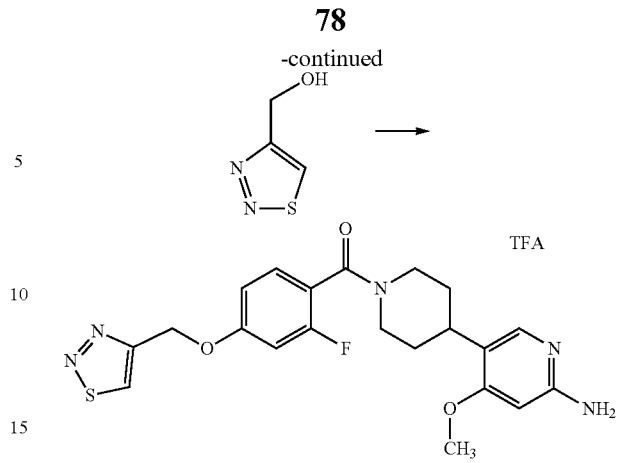

4-[4-(6-Amino-4-methoxypyridin-3-yl)piperidine-1-carbonyl]-3-fluorophenol (25.0 mg; 0.07 mmol), (1,2,3-thiadiazol-4-yl)methanol (19.7 mg; 0.17 mmol), TPP (50.0 mg; 0.19 mmol) and DTAD (40.0 mg; 0.17 mmol) in 1,4-dioxane (3 mL) are stirred for 1 hour at 60° C. The reaction mixture is purified by RP-HPLC (ACN/water+TFA).

Yield: 23.7 mg (59%) ESI-MS: m/z=444 [M+H]⁺ R_f(HPLC): 0.51 min (method 11)

Example 41

5-{1-[4-(Cyclohexylmethoxy)-2-fluorobenzoyl]piperidin-4-yl}-4-methoxypyridin-2-amine trifluoroacetic Acid

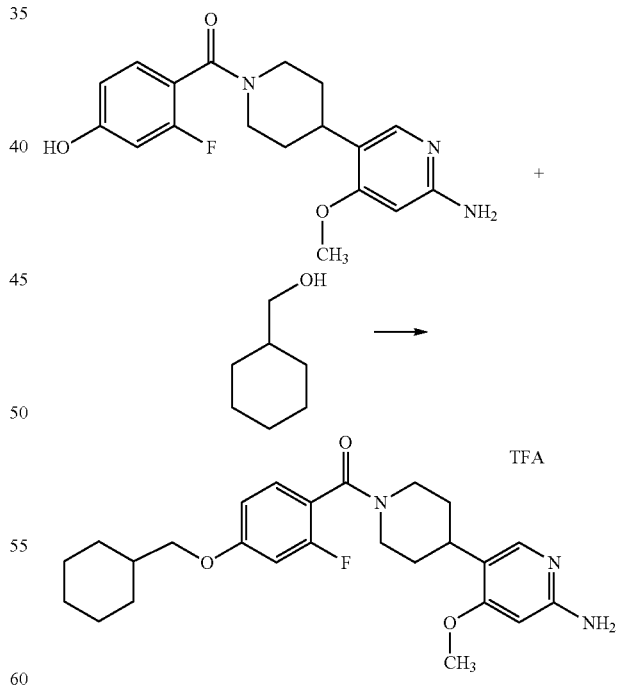

4-[4-(6-Amino-4-methoxypyridin-3-yl)piperidine-1-carbonyl]-3-fluorophenol (25.0 mg; 0.07 mmol), cyclohexylmethanol (21.1 µL; 0.17 mmol), TPP (50.0 mg; 0.19 mmol) and DTAD (40.0 mg; 0.17 mmol) in 1,4-dioxane (3 mL) are stirred for 1 hour at 60° C. The reaction mixture is purified by RP-HPLC (ACN/water+TFA).

Yield: 27.3 mg (68%) ESI-MS: m/z=442.5 [M+H]⁺
$R_t$(HPLC): 0.78 min (method 11)

Example 42

5-{1-[4-(2-Cyclopropylethoxy)-2-fluorobenzoyl]piperidin-4-yl}-4-methoxypyridin-2-amine trifluoroacetic Acid

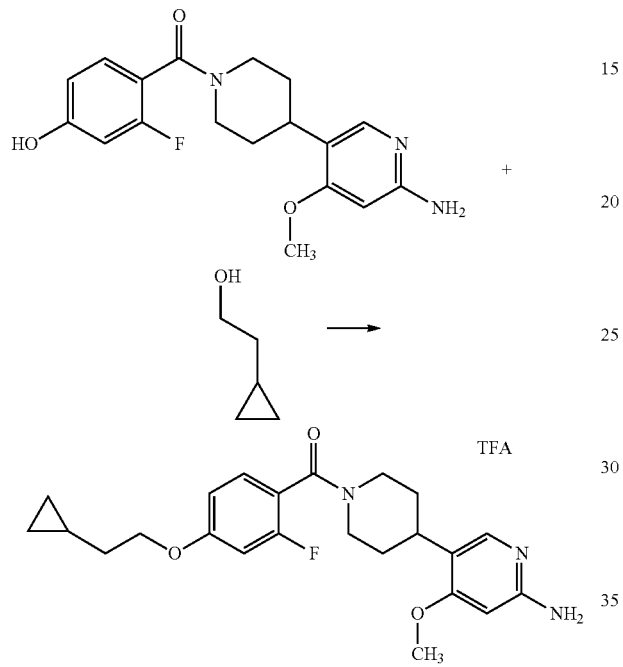

4-[4-(6-Amino-4-methoxypyridin-3-yl)piperidine-1-carbonyl]-3-fluorophenol (25.0 mg; 0.07 mmol), 2-cyclopropylethan-1-ol (14.6 mg; 0.17 mmol), TPP (50.0 mg; 0.19 mmol) and DTAD (40.0 mg; 0.17 mmol) in 1,4-dioxane (3 mL) are stirred for 1 hour at 60° C. The reaction mixture is purified by RP-HPLC (ACN/water+TFA).

Yield: 27.2 mg (71%) ESI-MS: m/z=414 [M+H]⁺
$R_t$(HPLC): 0.67 min (method 11)

Example 43

5-{1-[4-(Benzyloxy)-2-fluorobenzoyl]piperidin-4-yl}-4-methoxypyridin-2-amine trifluoroacetic Acid

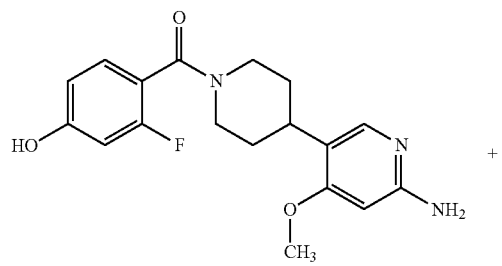

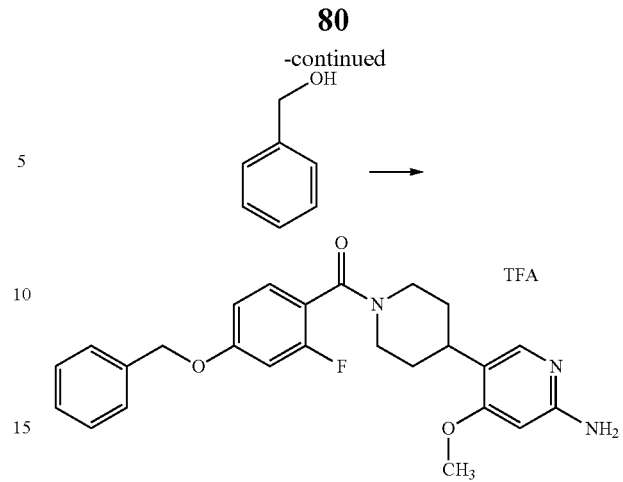

4-[4-(6-Amino-4-methoxypyridin-3-yl)piperidine-1-carbonyl]-3-fluorophenol (25.0 mg; 0.07 mmol), phenylmethanol (17.6 µL; 0.17 mmol), TPP (50.0 mg; 0.19 mmol) and DTAD (40.0 mg; 0.17 mmol) in 1,4-dioxane (3 mL) are stirred for 1 hour at 60° C. The reaction mixture is purified by RP-HPLC (ACN/water+TFA).

Yield: 26.5 mg (67%) ESI-MS: m/z=436 [M+H]⁺
$R_t$(HPLC): 0.66 min (method 11)

Example 44

5-{1-[4-(Cyclobutylmethoxy)-3-methoxybenzoyl]piperidin-4-yl}-4-methoxypyridin-2-amine 4-[4-(6-Amino-4-methoxypyridin-3-yl)piperidine-1-carbonyl]-2-methoxyphenol

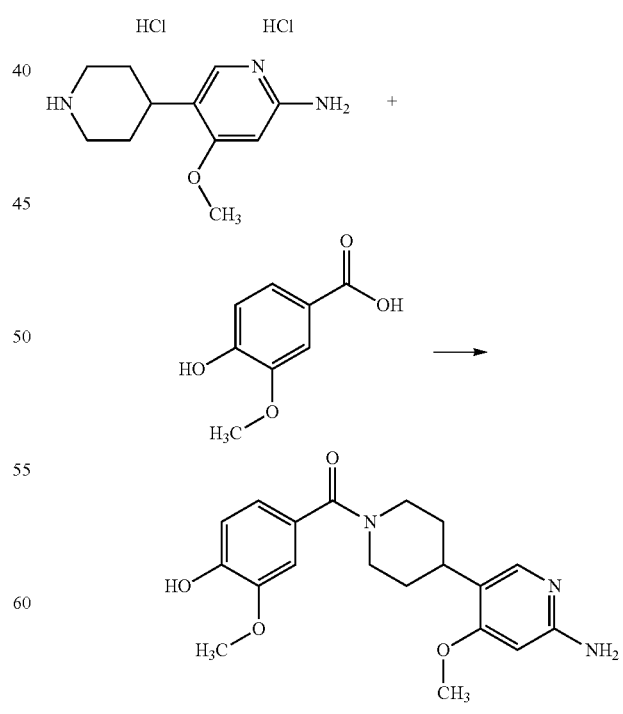

4-Hydroxy-3-methoxybenzoic acid (0.14 g; 0.86 mmol), HATU (0.33 g; 0.86 mmol) and DIPEA (0.49 mL; 2.86 mmol) in DMF (5 mL) are stirred at RT for 5 minutes. 4-Methoxy-5-(piperidin-4-yl)pyridin-2-amine dihydrochloride (0.20 g; 0.71 mmol) is added. After stirring at RT for 2 hours NaOH (1 mol/L; aq. solution; 0.5 mL) is added and stirred for 3 days. The reaction mixture is diluted with water, filtered and purified by RP-HPLC (ACN/water/NH₄OH).

Yield: 0.1 g (39%) ESI-MS: m/z=358 [M+H]⁺ R$_f$(HPLC): 0.69 min (method 3)

5-{1-[4-(Cyclobutylmethoxy)-3-methoxybenzoyl]piperidin-4-yl}-4-methoxypyridin-2-amine trifluoroacetic Acid

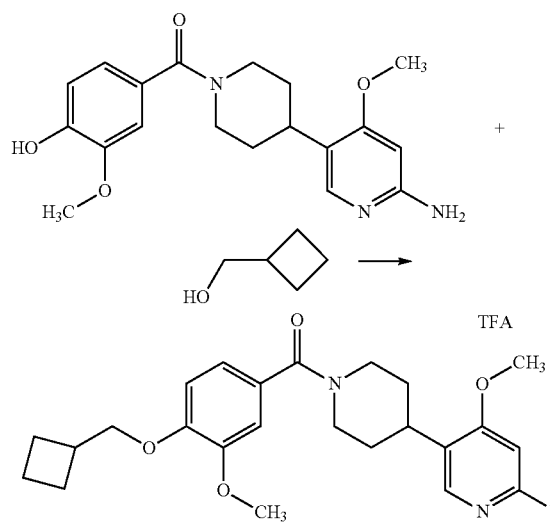

4-[4-(6-Amino-4-methoxypyridin-3-yl)piperidine-1-carbonyl]-2-methoxyphenol (25.0 mg; 0.07 mmol), cyclobutylmethanol (20.3 µL; 0.21 mmol), TPP (36.7 mg; 0.14 mmol) and DTAD (32.2 mg; 0.14 mmol) in 1,4-dioxane (2 mL) are stirred for 2 hours at 60° C. The reaction mixture is purified by RP-HPLC (ACN/water+TFA).

Yield: 12.1 mg (32%) ESI-MS: m/z=426 [M+H]⁺ R$_f$(HPLC): 0.64 min (method 12)

Example 45

6-{1-[2,5-Difluoro-4-(4-fluorophenoxy)benzoyl]piperidin-4-yl}pyridazin-3-amine tert.-Butyl 4-(6-aminopyridazin-3-yl)-1,2,3,6-tetrahydropyridine-1-carboxylate

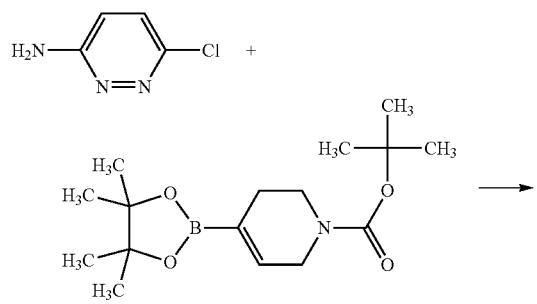

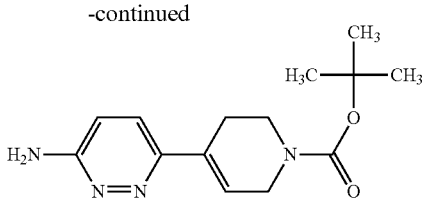

The reaction is performed under an argon-atmosphere. 6-Chloropyridazin-3-amine (5.20 g; 40.14 mmol), tert-butyl 4-(4,4,5,5-tetramethyl-1,3,2-dioxaborolan-2-yl)-1,2,3,6-tetrahydropyridine-1-carboxylate (13.65 g; 44.15 mmol) and sodium carbonate (2 mol/L; aq. solution; 80.28 mL; 160.56 mmol) in 1,4-dioxane (350 mL) is purged with argon. After 5 minutes Xphos 2$^{nd}$ generation catalyst (0.95 g; 1.20 mmol) is added and the reaction mixture is stirred overnight in a sealed vial at 100° C. The reaction mixture is filtered and concentrated under reduced pressure. The residue is taken up in MeOH, precipitated with water and filtered. The precipitate is dried in a drying oven at 50° C. The product is used without further purification.

Yield: quantitative ESI-MS: m/z=277 [M+H]⁺ R$_f$(HPLC): 0.78 min (method 2)

tert.-Butyl 4-(6-aminopyridazin-3-yl)-piperidine-1-carboxylate

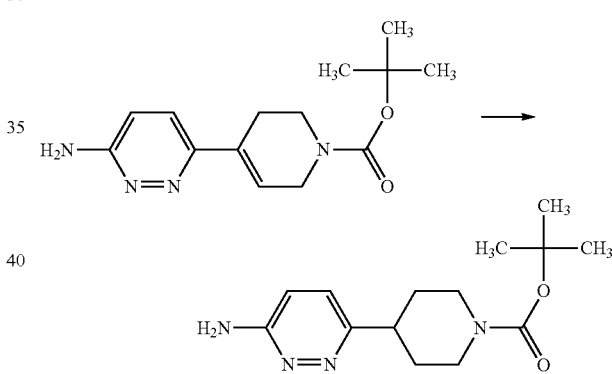

Under a hydrogen atmosphere (Parr-apparatus; 4 bar) tert.-butyl 4-(6-aminopyridazin-3-yl)-1,2,3,6-tetrahydropyridine-1-carboxylate (4.85 g; 17.55 mmol) and Pd/C (10%; 0.50 g) in MeOH (100 mL) are stirred at RT for 3 hours. After removal of the catalyst by filtration the mother liquid is concentrated under reduced pressure. The product is used without further purification.

Yield: quantitative ESI-MS: m/z=279 [M+H]⁺ R$_f$(HPLC): 0.86 (method 3)

6-(Piperidin-4-yl)pyridazin-3-amine dihydrochloride

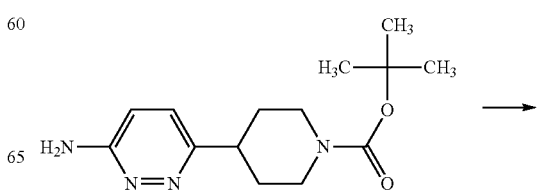

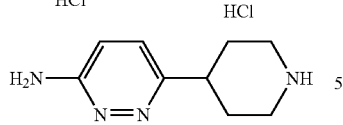

tert-Butyl 4-(6-aminopyridazin-3-yl)piperidine-1-carboxylate (100.0 mg; 0.36 mmol) and HCl (4 mol/L; solution in 1,4-dioxane; 1.00 mL; 4.00 mmol) in 1,2-dichloroethane (3 mL) are stirred at RT for 16 hours. The reaction mixture is concentrated under reduced pressure and used without further purification.

Yield: 82 mg (82%) ESI-MS: m/z=179 [M+H]$^+$ R$_t$(HPLC): 0.28 min (method 3)

6-{1-[2,5-Difluoro-4-(4-fluorophenoxy)benzoyl]piperidin-4-yl}pyridazin-3-amine

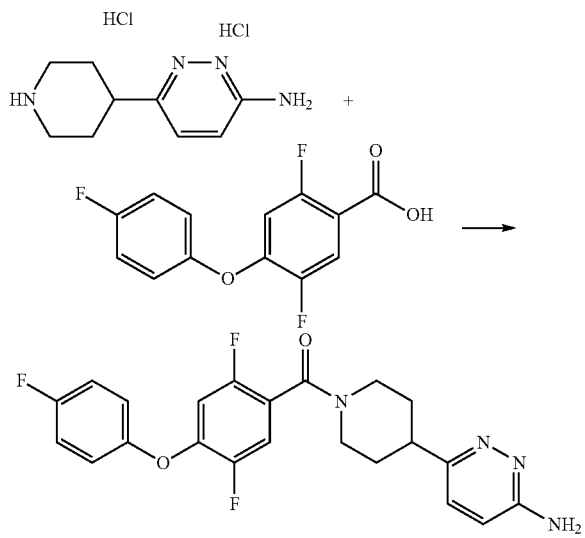

2,5-Difluoro-4-(4-fluorophenoxy)benzoic acid (32.2 mg; 0.12 mmol), HATU (45.6 mg; 0.12 mmol) and DIPEA (69.2 µL; 0.40 mmol) in DMF (2 mL) are stirred at RT for 5 minutes. 6-(Piperidin-4-yl)pyridazin-3-amine dihydrochloride (25.1 mg; 0.10 mmol) is added. After stirring for 1 hour at RT the reaction mixture is purified by RP-HPLC (ACN/water/NH$_4$OH).

Yield: 32.6 mg (76%) ESI-MS: m/z=429 [M+H]$^+$ R$_t$(HPLC): 0.72 min (method 6)

Example 46

6-{1-[2-Fluoro-4-(4-fluorophenoxy)benzoyl]piperidin-4-yl}pyridazin-3-amine

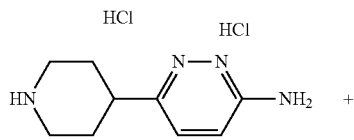

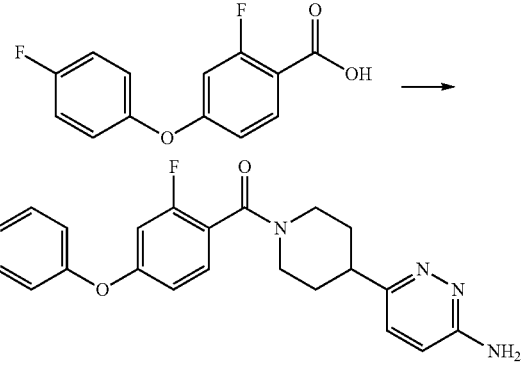

2-Fluoro-4-(4-fluorophenoxy)benzoic acid (30.2 mg; 0.12 mmol), HATU (45.6 mg; 0.12 mmol) and DIPEA (69.2 µL; 0.40 mmol) in DMF (2 mL) are stirred at RT for 5 minutes. 6-(Piperidin-4-yl)pyridazin-3-amine dihydrochloride (25.1 mg; 0.10 mmol) is added. After stirring for 1 hour at RT the reaction mixture is purified by RP-HPLC (ACN/water/NH$_4$OH).

Yield: 28.4 mg (64%) ESI-MS: m/z=411 [M+H]$^+$ R$_t$(HPLC): 0.70 min (method 6)

Example 47

6-{1-[2-Fluoro-4-(4-fluorophenoxy)-5-methoxybenzoyl]piperidin-4-yl}pyridazin-3-amine

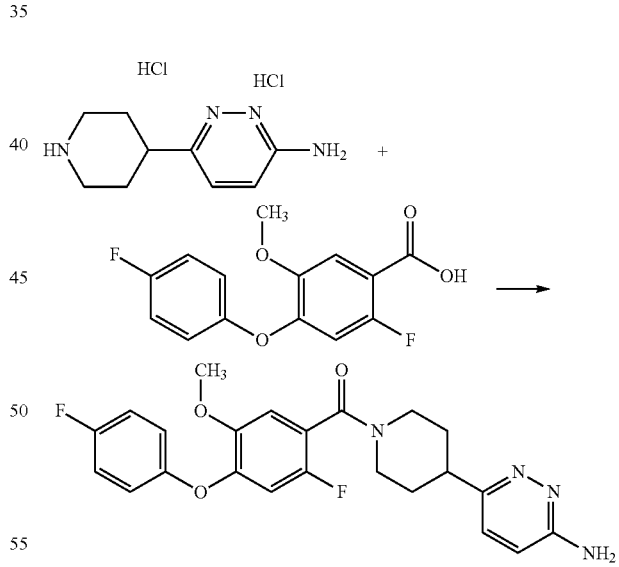

2-Fluoro-4-(4-fluorophenoxy)-5-methoxybenzoic acid (33.6 mg; 0.12 mmol), HATU (45.6 mg; 0.12 mmol) and DIPEA (69.2 µL; 0.40 mmol) in DMF (2 mL) are stirred at RT for 5 minutes. 6-(Piperidin-4-yl)pyridazin-3-amine dihydrochloride (25.1 mg; 0.10 mmol) is added. After stirring for 1 hour at RT the reaction mixture is purified by RP-HPLC (ACN/water/NH$_4$OH).

Yield: 35.0 mg (80%) ESI-MS: m/z=441 [M+H]$^+$ R$_t$(HPLC): 0.92 min (method 3)

Example 48

6-{1-[3-Fluoro-4-(4-fluorophenoxy)benzoyl]piperidin-4-yl}pyridazin-3-amine

3-Fluoro-4-(4-fluorophenoxy)benzoic Acid

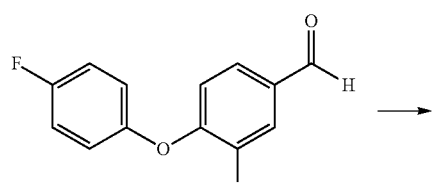

3-Fluoro-4-(4-fluorophenoxy)benzaldehyde (described in WO2013014185) (0.70 g; 3.00 mmol) and potassium permanganate (0.75 g; 4.75 mmol) in acetone (10 mL) and water (8 mL) are stirred at RT for 2 hours. NaOH (1 mol/L; aq. solution; 3 mL) is added and the reaction mixture is filtered through Celite® and washed with water. The organic solvent is evaporated and the aqueous layer is acidified using HCl (1 mol/L; aq. solution; 5 mL). The resulting precipitate is filtered, washed with water and dried.

Yield: 0.70 g (93%) ESI-MS: m/z=249 [M−H]⁻

6-{1-[3-Fluoro-4-(4-fluorophenoxy)benzoyl]piperidin-4-yl}pyridazin-3-amine trifluoroacetic Acid

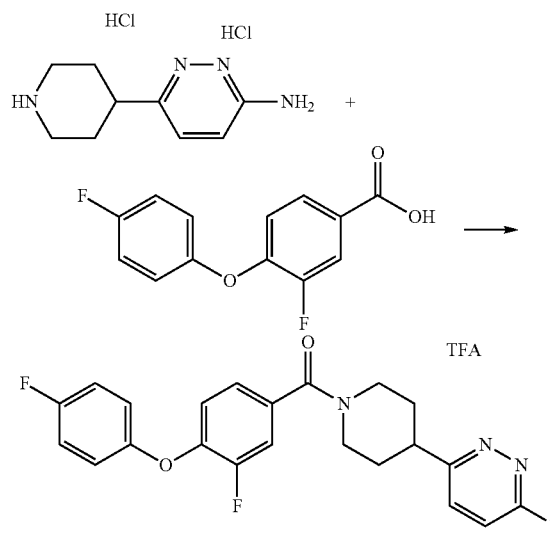

3-Fluoro-4-(4-fluorophenoxy)benzoic acid (30.0 mg; 0.12 mmol), 6-(Piperidin-4-yl)pyridazin-3-amine dihydrochloride (48.7 mg; 0.12 mmol)) and DIPEA (84.6 µL; 0.49 mmol) in DMF (2 mL) are stirred at RT. HATU (45.6 mg; 0.12 mmol) is added. After stirring over night at RT the reaction mixture is purified by RP-HPLC (ACN/water+TFA).

Yield: 40.2 mg (64%) ESI-MS: m/z=411 [M+H]⁺ R$_f$(HPLC): 0.62 min (method 11)

Example 49

6-{1-[4-Phenoxy-3-(trifluoromethyl)benzoyl]piperidin-4-yl}pyridazin-3-amine

4-Phenoxy-3-(trifluoromethyl)benzoic Acid

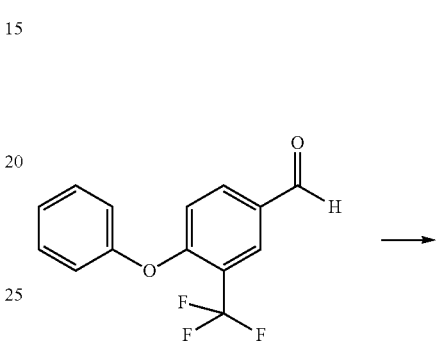

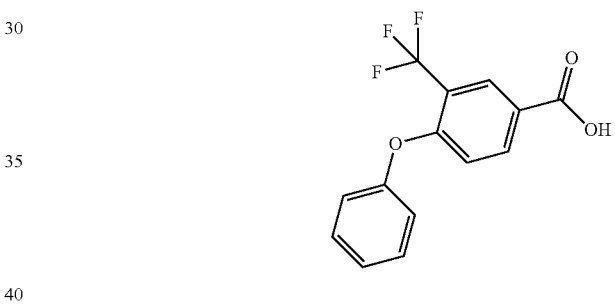

4-Phenoxy-3-(trifluoromethyl)benzaldehyde (synthesis according to WO2007129745) (0.67 g; 2.51 mmol) and potassium permanganate (0.70 g; 4.43 mmol) in acetone (10 mL) and water (8 mL) are stirred at RT for 2 hours. NaOH (1 mol/L; aq. solution; 3 mL) is added and the reaction mixture is filtered through Celite® and washed with water. The organic solvent is evaporated and the aqueous layer is acidified using HCl (1 mol/L; aq. solution; 5 mL). The resulting precipitate is filtered, washed with water and dried.

Yield: 0.58 g (81%) ESI-MS: m/z=281 [M−H]⁻

6-(Piperidin-4-yl)pyridazin-3-amine bis(trifluoroacetic Acid)

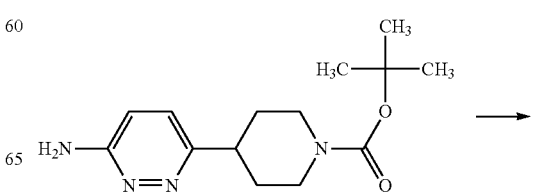

87
-continued

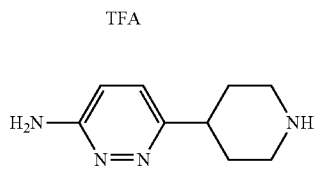

tert.-Butyl 4-(6-aminopyridazin-3-yl)-piperidine-1-carboxylate (9.10 g; 32.69 mmol) and TFA (25.19 mL; 326.93 mmol) in DCM (200 mL) are stirred at RT over night. The reaction mixture is concentrated under reduced pressure. The residue is triturated in diethyl ether, filtered and dried in a drying oven at 50° C.

Yield: quantitative ESI-MS: m/z=179 [M+H]$^+$ R$_t$(HPLC): 0.28 min (method 3)

6-{1-[4-Phenoxy-3-(trifluoromethyl)benzoyl]piperidin-4-yl}pyridazin-3-amine trifluoroacetic Acid

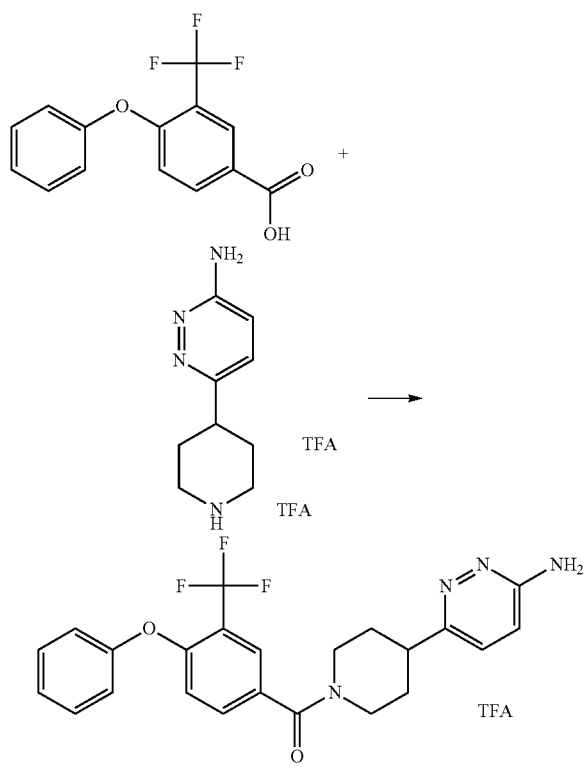

6-(Piperidin-4-yl)pyridazin-3-amine bis(trifluoroacetic acid) (43.2 mg; 0.11 mmol), 4-phenoxy-3-(trifluoromethyl)benzoic acid (30.0 mg; 0.11 mmol) and DIPEA (75.0 µL; 0.44 mmol) in DMF (2 mL) are stirred at RT. HATU (40.4 mg; 0.11 mmol) is added. The reaction mixture is stirred at RT until the reaction is completed. The reaction mixture is purified by RP-HPLC (ACN/water+TFA).

Yield: 34.4 mg (58%) ESI-MS: m/z=443 [M+H]$^+$ R$_t$(HPLC): 0.67 min (method 11)

88
Example 50

6-{1-[4-(4-Fluorophenoxy)benzoyl]piperidin-4-yl}-4-methylpyridazin-3-amine

6-Chloro-N-[(2,4-dimethoxyphenyl)methyl]-4-methylpyridazin-3-amine

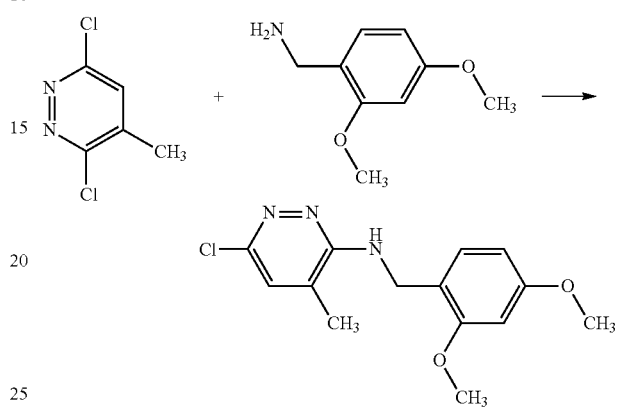

3,6-Dichloro-4-methylpyridazine (0.87 g; 5.34 mmol) and (2,4-dimethoxybenzylamine (0.88 mL; 5.87 mmol) in DIPEA (0.93 mL; 5.34 mmol) are stirred at 100° C. overnight. The reaction mixture is concentrated under reduced pressure and purified by silica gel chromatography (DCM/MeOH).

Yield: 0.53 g (34%) ESI-MS: m/z=294 and 296 [M+H]$^+$ R$_t$(HPLC): 0.84 min (method 1)

tert-Butyl 4-(6-{[(2,4-dimethoxyphenyl)methyl]amino}-5-methylpyridazin-3-yl)-1,2,3,6-tetrahydropyridine-1-carboxylate

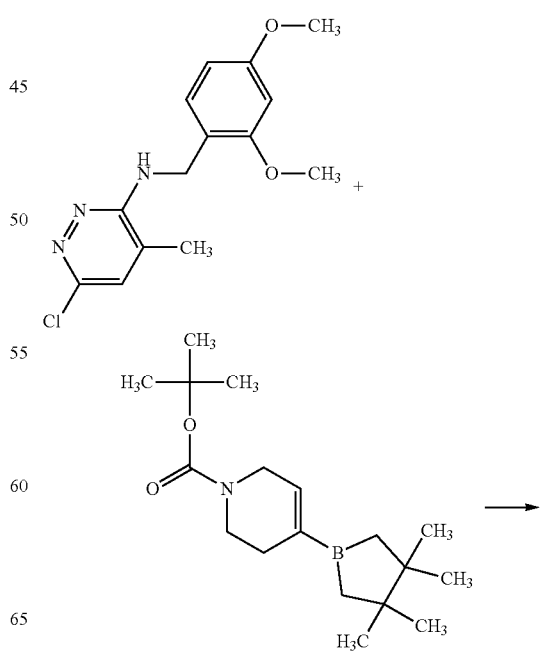

-continued

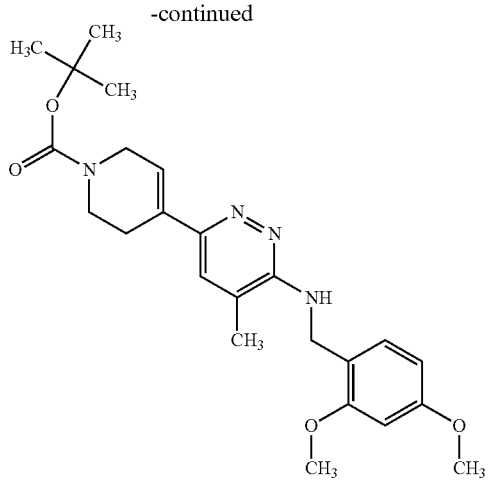

The reaction is performed under an argon atmosphere. 6-Chloro-N-[(2,4-dimethoxy-phenyl)-methyl]-4-methylpyridazin-3-amine (0.35 g; 1.19 mmol), tert-butyl 4-(3,3,4,4-tetramethyl-borolan-1-yl)-1,2,3,6-tetrahydropyridine-1-carboxylate (0.37 g; 1.19 mmol), Xphos 2$^{nd}$ generation catalyst (0.03 g; 0.04 mmol) and sodium carbonate (2 mol/L; aq. solution; 2.38 mL; 4.77 mmol) and 1,4-dioxane (10 mL) are stirred at 100° C. over night. The solvent is removed and the residue is taken up in DCM and washed with water. The organic layer is separated, dried over Na$_2$SO$_4$, filtered and concentrated under reduced pressure. The product is used without further purification.

Yield: 0.48 g (91%) ESI-MS: m/z=441 [M+H]$^+$
R$_t$(HPLC): 0.91 min (method 1)

tert-Butyl 4-(6-{[(2,4-dimethoxyphenyl)methyl]amino}-5-methylpyridazin-3-yl)piperidine-1-carboxylate

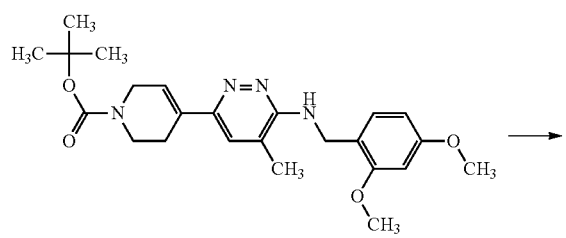

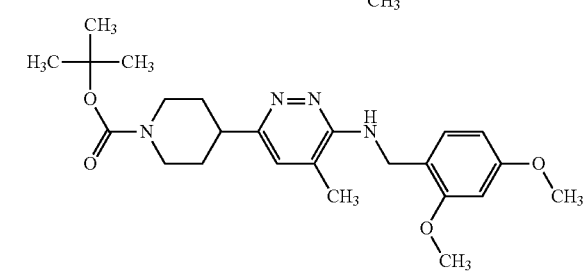

Under a hydrogen atmosphere (Parr-apparatus; 3 bar) tert-butyl 4-(6-{[(2,4-dimethoxy-phenyl)-methyl]amino}-5-methylpyridazin-3-yl)-1,2,3,6-tetrahydropyridine-1-carboxylate (0.48 g; 1.09 mmol) and Pd/C (10%; 0.05 g) in MeOH (20 mL) are stirred at RT for 16 hours. After removal of the catalyst by filtration the mother liquid is concentrated under reduced pressure. The product is used without further purification.

Yield: 0.48 g (quantitative) ESI-MS: m/z=443 [M+H]$^+$
R$_t$(HPLC): 0.90 min (method 1)

4-Methyl-6-(piperidin-4-yl)pyridazin-3-amine dihydrochloride

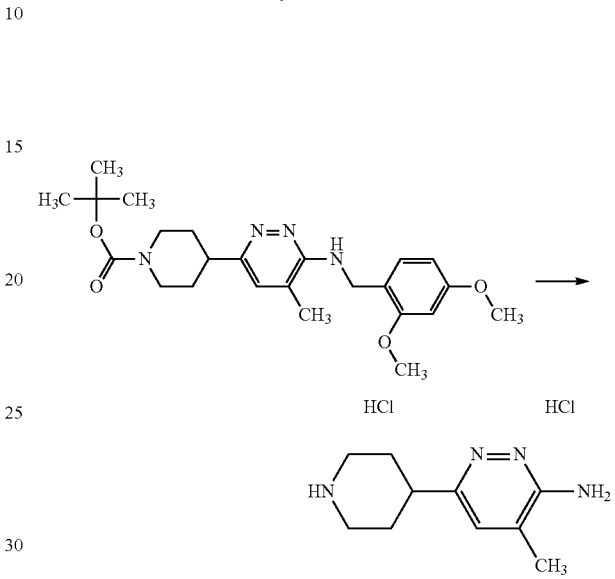

tert-Butyl 4-(6-{[(2,4-dimethoxyphenyl)methyl]amino}-5-methylpyridazin-3-yl)piperidine-1-carboxylate (0.42 g; 0.95 mmol) and TFA (30% solution in DCM; 5 mL) are stirred at RT for 3 hours. The reaction mixture is concentrated under reduced pressure and purified by RP-HPLC (ACN/water+TFA). The product containing fractions are concentrated under reduced pressure, the residue is taken up in HCl (1.5 mol/L; solution in MeOH) and again concentrated under reduced pressure. The product is used without further purification.

Yield: 0.25 g (99%) ESI-MS: m/z=193 [M+H]$^+$
R$_t$(HPLC): 0.12 min (method 1)

6-{1-[4-(4-Fluorophenoxy)benzoyl]piperidin-4-yl}-4-methylpyridazin-3-amine trifluoroacetic Acid

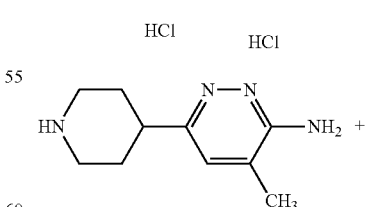

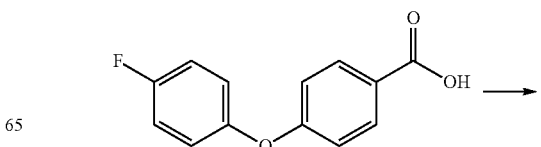

91

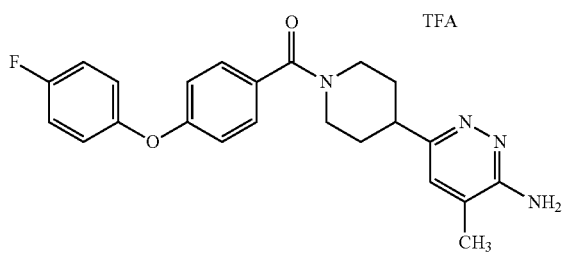

4-(4-Fluorophenoxy)benzoic acid (35.0 mg; 0.15 mmol), 4-methyl-6-(piperidin-4-yl)pyridazin-3-amine dihydrochloride (40.0 mg; 0.15 mmol) and DIPEA (103.3 μL; 0.60 mmol) in DMF (3 mL) are stirred at RT. HATU (63.1 mg; 0.17 mmol) is added. After stirring at RT over night the reaction mixture is purified by RP-HPLC (ACN/water+ TFA).

Yield: 20.0 mg (26%) ESI-MS: m/z=407 [M+H]$^+$
$R_t$(HPLC): 0.86 min (method 1)

Example 51

6-{1-[2-Fluoro-4-(4-fluorophenoxy)-5-methoxybenzoyl]piperidin-4-yl}-5-methylpyridazin-3-amine tert-Butyl 4-(6-amino-4-methylpyridazin-3-yl)-1,2,3,6-tetrahydropyridine-1-carboxylate

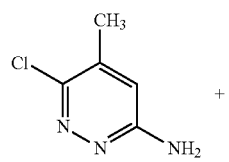

+

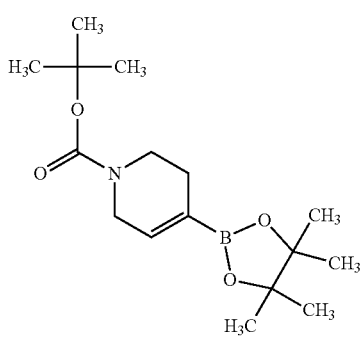

92

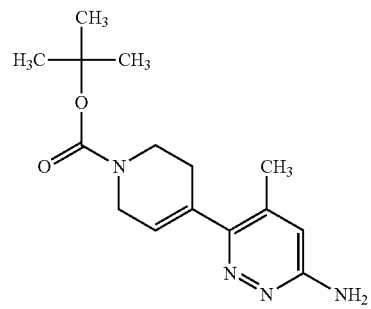

The reaction is performed under an argon atmosphere. 6-Chloro-5-methylpyridazin-3-amine (3.00 g; 20.90 mmol), tert-butyl 4-(4,4,5,5-tetramethyl-1,3,2-dioxaborolan-2-yl)-1,2,3,6-tetrahydropyridine-1-carboxylate (7.11 g; 22.98 mmol) and sodium carbonate (2 mol/L; aq. solution; 41.79 mL; 83.58 mmol) in 1,4-dioxane (150 mL) are purged with argon. Xphos 2$^{nd}$ generation catalyst (0.49 g; 0.63 mmol) is added and the reaction mixture is stirred at 100° C. overnight. The reaction mixture is concentrated under reduced pressure. The residue is taken up in water and extracted several times with EtOAc. The combined organic layers are washed with brine, dried over Na$_2$SO$_4$, filtered and concentrated under reduced pressure. The residue is purified by silica gel chromatography (DCM/MeOH).

Yield: 5.20 g (86%) ESI-MS: m/z=291 [M+H]$^+$
$R_t$(HPLC): 0.79 min (method 2)

tert-Butyl 4-(6-amino-4-methylpyridazin-3-yl)piperidine-1-carboxylate

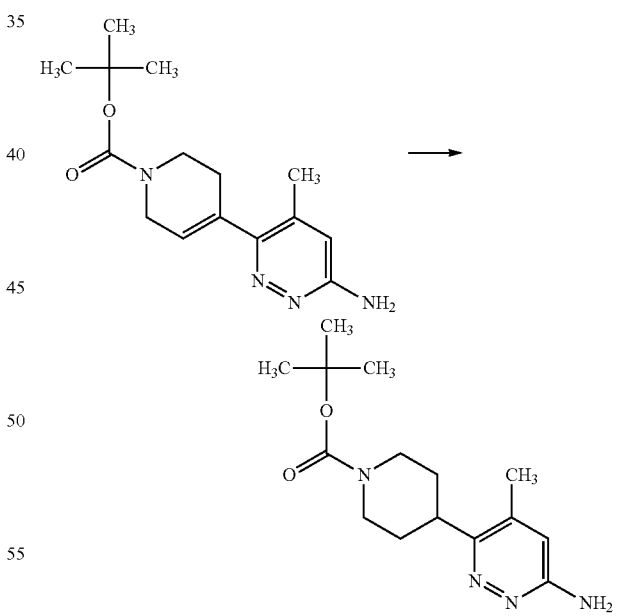

Under a hydrogen atmosphere (Parr-apparatus; 50 psi) tert-butyl 4-(6-amino-4-methylpyridazin-3-yl)-1,2,3,6-tetrahydropyridine-1-carboxylate (5.20 g; 17.91 mmol) and Pd/C (10%; 0.75 g) in MeOH (100 mL) are stirred at RT for 17 hours. After removal of the catalyst by filtration the mother liquid is concentrated under reduced pressure. The product is used without further purification.

Yield: 5.00 g (96%) ESI-MS: m/z=293 [M+H]$^+$
$R_t$(HPLC): 0.79 min (method 2)

5-Methyl-6-(piperidin-4-yl)pyridazin-3-amine bis (trifluoroacetic Acid)

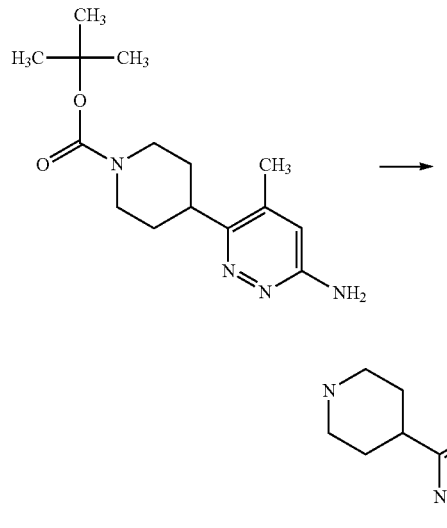

tert-Butyl 4-(6-amino-4-methylpyridazin-3-yl)piperidine-1-carboxylate (5.00 g; 17.10 mmol) and TFA (13.19 mL; 171.01 mmol) in DCM (100 mL) are stirred at RT over night. The reaction mixture is concentrated under reduced pressure. The residue is triturated in diethyl ether, filtered and dried in a drying oven at 50° C.

Yield: 7.20 g (quantitative) ESI-MS: m/z=193 [M+H]$^+$

6-{1-[2-Fluoro-4-(4-fluorophenoxy)-5-methoxybenzoyl]piperidin-4-yl}-5-methylpyridazin-3-amine

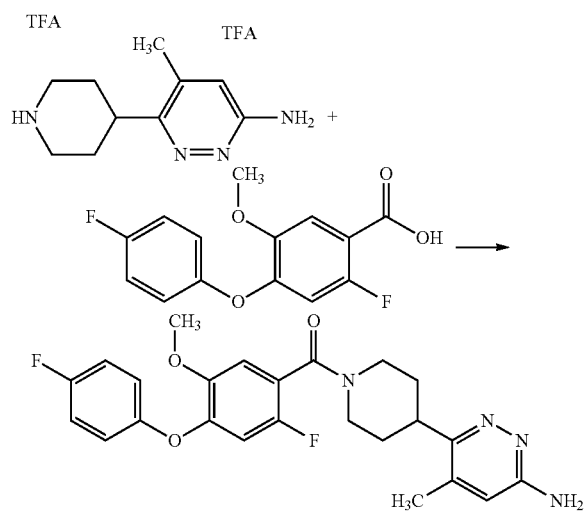

2-Fluoro-4-(4-fluorophenoxy)-5-methoxybenzoic acid (33.6 mg; 0.12 mmol), HATU (45.6 mg; 0.12 mmol) and DIPEA (69.2 µL; 0.40 mmol) in DMF (2 mL) are stirred at RT for 5 minutes. 5-Methyl-6-(piperidin-4-yl)pyridazin-3-amine bis(trifluoroacetic acid) (42.0 mg; 0.10 mmol) is added. After stirring for 1 hour at RT the reaction mixture is purified by RP-HPLC (ACN/water/NH$_4$OH).

Yield: 25.0 mg (55%) ESI-MS: m/z=455 [M+H]$^+$
R$_t$(HPLC): 0.95 min (method 3)

Example 52

[(2S)-4-(6-Aminopyridazin-3-yl)-1-[2,5-difluoro-4-(4-fluorophenoxy)benzoyl]piperidin-2-yl]methanol

(8aS)-7-(6-Aminopyridazin-3-yl)-hexahydro-1H-[1,3]oxazolo[3,4-a]pyridin-3-one

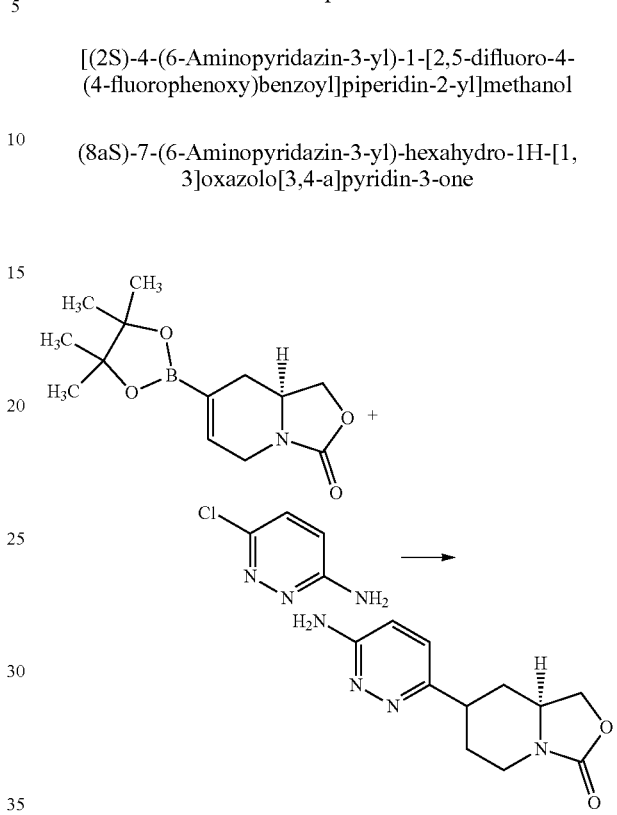

Step 1:

The reaction is performed under an argon-atmosphere. 6-Chloropyridazin-3-amine (0.49 g; 3.77 mmol), (8aS)-7-(4,4,5,5-tetramethyl-1,3,2-dioxaborolan-2-yl)-1H,3H,5H,8H,8aH-[1,3]oxazolo[3,4-a]pyridin-3-one (1.00 g; 3.77 mmol) (synthesized analog to (8aR)-7-(4,4,5,5-tetramethyl-1,3,2-dioxaborolan-2-yl)-1H,3H,5H,8H,8aH-[1,3]oxazolo[3,4-a]pyridin-3-one as described in US20150218165), Xphos 2$^{nd}$ generation catalyst (0.09 g; 0.11 mmol) and sodium carbonate (2 mol/L; aq. solution; 7.54 mL; 15.09 mmol) in 1,4-dioxane (20 mL) is stirred over night at 100° C. The reaction mixture is diluted with water and extracted several times with DCM. The combined organic layers are dried, filtered and concentrated under reduced pressure. The residue is purified by silica gel chromatography (DCM/MeOH) and taken to the next step.

Yield: 0.71 g (81%) ESI-MS: m/z=233 [M+H]$^+$
R$_t$(HPLC): 0.51 min (method 3)

Step 2:

Under a hydrogen atmosphere (Parr-apparatus; 50 psi) the product from the previous step 1 (0.71 g; 3.04 mmol), Pd/C (10%; 0.07 g) and acetic acid (1.00 mL; 17.15 mmol) in THF (14 mL) are stirred at 50° C. for 2 days. Additional catalyst is added and further hydrogenated. After removal of the catalyst by filtration the mother liquid is evaporated under reduced pressure. The residue is used without further purification.

Yield: 0.71 g (quantitative) ESI-MS: m/z=235 [M+H]$^+$
R$_t$(HPLC): 0.28 min (method 3)

95

[(2S)-4-(6-Aminopyridazin-3-yl)piperidin-2-yl]
methanol

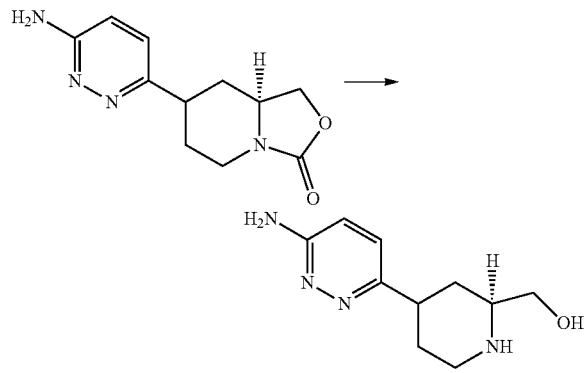

(8aS)-7-(6-Aminopyridazin-3-yl)-hexahydro-1H-[1,3]
oxazolo[3,4-a]pyridin-3-one (0.71 g; 3.04 mmol) and
barium hydroxide (3.13 g; 18.24 mmol) in water (16 mL)
and 1,4-dioxane (25 mL) are stirred at reflux for 4 hours. The
reaction mixture is concentrated under reduced pressure and
the residue is taken up in MeOH. The insoluble material is
filtered and discarded. The mother liquid is concentrated
under reduced pressure. The residue is taken up in MeOH/
DCM, the insoluble material is filtered and discarded and the
mother liquid is concentrated under reduced pressure. The
residue is used without further purification.

Yield: quantitative ESI-MS: m/z=209 [M+H]$^+$ R$_f$(HPLC):
0.19 min (method 3)

[(2S,4S)-4-(6-Aminopyridazin-3-yl)-1-[2,5-difluoro-
4-(4-fluorophenoxy)benzoyl]piperidin-2-yl]methanol
(Example 52a) and [(2S,4R)-4-(6-Aminopyridazin-
3-yl)-1-[2,5-difluoro-4-(4-fluorophenoxy)benzoyl]
piperidin-2-yl]methanol (Example 52b)

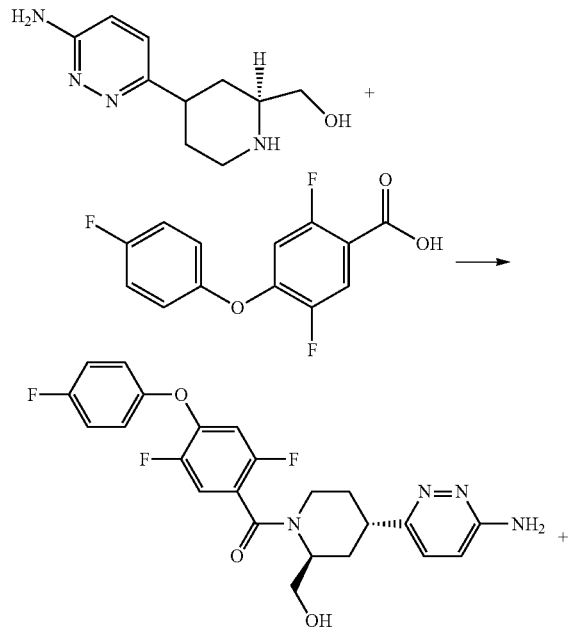

96

-continued

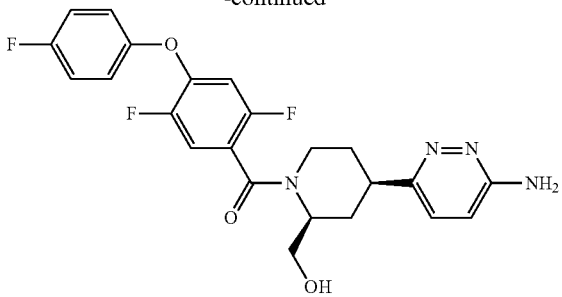

[(2S)-4-(6-Aminopyridazin-3-yl)piperidin-2-yl]methanol
(60.0 mg; 0.29 mmol) and 2,5-difluoro-4-(4-fluorophenoxy)
benzoic acid (77.3 mg; 0.29 mmol) and DIPEA (203.2 µL;
1.18 mmol) in DMF (4 mL) are stirred at RT. HATU (109.5
mg; 0.29 mmol) is added. After stirring over night at RT the
reaction mixture is purified by RP-HPLC (ACN/water/
NH$_4$OH) to provide a mixture of diastereomers. The diastereomers are separated by chiral RP-HPLC (Chiral Art®
Amylose SA; scCO$_2$/IPA with NH$_3$; 40° C.). The relative
stereochemistry is determined by NMR.

Yield (Example 52a): 5.0 mg (4%) ESI-MS: m/z=459
[M+H]$^+$ R$_f$(HPLC): 3.14 min (method SFC1)

Yield (Example 52b): 30.0 mg (23%) ESI-MS: m/z=459
[M+H]$^+$ R$_f$(HPLC): 4.22 min (method SFC1)

Example 53

5-(1-{2-Fluoro-4-[(1,2-oxazol-3-yl)methoxy]
benzoyl}piperidin-4-yl)-4-methoxypyridin-2-amine
trifluoroacetic Acid

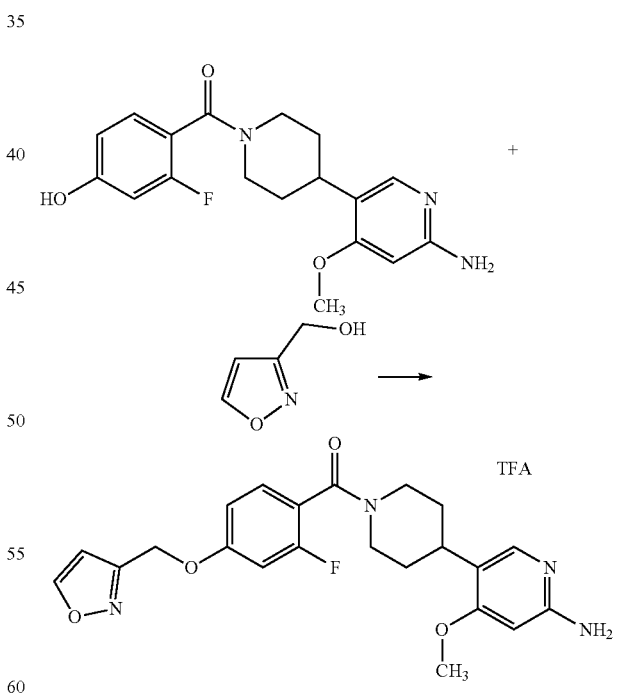

4-[4-(6-Amino-4-methoxypyridin-3-yl)piperidine-1-carbonyl]-3-fluorophenol (25.0 mg; 0.07 mmol), (1,2-oxazol-
3-yl)methanol (6.8 mg; 0.17 mmol), TPP (50.0 mg; 0.19
mmol) and DTAD (40.0 mg; 0.17 mmol) in 1,4-dioxane (3
mL) are stirred for 1 hour at 60° C. The reaction mixture is
purified by RP-HPLC (ACN/water+TFA).

Yield: 20.0 mg (39%) ESI-MS: m/z=427 [M+H]⁺
R_t(HPLC): 0.52 min (method 11)

Example 54

5-(1-{2-Fluoro-4-[(1,3-thiazol-2-yl)methoxy]benzoyl}piperidin-4-yl)-4-methoxypyridin-2-amine trifluoroacetic Acid

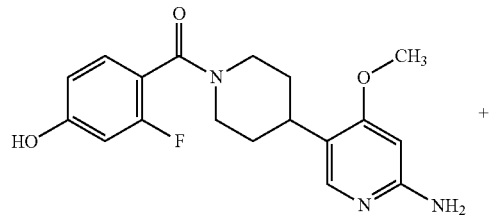

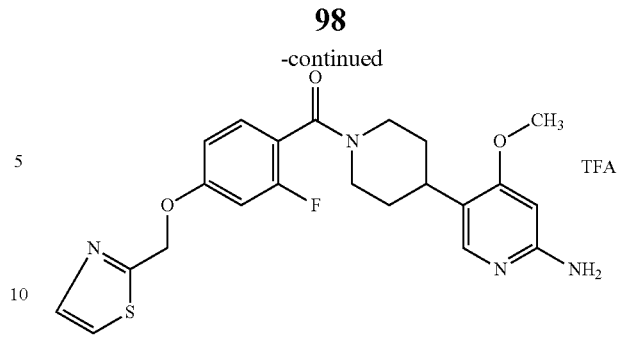

4-[4-(6-Amino-4-methoxypyridin-3-yl)piperidine-1-carbonyl]-3-fluorophenol (25.0 mg; 0.07 mmol), (1,3-thiazol-2-yl)methanol (19.6 mg; 0.17 mmol), TPP (50.0 mg; 0.19 mmol) and DTAD (40.0 mg; 0.17 mmol) in 1,4-dioxane (3 mL) are stirred for 1 hour at 60° C. The reaction mixture is purified by RP-HPLC (ACN/water+TFA).

Yield: 31.1 mg (77%) ESI-MS: m/z=443 [M+H]⁺
R_t(HPLC): 0.53 min (method 11)

ANALYTICAL DATA

The reported mass spectrometry (MS) data (Table 3) is for observed mass (e.g., [M+H]⁺). HPLC method used to characterize the compounds of the invention is described in Table 2. HPLC methods A, 1-3, 6, 8, 11 and 12 are described below. (HPLC methods 4, 5, 7, 9 and 10 are intentionally omitted.)

TABLE 2

| | | | HPLC Method | | | | |
|---|---|---|---|---|---|---|---|
| | Mobile | Mobile | Gradient | | | Flow | |
| Method | Phase A | Phase B | Time (min) | % A | % B | (mL/min.) | Column |
| A | 0.1% Formic Acid in Water | 0.1% Formic Acid in | 0 | 95.0 | 5.0 | 0.8 | BEH 2.5 × 50 mm C18, 1.7 μm particle diameter |
| | | | 1.0 | 5.0 | 95.0 | | |
| | | | 1.3 | 5.0 | 95.0 | | |
| | | | 1.4 | 95.0 | 5.0 | | |
| | | | 1.7 | 95.0 | 5.0 | | |

| Method Name: | 1 |
|---|---|
| Device description: | Agilent 1200 with DA- and MS-Detector |
| Column: | Sunfire C18_3.0 × 30 mm_2.5 μm |
| Column producer: | Waters |

| Gradient/Solvent Time [min] | % Sol [Water 0.1% TFA (v/v)] | % Sol [Acetonitrile] | Flow [ml/min] | Temp [° C.] |
|---|---|---|---|---|
| 0.0 | 97.0 | 3.0 | 2.2 | 60.0 |
| 0.2 | 97.0 | 3.0 | 2.2 | 60.0 |
| 1.2 | 0.0 | 100.0 | 2.2 | 60.0 |
| 1.25 | 0.0 | 100.0 | 3.0 | 60.0 |
| 1.4 | 0.0 | 100.0 | 3.0 | 60.0 |

| Method Name: | 2 |
|---|---|
| Device description: | Agilent 1200 with DA- and MS-Detector |
| Column: | Zorbax StableBond C18_3.0 × 30 mm_1.8 μm |
| Column producer: | Agilent |

| Gradient/Solvent Time [min] | % Sol [Water 0.1% TFA (v/v)] | % Sol [Acetonitrile] | Flow [ml/min] | Temp [° C.] |
|---|---|---|---|---|
| 0.0 | 97.0 | 3.0 | 2.2 | 60.0 |
| 0.2 | 97.0 | 3.0 | 2.2 | 60.0 |
| 1.2 | 0.0 | 100.0 | 2.2 | 60.0 |

TABLE 2-continued

HPLC Method

| | | | | |
|---|---|---|---|---|
| 1.25 | 0.0 | 100.0 | 3.0 | 60.0 |
| 1.4 | 0.0 | 100.0 | 3.0 | 60.0 |

Method Name: 3
Device description: Agilent 1200 with DA- and MS-Detector
Column: XBridge C18_3.0 × 30 mm_2.5 μm
Column producer: Waters

| Gradient/Solvent Time [min] | % Sol [Water 0.1% NH$_3$] | % Sol [Acetonitrile] | Flow [ml/min] | Temp [° C.] |
|---|---|---|---|---|
| 0.0 | 97.0 | 3.0 | 2.2 | 60.0 |
| 0.2 | 97.0 | 3.0 | 2.2 | 60.0 |
| 1.2 | 0.0 | 100.0 | 2.2 | 60.0 |
| 1.25 | 0.0 | 100.0 | 3.0 | 60.0 |
| 1.4 | 0.0 | 100.0 | 3.0 | 60.0 |

Method Name: 4
Column: BEH 2.5 × 50 mm C18, 1.7 μm particle diameter
Column producer: Waters

| Gradient/Solvent Time [min] | 0.1% Formic Acid in Water | 0.1% Formic Acid in ACN | Flow [ml/min] | |
|---|---|---|---|---|
| 0 | 95.0 | 5.0 | 0.8 | |
| 1.0 | 5.0 | 95.0 | 0.8 | |
| 1.3 | 5.0 | 95.0 | 0.8 | |
| 1.4 | 95.0 | 5.0 | 0.8 | |
| 1.7 | 95.0 | 5.0 | 0.8 | |

Method Name: 5
Device description: Waters Acquity, QDa Detector
Column: Sunfire C18_3.0 × 30 mm_2.5 μm
Column producer: Waters

| Gradient/Solvent Time [min] | % Sol [Water 0.1% TFA (v/v)] | % Sol [Acetonitrile 0.08% TFA (v/v)] | Flow [ml/min] | Temp [° C.] |
|---|---|---|---|---|
| 0.0 | 95.0 | 5.0 | 1.5 | 60.0 |
| 1.3 | 0.0 | 100.0 | 1.5 | 60.0 |
| 1.5 | 0.0 | 100.0 | 1.5 | 60.0 |
| 1.6 | 95.0 | 5.0 | 1.5 | 60.0 |

Method Name: 6
Device description: Waters Acquity, QDa Detector
Column: XBridge C18_3.0 × 30 mm_2.5 μm
Column producer: Waters

| Gradient/Solvent Time [min] | % Sol [Water 0.1% NH$_3$] | % Sol [Acetonitrile] | Flow [ml/min] | Temp [° C.] |
|---|---|---|---|---|
| 0.0 | 95.0 | 5.0 | 1.5 | 60.0 |
| 1.3 | 0.0 | 100.0 | 1.5 | 60.0 |
| 1.5 | 0.0 | 100.0 | 1.5 | 60.0 |
| 1.6 | 95.0 | 5.0 | 1.5 | 60.0 |

Method Name: 7
Device description: Agilent 1100 with DA- and MS-Detector
Column: Zorbax StableBond C18_4.6 × 30 mm_3.5 μm
Column producer: Agilent

| Gradient/Solvent Time [min] | % Sol [Water 0.1% TFA (v/v)] | % Sol [Acetonitrile] | Flow [ml/min] | Temp [° C.] |
|---|---|---|---|---|
| 0.0 | 95.0 | 5.0 | 4.0 | 60.0 |
| 0.15 | 95.0 | 5.0 | 4.0 | 60.0 |
| 1.7 | 0.0 | 100.0 | 4.0 | 60.0 |
| 2.25 | 0.0 | 100.0 | 4.0 | 60.0 |

Method Name: 8
Device description: Waters Acquity, QDa Detector
Column: XBridge C18_3.0 × 30 mm_2.5 μm
Column producer: Waters TABLE 2-continued

| HPLC Method | | | | |
|---|---|---|---|---|
| Gradient/Solvent Time [min] | % Sol [Water 0.1% NH$_3$] | % Sol [Acetonitrile] | Flow [ml/min] | Temp [° C.] |
| 0.0 | 95.0 | 5.0 | 1.5 | 60.0 |
| 1.3 | 0.0 | 100.0 | 1.5 | 60.0 |
| 1.5 | 0.0 | 100.0 | 1.5 | 60.0 |
| 1.6 | 95.0 | 5.0 | 1.5 | 60.0 |

| Method Name: | 9 |
|---|---|
| Device description: | Waters Acquity with DA- and MS-Detector |
| Column: | XBridge BEH C18_2.1 × 30 mm_1.7 μm |
| Column producer: | Waters |

| Gradient/Solvent Time [min] | % Sol [Water 0.1% TFA (v/v)] | % Sol [Acetonitrile] | Flow [ml/min] | Temp [° C.] |
|---|---|---|---|---|
| 0.0 | 99.0 | 1.0 | 1.6 | 60.0 |
| 0.02 | 99.0 | 1.0 | 1.6 | 60.0 |
| 1.0 | 0.0 | 100.0 | 1.6 | 60.0 |
| 1.1 | 0.0 | 100.0 | 1.6 | 60.0 |

| Method Name: | 10 |
|---|---|
| Device description: | Waters Acquity, QDa Detector |
| Column: | XBridge C18_3.0 × 30 mm_2.5 μm |
| Column producer: | Waters |

| Gradient/Solvent Time [min] | % Sol [Water 0.1% NH$_3$] | % Sol [Acetonitrile] | Flow [ml/min] | Temp [° C.] |
|---|---|---|---|---|
| 0.0 | 95.0 | 5.0 | 1.5 | 60.0 |
| 1.3 | 0.0 | 100.0 | 1.5 | 60.0 |
| 1.5 | 0.0 | 100.0 | 1.5 | 60.0 |
| 1.6 | 95.0 | 5.0 | 1.5 | 60.0 |

| Method Name: | 11 |
|---|---|
| Device description: | Waters Acquity, QDa Detector |
| Column: | Sunfire C18_3.0 × 30 mm_2.5 μm |
| Column producer: | Waters |

| Gradient/Solvent Time [min] | % Sol [Water 0.1% TFA (v/v)] | % Sol [Acetonitrile 0.08% TFA (v/v)] | Flow [ml/min] | Temp [° C.] |
|---|---|---|---|---|
| 0.0 | 95.0 | 5.0 | 1.5 | 60.0 |
| 1.3 | 0.0 | 100.0 | 1.5 | 60.0 |
| 1.5 | 0.0 | 100.0 | 1.5 | 60.0 |
| 1.6 | 95.0 | 5.0 | 1.5 | 60.0 |

| Method Name: | 12 |
|---|---|
| Device description: | Waters Acquity, QDa Detector |
| Column: | Sunfire C18_3.0 × 30 mm_2.5 μm |
| Column producer: | Waters |

| Gradient/Solvent Time [min] | % Sol [Water 0.1% TFA (v/v)] | % Sol [Acetonitrile 0.08% TFA (v/v)] | Flow [ml/min] | Temp [° C.] |
|---|---|---|---|---|
| 0.0 | 95.0 | 5.0 | 1.5 | 60.0 |
| 1.3 | 0.0 | 100.0 | 1.5 | 60.0 |
| 1.5 | 0.0 | 100.0 | 1.5 | 60.0 |
| 1.6 | 95.0 | 5.0 | 1.5 | 60.0 |

| Method Name: | SFC1 |
|---|---|
| Device description: | Agilent 1260 SFC with DAD and MS |
| Column: | CHIRAL ART ® Amylose SA_4.6 × 250 mm_5 μm |
| Column producer: | YMC |

| Gradient/Solvent Time [min] | % Sol [scCO2] | % Sol [IPA 20 mM NH$_3$] | Flow [ml/min] | Temp [° C.] | Back pressure [PSI] |
|---|---|---|---|---|---|
| 0.0 | 70.0 | 30.0 | 4.0 | 40.0 | 2175.0 |
| 10.0 | 70.0 | 30.0 | 4.0 | 40.0 | 2175.0 |

Observed mass and retention times (Method A) for compounds 1-26 are shown in Table 3.

TABLE 3

Analytical Data

| Compound No. | Observed Mass (m/z) [M + H]$^+$ | R.T. (min) |
|---|---|---|
| 1 | 374.3 | 0.64 |
| 2 | 443.3 | 0.71 |
| 3 | 375.4 | 0.62 |
| 4 | 459.3 | 0.73 |
| 5 | 389.4 | 0.66 |
| 6 | 416.4 | 0.70 |
| 7 | 401.4 | 0.56 |
| 8 | 420.4 | 0.58 |
| 9 | 405.3 | 0.61 |
| 10 | 393.3 | 0.62 |
| 11 | 410.3 | 0.68 |
| 12 | 415.3 | 0.70 |
| 13 | 409.2 | 0.68 |
| 14 | 403.3 | 0.72 |
| 15 | 375.3 | 0.59 |
| 16 | 417.3 | 0.56 |
| 17 | 417.3 | 0.75 |
| 18 | 418.4 | 0.74 |
| 19 | 443.3 | 0.72 |
| 20 | 404.3 | 0.71 |
| 21 | 460.2 | 0.72 |
| 22 | 462.3 | 0.74 |
| 23 | 403.3 | 0.70 |
| 24 | 376.2 | 0.60 |
| 25 | 447.4 | 0.50 |
| 26 | 444.2 | 0.72 |

ASSESSMENT OF BIOLOGICAL ACTIVITY

High Throughput Screening Assay

This screening assay measures TRPC6 (transient receptor potential cation channel, subfamily C, member 6) ion channel activation via addition either of the commercially available DAG ligand analogue OAG (1-oleoyl-2-acetyl-sn-glycerol) or of the TRPC6 agonist 1-[1-(4,5,6,7,8-pentahydrocyclohepta[2,1-d]thiophen-2-ylcarbonyl)-4-piperidyl]-3-hydrobenzimidazol-2-one (GSK1702934A). The assay utilizes a FLIPR membrane potential (FMP) dye from Molecular Devices, which is a voltage sensitive indicator with a fluorescent quencher. Changes in membrane potential as measured by the fluorescent signal increase during membrane depolarization provide a measurement of channel activity.

High Throughput Screening Assay Method 1:

The commercially available HEK293 cell line expressing human TRPC6 channel (Axxam/PerkinElmer) is scaled up in bulk and frozen in liquid nitrogen. Frozen cell stocks are thawed and re-suspended in culture media as recommended by the manufacturer supplemented with 0.5 mg/ml of geneticin to promote retention of the TRPC6 construct. Cells are plated at a density of 15,000 cells/well in Greiner 384 well poly-D-lysine coated black clear bottom plates, and incubated for 18-20 h at 37° C. and 5% $CO_2$. To initiate the assay, the growth media is removed using a plate washer and 25 ul of a FMP dye mix is added to each well. The 4× stock FMP dye from the manufacturer is diluted 1× with assay buffer (low calcium Tyrode's assay buffer: 130 mM NaCl, 5 mM KCl, 0.15 mM $CaCl_2$), 1 mM $MgCl_2$, 5 mM $NaHCO_3$, 20 mM HEPES pH 7.4) containing 36 μM BAPTA/AM. The cells are incubated at room temperature (19-22° C.) for 30 minutes. For the screening assay, 5 uL of diluted compound stock is added to each well and incubated for 15 minutes at room temperature (19-22° C.). Using the Hamamatsu FDSS6000 or FDSS7000, 10 uL of the synthetic, membrane permeant analog of 1,2 diacylglycerol (DAG), 1-oleoyl-2-acetoyl-n-glycerol (OAG), is added and fluorescent readings taken every second from 50 seconds to 3 minutes. This results in a final concentration of 3 ug/ml for the test compound, 60 μM for OAG and 3% for DMSO. Controls and blanks consisted of HEK293 TRPC6 cells that are exposed to OAG. A reference inhibitor added along with the test compound is included as part of the blanks. This inhibitor suppresses the TRPC6 channel activation. These controls set the screening window, and "hits" are defined as those compounds inhibiting the membrane depolarization caused by OAG by at least 50%. $IC_{50}$ values are determined for compounds that meet these criteria by titrating compound stock at a final starting concentration of 30 μM using a 3-fold serial dilution for 11 points. Curves are generated by fitting each data set to a four-parameter logistic equation using nonlinear regression.

High Throughput Screening Assay Method 2:

The commercially available HEK293 cell line (ATCC) was stably transfected with an human TRPC6 gene construct in pcDNA3.1(+) (Thermo Fisher) and screened to find a clone with TRPC6 expression. These cells were maintained in growth medium recommended by the manufacturer supplemented with 400 μg/ml G418 to promote retention of the TRPC6 construct. After growing to near confluency, cells were plated at a density of 15,000 cells/well in clear bottom black walled poly-D-Lys coated 384-well tissue culture treated plates (TwinHelix, cat. #GR 4332 CPL) in growth medium lacking G418, and allowed to grow for 24 hrs. Growth media was removed from the wells and cells were then loaded with 20 μL of 0.5× Membrane Potential sensitive dye (Molecular Devices) in the presence of 30 μM BAPTA-AM (Invitrogen) in Tyrode's assay buffer (130 mM NaCl, 5 mM KCl, 0.15 mM $CaCl_2$), 1 mM $MgCl_2$, 5 mM $NaHCO_3$, 20 mM HEPES, pH 7.4) and incubated for 60 min at room temperature in the dark. Ten μL/well of test compound or controls was added to the wells with the FLIPR$^{TETRA}$ (Molecular Devices) and incubated for 5 minutes. Compounds were tested at eight concentrations (10, 3.16, 1, 0.316, 0.1, 0.0316, 0.01 and 0.00316 μM diluted in Tyrode's assay buffer and 0.5% DMSO, final concentration) with inter-plate duplicate data points. Subsequently, 15 μL/well of GSK1702934A agonist in Tyrode's assay buffer was added to a final concentration of 3 μM by the FLIPR$^{TETRA}$ and the signal of the emitted fluorescence (Excitation: 510-545 nm, Emission: 565-625 nm) was recorded for 3 minutes. Negative and positive controls were included on each plate. Negative controls wells consisted of cells exposed to Tyrode's assay buffer and agonist solution, but no test compound. Positive control consisted of cells exposed to 100 mM Verapamil hydrochloride (Tocris, cat. #0654) diluted in Tyrode's assay buffer and 0.5% DMSO final concentration and agonist solution. Inhibition was expressed as a percentage of control, with 0% activity being a result in which the response value of the test wells reached a level identical to the wells containing Verapamil plus GSK1702934A and 100% activity being a result in which the response value of the test wells reached a level identical to the wells containing GSK1702934A alone. Genedata Screener® 14.0.6 was used for data analysis to fit $IC_{50}$ curves.

TABLE 4

Antagonist effects of compounds of the invention against human TRPC6 (IC$_{50}$) using High Throughput Screening Assay Method 1

| Compound Number | Fluorescence TRPC6 IC$_{50}$ (nM) |
| --- | --- |
| 1 | 326 |
| 2 | 504 |
| 3 | 39 |
| 4 | 351 |
| 5 | 372 |
| 6 | 540 |
| 7 | 4670 |
| 8 | 1230 |
| 9 | 511 |
| 10 | 75 |
| 11 | 1040 |
| 12 | 400 |
| 13 | 266 |
| 14 | 324 |
| 15 | 422 |
| 16 | 2070 |
| 17 | 2195 |
| 18 | 1310 |
| 19 | 1326 |
| 20 | 1160 |
| 21 | 191 |
| 22 | 8875 |
| 23 | 432 |
| 24 | 199 |
| 25 | 8974 |
| 26 | 3753 |

TABLE 5

Antagonist effects of compounds of the invention against human TRPC6 (IC50) using High Throughput Screening Assay Method 2

| Compound No. | Fluorescence TRPC6 IC$_{50}$ (nM) |
| --- | --- |
| 27 | 97 |
| 28 | 135 |
| 29 | 158 |
| 30 | 166 |
| 31 | 205 |
| 32 | 97 |
| 33 | 250 |
| 34 | 428 |
| 35 | 154 |
| 36 | 135 |
| 37 | 478 |
| 38 | 791 |
| 39 | 662 |
| 40 | 482 |
| 41 | 2169 |
| 42 | 789 |
| 43 | 1806 |
| 44 | 199 |
| 45 | 61 |
| 46 | 57 |
| 47 | 34 |
| 48 | 141 |
| 49 | 1164 |
| 50 | 288 |
| 51 | 182 |
| 52a | — |
| 52b | 80 |
| 53 | 641 |
| 54 | 1189 |

METHODS OF THERAPEUTIC USE

The compounds disclosed herein effectively inhibit TRPC6 activity. The inhibition of TRPC6 is an attractive means for preventing and treating a variety of diseases or conditions that are exacerbated by TRPC6 activity. Thus, the compounds are useful for the treatment of diseases and conditions as described in the Background and Detailed Description section, including the following conditions and diseases:

cardiac conditions (e.g., cardiac hypertrophy), hypertension (e.g., primary or secondary), pulmonary arterial hypertension (e.g., IPAH), a neurodegenerative disease or disorder (e.g., Alzheimer's disease (AD), Parkinson's disease, Huntington's disease, amyotrophic lateral sclerosis (ALS), and other brain disorders caused by trauma or other insults including aging), inflammatory diseases (e.g., asthma, chronic obstructive pulmonary disease, rheumatoid arthritis, osteoarthritis, inflammatory bowel disease, multiple sclerosis, and disorders of the immune system), restenosis, cystic fibrosis, muscular dystrophy, Duchenne muscular dystrophy, non-alcoholic steatohepatitis, minimal change disease, idiopathic pulmonary fibrosis (IPF), emphysema and acute respiratory disease syndrome (ARDS), preeclampsia and pregnancy-induced hypertension, kidney diseases (focal segmental glomerulosclerosis, nephrotic syndrome, minimal change disease, membranous glomerulonephritis, rapidly progressive glomerulonephritis, hypertensive nephropathy, systemic lupus erythematosus, diabetic nephropathy, renal insufficiency, end stage renal disease, diabetic kidney disease (DKD) or chronic kidney disease), ischemia or an ischemic reperfusion injury, cancer, metabolic disorders such as diabetes. Methods for preventing or treating any of the foregoing or following diseases and conditions include treating any of the symptoms associated with these diseases or conditions. For example, methods for treating kidney disease contemplate treating symptoms including, but not limited to, secondary hypertension, proteinuria, lipiduria, hypercholesterolemia, hyperlipidemia, and coagulation abnormalities.

Because of the important role that calcium regulation plays in many cellular processes including cellular activation, cytoskeletal rearrangement, gene expression, cellular trafficking and apoptotic cell death, calcium dyshomeostasis is implicated in the many diseases and disorders. These diseases and disorders include neurological and neurodegenerative diseases and disorders; inflammatory diseases and disorders such as inflammatory bowel disease and Crohn's disease; kidney disease such as hypercalcemia, kidney stones, and polycystic kidney disease; metabolic diseases and disorders including obesity and diabetes; liver and kidney diseases and disorders; cardiovascular diseases and disorders including hypertension; respiratory diseases including COPD, IPAH, and asthma, and cancers, including cancers of the brain, breast, kidney, cervix, prostate, gastrointestinal tract, skin, and epithelia.

These disorders have been well characterized in man, but also exist with a similar etiology in other mammals, and can be treated by pharmaceutical compositions of the present invention.

Accordingly, a compound of the invention, as described herein, or a pharmaceutically acceptable salt thereof may be used for the preparation of a medicament for treating a disease or disorder mediated by TRPC6, including those mentioned above and in the Background and Detailed Description sections.

For therapeutic use, the compounds of the invention may be administered via a pharmaceutical composition in any conventional pharmaceutical dosage form in any conventional manner. Conventional dosage forms typically include a pharmaceutically acceptable carrier suitable to the particular dosage form selected. Routes of administration include, but are not limited to, intravenously, intramuscularly, subcutaneously, intrasynovially, by infusion, sublingually, transdermally, orally, topically or by inhalation. The preferred modes of administration are oral and intravenous.

The compounds of this invention may be administered alone or in combination with adjuvants that enhance stability of the inhibitors, facilitate administration of pharmaceutical compositions containing them in certain embodiments, provide increased dissolution or dispersion, increase inhibitory activity, provide adjunct therapy, and the like, including other active ingredients. In one embodiment, for example, multiple compounds of the present invention can be administered. Advantageously, such combination therapies utilize lower dosages of the conventional therapeutics, thus avoiding possible toxicity and adverse side effects incurred when those agents are used as monotherapies. Compounds of the invention may be physically combined with the conventional therapeutics or other adjuvants into a single pharmaceutical composition. Advantageously, the compounds may then be administered together in a single dosage form. In some embodiments, the pharmaceutical compositions comprising such combinations of compounds contain at least about 5%, but more preferably at least about 20%, of a compound of the invention (w/w) or a combination thereof. The optimum percentage (w/w) of a compound of the invention may vary and is within the purview of those skilled in the art. Alternatively, the compounds of the present invention and the conventional therapeutics or other adjuvants may be administered separately (either serially or in parallel). Separate dosing allows for greater flexibility in the dosing regime.

As mentioned above, dosage forms of the compounds of this invention may include pharmaceutically acceptable carriers and adjuvants known to those of ordinary skill in the art and suitable to the dosage form. These carriers and adjuvants include, for example, ion exchangers, alumina, aluminum stearate, lecithin, serum proteins, buffer substances, water, salts or electrolytes and cellulose-based substances. Preferred dosage forms include tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems,* 5th ed., Lea and Febiger (1990)). Dosage levels and requirements for the compounds of the present invention may be selected by those of ordinary skill in the art from available methods and techniques suitable for a particular patient. In some embodiments, dosage levels range from about 1-1000 mg/dose for a 70 kg patient. Although one dose per day may be sufficient, up to 5 doses per day may be given. For oral doses, up to 2000 mg/day may be required. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

What is claimed is:
1. A compound of formula (I)

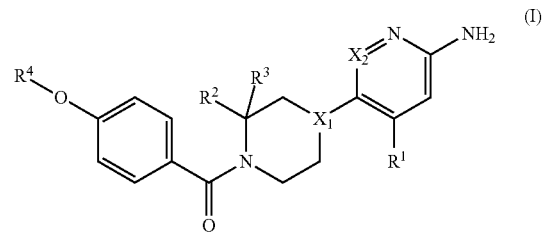

wherein
$X_1$ is CH or N;
$X_2$ is CH or N;
$R^1$ is H, $C_{1-3}$alkyl or $OC_{1-3}$alkyl,
$R^2$ is H or $C_{1-6}$alkyl optionally substituted with OH or $OC_{1-3}$alkyl,
$R^3$ is H or $C_{1-6}$alkyl,
$R^2$ and $R^3$ together with the carbon atom to which they are attached may optionally join to form a 3- to 6-membered carbocyclic ring,
$R^4$ represents a group of formula:

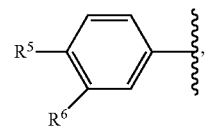

wherein
$R^5$ is selected from the group consisting of H, halo, $CF_3$, $OCF_3$, CN, $C_{1-6}$alkyl, $OC_{1-6}$alkyl, and $C_{3-6}$cycloalkyl; wherein each of the $C_{1-6}$alkyl and $OC_{1-6}$alkyl of the $R^5$ groups may be optionally substituted with one to three groups each independently selected from the group consisting of halo, oxo, $NH_2$, $NH(C_{1-6}alkyl)$, and $N(C_{1-6}alkyl)_2$,
$R^6$ is selected from the group consisting of H, halo, $C_{1-6}$alkyl and $OC_{1-6}$alkyl;
wherein
$R^5$ and $R^6$ may join to form a 5- or 6-membered carbocyclic ring wherein one or two carbon atoms of the carbocyclic ring may optionally be replaced by one or two oxygen atoms,
or a pharmaceutically acceptable salt thereof.

2. The compound according to claim 1, wherein $X_1$ is CH and $X_2$ is N, or a pharmaceutically acceptable salt thereof.

3. The compound according to claim 1, wherein $X_1$ is CH and $X_2$ is CH, or a pharmaceutically acceptable salt thereof.

4. The compound according to claim 1, wherein the $X_1$ is N and $X_2$ is CH, or a pharmaceutically acceptable salt thereof.

5. The compound according to claim 1, wherein $X_1$ is N and $X_2$ is CH, or a pharmaceutically acceptable salt thereof.

6. The compound according to claim 1, wherein
$R^5$ is selected from the group consisting of H, F, Cl, $CF_3$, $OCF_3$, CN, methyl, ethyl, isopropyl, methoxy, cyclopropyl, acetyl, and $(CH_3)_2NC(O)$—,
$R^6$ is selected from the group consisting of H, F, and methoxy;

wherein

R[5] and R[6] may join to form a 5- or 6-membered carbocyclic ring two carbon atoms of the carbocyclic are replaced by two oxygen atoms, or a pharmaceutically acceptable salt thereof.

7. The compound according to claim 1, wherein

R[5] is selected from the group consisting of H, F, Cl, CF$_3$, OCF$_3$, CN, methyl, ethyl, isopropyl, methoxy, cyclopropyl, acetyl, and (CH$_3$)$_2$NC(O)—, or a pharmaceutically acceptable salt thereof.

8. The compound according to claim 1, wherein

R[6] is selected from the group consisting of H, F, and methoxy;

or a pharmaceutically acceptable salt thereof.

9. A compound selected from the group consisting of

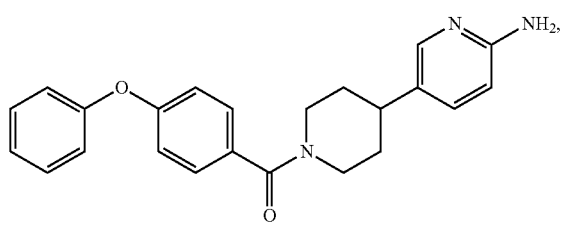

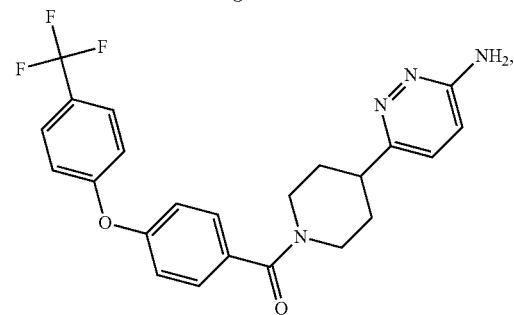

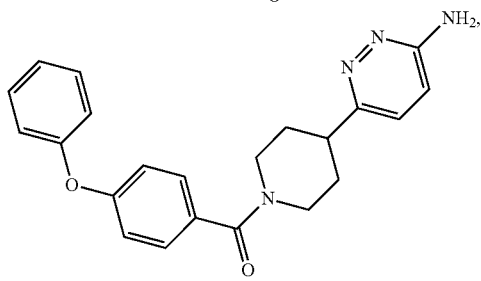

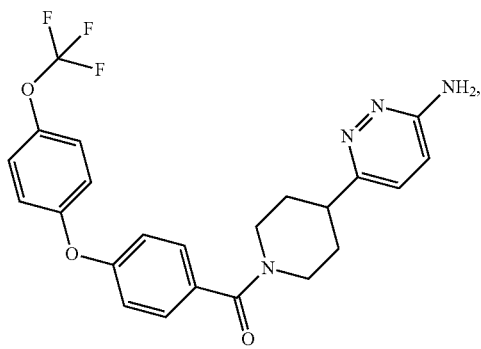

-continued

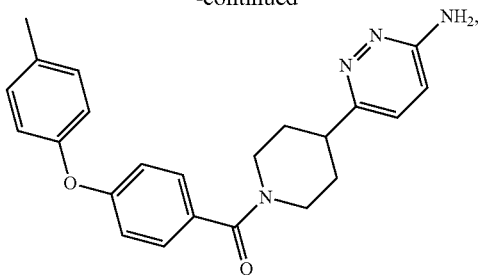

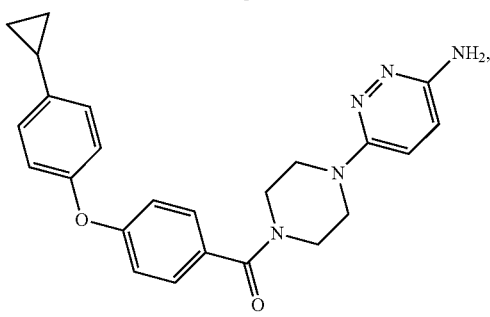

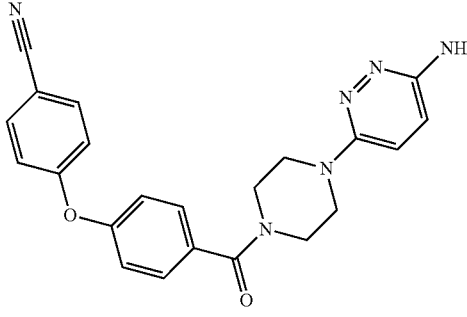

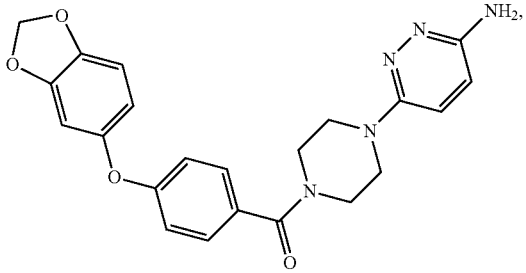

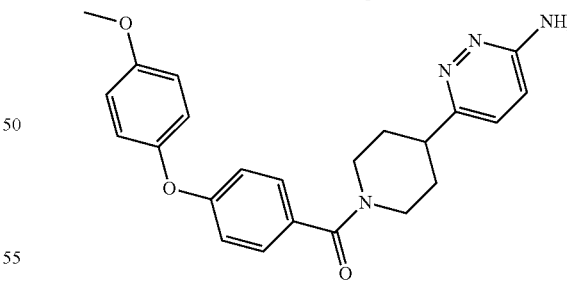

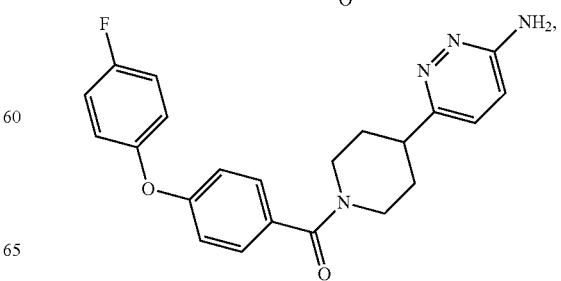

111
-continued
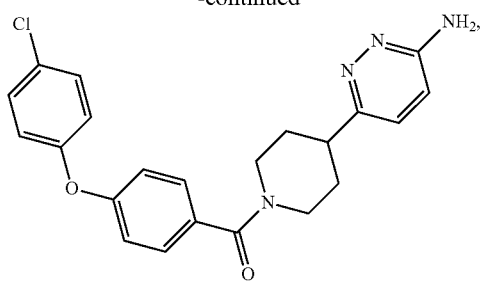
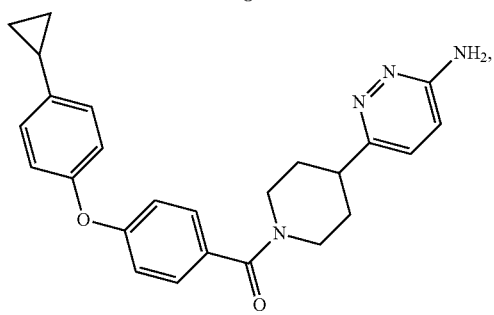
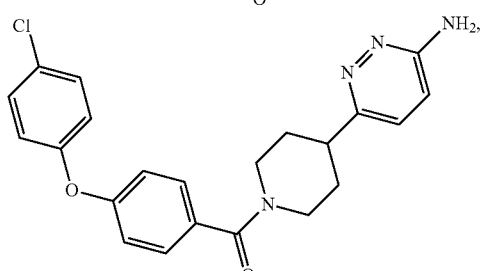
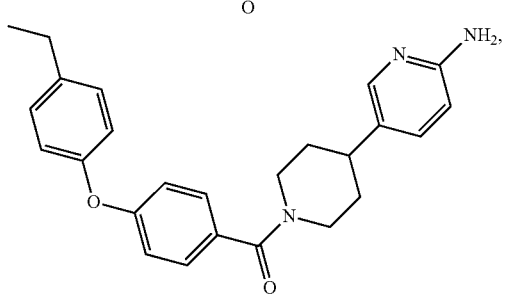
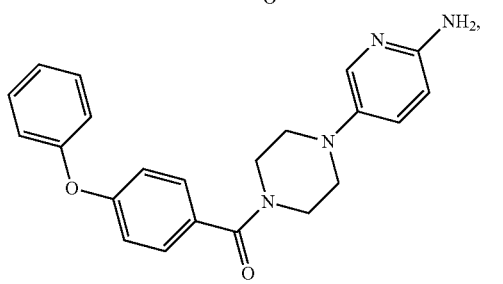
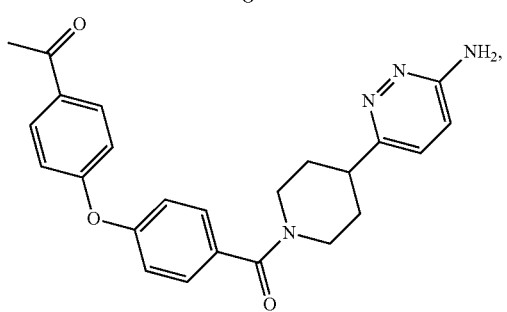
112
-continued
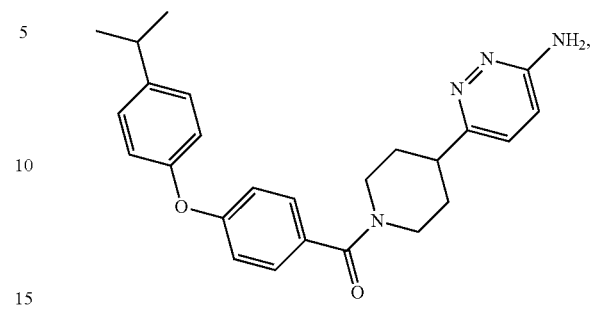
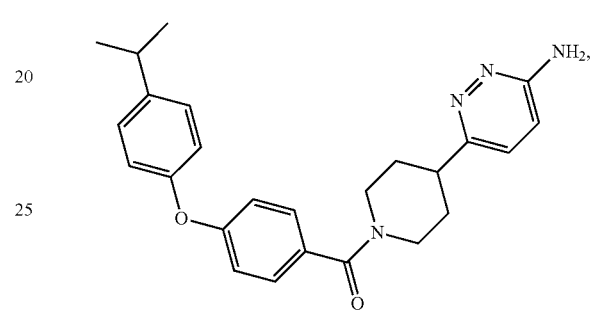
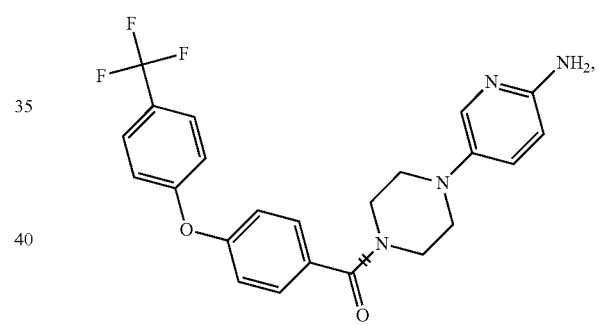
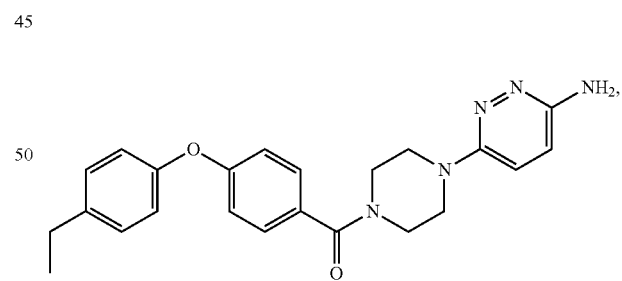
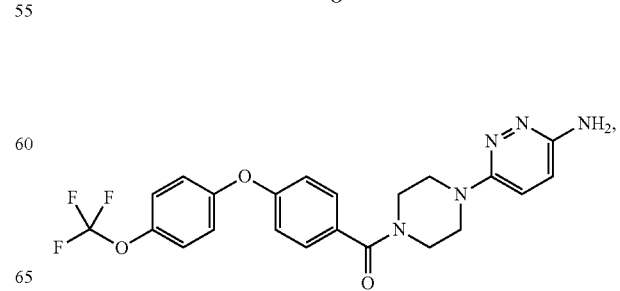

113
-continued
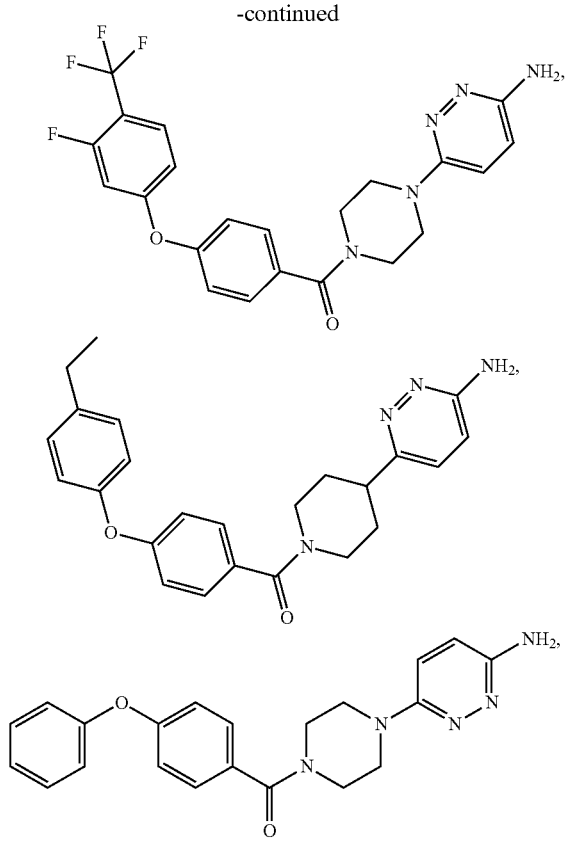
114
-continued
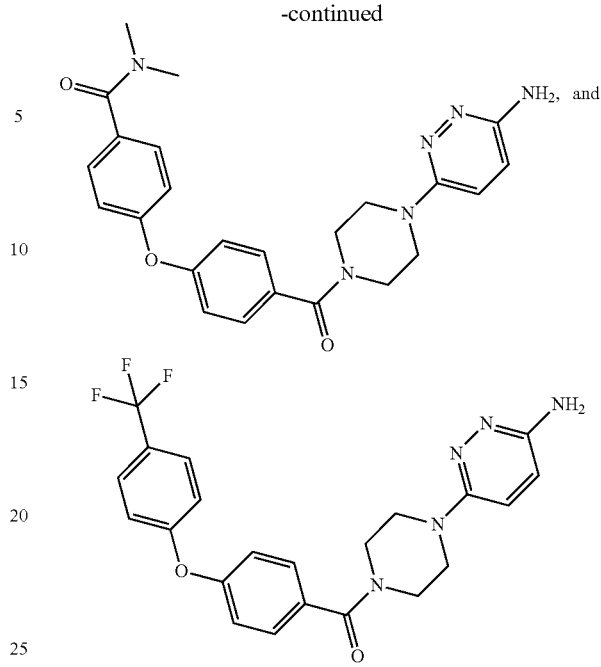
and the pharmaceutically acceptable salts thereof.
10. A pharmaceutical composition comprising a compound according to claim 1, or a pharmaceutically acceptable salt thereof, and a pharmaceutically acceptable excipient or carrier.
* * * * *